US008586291B2

(12) United States Patent
Sawyers et al.

(10) Patent No.: US 8,586,291 B2
(45) Date of Patent: *Nov. 19, 2013

(54) MUTATIONS IN THE BCR-ABL TYROSINE KINASE ASSOCIATED WITH RESISTANCE TO STI-571

(75) Inventors: Charles L. Sawyers, Los Angeles, CA (US); Mercedes E. Gorre, Los Angeles, CA (US); Neil Pravin Shah, Woodland Hills, CA (US); John Nicoll, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 398 days.

This patent is subject to a terminal disclaimer.

(21) Appl. No.: 12/381,448

(22) Filed: Mar. 11, 2009

(65) Prior Publication Data

US 2010/0055687 A1     Mar. 4, 2010

Related U.S. Application Data

(63) Continuation of application No. 10/171,889, filed on Jun. 14, 2002, now Pat. No. 7,521,175.

(60) Provisional application No. 60/298,728, filed on Jun. 14, 2001, provisional application No. 60/331,709, filed on Nov. 20, 2001.

(51) Int. Cl.
*C12Q 1/00* (2006.01)
*G01N 33/574* (2006.01)

(52) U.S. Cl.
USPC .................................. 435/4; 435/6; 435/7.25

(58) Field of Classification Search
None
See application file for complete search history.

(56) References Cited

U.S. PATENT DOCUMENTS

| | | | |
|---|---|---|---|
| 5,506,107 A | 4/1996 | Cunningham et al. | |
| 6,004,931 A | 12/1999 | Cunningham et al. | |
| 7,326,534 B2 | 2/2008 | Druker | |
| 7,416,873 B2 | 8/2008 | Druker | |
| 7,521,175 B2 | 4/2009 | Sawyers et al. | |
| 2003/0162222 A1* | 8/2003 | Warmuth et al. | 435/7.1 |
| 2003/0170851 A1 | 9/2003 | Barthe et al. | |
| 2005/0202519 A1* | 9/2005 | Barthe et al. | 435/15 |
| 2006/0148058 A1 | 7/2006 | Barthe et al. | |
| 2008/0305492 A1 | 12/2008 | Druker | |
| 2009/0117641 A1 | 5/2009 | Barthe et al. | |

FOREIGN PATENT DOCUMENTS

| | | |
|---|---|---|
| WO | 97/08184 | 3/1997 |
| WO | 01/07659 | 2/2001 |
| WO | 03/031608 | 4/2003 |
| WO | WO 03/031608 * | 4/2003 |

OTHER PUBLICATIONS

Senechal et al, Mol Cell Bil 18:5082-5090, 1998.*
Barthe et al and Hochhaus, Science 293: 2163a Sep. 21, 2001.*
Allen et al., "An Activating Mutation in the ATP Binding Site of the ABL Kinase Domain," J. Biol. Chem., 1996, 271: 19585-19591.
Branford et al., "High Frequency of Point Mutations Clustered Within the Adenosine Triphosphate-Binding Region of BCR/ABL in Patients . . . ," Blood, 2002, 99(9): 3472-3475.
Druker et al., "Activity of a Specific Inhibitor of the BCR-ABL Tyrosine Kinase in the Blast Crisis of Chronic Myeloid Leukemia and Acute . . . ," N. Engl. J. Med., 2001, 344(14): 1038-1042.
Druker et al., "Effects of a Selective Inhibitor of the Abl Tyrosine Kinase on the Growth of Bcr-Abl Positive Cells," Nature Med., 1996, 2(5): 561-566.
Druker et al., "Efficacy and Safety of a Specific Inhibitor of the BCR-ABL Tyrosine Kinase in Chronic Myeloid Leukemia," N. Engl. J. Med., 2001, 344(14): 1031-1037.
Gambacorti-Passerini et al., "Role of $\alpha$1 Acid Glycoprotein in the In Vivo Resistance of Human BCR-ABL Leukemic Cells to the Abl Inhibitor STI571," J. Natl. Cancer Inst., 2000, 92(20): 1641-1650.
Gorre et al., "Clinical Resistance to STI-571 Cancer Therapy Caused by BCR-ABL Gene Mutation or Amplification," Science, 2001, 293: 876-880.
Hofmann et al., "Ph+ Acute Lymphoblastic Leukemia Resistant to the Tyrosine Kinase Inhibitor STI571 Has a Unique BCR-ABL Gene Mutation," Blood, 2002, 99(5): 1860-1862.
le Coutre et al., "Induction of Resistance to the Abelson Inhibitor STI571 in Human Leukemic Cells Through Gene Amplification," Blood, 2000, 95(5): 1758-1766.
Mahon et al., "Selection and Characterization of BCR-ABL Positive Cell Lines with Differential Sensitivity to the Tyrosine Kinase Inhibitor . . . ," Blood, 2000, 96(3): 1070-1079.
Schindler et al., "Structural Mechanism for STI-571 Inhibition of Abelson Tyrosine Kinase," Science, 2000, 289: 1938-1942.
Senechal et al., "Structural Requirements for Function of the Crk1 Adapter Protein in Fibroblasts and Hematopoietic Cells," Mol. Cell. Biol., 1998, 18(9): 5082-5090.
Technical Comments, Barthe, Hochhaus, Gambacorti-Passerini, and Gorre, "Roots of Clinical Resistance to STI-571 Cancer Therapy," Science, 2001, 293: 2163a, 3 pp.
Von Bubnoff et al., "BCR-ABL Gene Mutations in Relation to Clinical Resistance of Philadelphia-chromosome-positive Leukaemia . . . ," The Lancet, 2002, 359: 487-491.
Weisberg et al., "Mechanism of Resistance to the ABL Tyrosine Kinase Inhibitor STI571 in BCR/ABL-transformed Hematopoietic Cell Lines," Blood, 2000, 95(11): 3498-3505.
Kreil, Sebastian et al., "Molecular and chromosomal mechanisms of resistance in CML patients after STI571 (Glivec) therapy", *Blood*, 98(11), Part I, Nov. 16, 2001, p. 435a, XP009049670 & 43rd Annual Meeting of the American Society of Hematology, Part 1, Orlando, Florida, Dec. 7-11, 2001. Abstract.
Laurent, Eunice et al., "The BCR gene and Philadelphia chromosome-positive leukemogenesis", *Cancer Research*, 61(6), Mar. 15, 2001, pp. 2343-2355, XP002333231. Abstract.
Feinstein et al., "Nucleotide sequence analysis of human abl and bcr-abl cDNAs", Oncogene (1989), vol. 4, pp. 1477-1481.
Gambacorti-Passerini et al, "Gene amplification the most likely mechanism of resistance to STI571 in LAMA84R cells", Blood (2000), vol. 96, pp. 4004-4005.

(Continued)

*Primary Examiner* — Lei Yao
(74) *Attorney, Agent, or Firm* — Kenyon & Kenyon LLP

(57) ABSTRACT

The invention described herein relates to novel genes and their encoded proteins, termed Mutants Associated with Resistance to STI-571 (e.g., T315I Bcr-Abl), and to diagnostic and therapeutic methods and compositions useful in the management of various cancers that express MARS. The invention further provides methods for identifying molecules that bind to and/or modulate the functional activity of MARS.

18 Claims, 13 Drawing Sheets

(56) References Cited

OTHER PUBLICATIONS

Hochhaus et al., "Molecular and Chromosomal Mechanisms of Resistance to Imatinib (STI571) Therapy", Leukemia (2002), vol. 16, pp. 2190-2196.

Knight, "Another possible mechanism of resistance to STI571", Blood (2000), vol. 96, pp. 4003-4004.

Soshiki Baiyou Kougaku "Anit-cancer drugs targeting cancer-related gene products", Tissue Culture Engineering (May 2001 extra edition) vol. 27, pp. 32-35.

Shah, Neil et al., Abstract # 3205 "Resistance to Geevec: Sequence Analysis Reveals a Spectrum of BCR/ABL Kinase Domain Mutations in Both Acquired- and De Novo-Resistant Cases of Chronic Myelogenous Leukemia (CML) in Myeloid Blast Crisis" Blood (2001), vol. 98:11, pp. 770A.

Shah, Neil et al., "Multiple BCR-ABL Kinase Domain Mutations Confer Polyclonal Resistance to the Tyrosine Kinase Inhibitor Imatinib (STI571) in Chronic Phase and Blast Crisis Chronice Myeloid Leukemia", Cancer Cell (2002), vol. 2, pp. 117-125.

Weisberg, E. et al., "Mechanisms of Resistance Imatinib (STI571) in Preclinical Models and in Leukemia Patients". Drug Resistance Updates (2001), vol. 4:1, pp. 22-28.

Carroll, Martin, et al., "CGP 57148, a Tyrosine Kinase Inhibitor, Inhibits the Growth of Cells Expressing BCR-ABL, TEL-ABL, and TEL-PDGFR Fusion Proteins", (1997), Blood, vol. 90, No. 12, pp. 4947-4952.

Deininger, Michael W. N. et al., "The Tyrosine Kinase Inhibitor CGP571148B Selectively inhibits the Growth of BCR-ABL-Positive Cells". (1997) Blood, vol. 90, No. 9, pp. 3691-3698.

Zimmerman, et al., "Potent and Selective Inhibitors of the ABL-Kinase: Phenylamino-Pyrimidine (PAP) Derivatives". Bioorganic & Medicinal Chemistry Letters (1997), vol. 7:2, pp. 187-192.

Dorsey, J. F. et al., "The pyridol [2,3-d]pyrimidine derivative PD180970 inhibits p210Bcr-Abl tyrosine kinase and induces apoptosis of K562 leukemic cells". (2000). Cancer Research vol. 15;60(12), pp. 3127-3131.

Okuda, K. et al., "ARG tyrosine kinase is inhibited by ST1571". (2001) Blood vol. 97 (8), pp. 2440-2448.

Blood (2001) vol. 98, No. 11, p. 435a, #1823.

Von Bubnoff, N. et al Abstract # 3207, Blood (2001), vol. 98, vol. 11., pp. 770a.

Hofmann, et al, Abstract #3486, Ph+ Acute Lymphoblastic Leukemias Resistant to STI571 (Glivec) Have a Novel and Unique BCR-ABL Gene Mutation, Blood (2001), vol. 98:11, p. 839a; and 43rd Annual Meeting of the Am. Soc. of Hematolgoy, Pt. 1; Orlando, Fl., Dec. 7-11, 2001.

Al-Ali et al., "High Incidence of BCR-ABL kinase domain mutations and absence of mutations of the PDGFR and KIT activation loops in CML patients with secondary resistance to imatinib," Hematology Journal, 5(1):55-60 (2004).

Bradeen et al., "Comparison of imatinib mesylate, dasatinib (BMS-354825), and nilotinib (AMN107) in an N-ethyl-N-nitrosourea (ENU)-based mutagenesis screen: High efficacy of drug combinations," Blood, 108(7):2332-2338 (2006).

Braziel et al., "Hematopathologic and cytogenetic findings in imatinib mesylate-treated chronic myelogenous leukemia patients: 14 months' experience," Blood, 100(2):435-441 (2002).

Chuah et al., "Zoledronate inhibits proliferation and induces apoptosis of imatinib-resistant chronic myeloid leukaemia cells," Leukemia, 19(11):1896-1904 (2005).

Collins et al., "A branched DNA signal amplification assay for quantification of nucleic acid targets below 100 molecules-ml," Nucleic Acids Research, 25(15):2979-2984 (1997).

Corbin et al., "Analysis of the structural basis of specificity of inhibition of the Abl kinase by STI571," Journal of Biological Chemistry, 277(35):32214-32219 (2002).

Corbin et al., "Several Bcr-Abl kinase domain mutants associated with imatinib mesylate resistance remain sensitive to imatinib," Blood, 101(11):4611-4614 (2003).

Crossman et al., "A single nucleotide polymorphism in the coding region of ABL and its effects on sensitivity to imatinib," Leukemia, 19(11):1859-1862 (2005).

Dash et al., "A murine model of CML blast crisis induced by cooperation between BCR-ABL and NUP98-HOAX9," PNAS, 99(11):7622-7627 (2002).

Deininger et al., "Specific targeted therapy of chronic myelogenous leukemia with imatinib," Pharmacological Reviews, 55(3):401-423 (2003).

Deininger et al., "SRCircumventing imatinib resistance," Cancer Cell, 6(2):108-110 (2004).

Deininger et al., "The development of imatinib as a therapeutic agent for chronic myeloid leukemia," Blood, 105 (7):2640-2653 (2005).

Demetri et al., "Efficacy and safety of imatinib mesylate in advanced gastrointestinal stromal tumors," New England Journal of Medicine, 347(7):472-480 (2002).

Druker, "Imatinib as a paradigm of targeted therapies," Advances in Cancer Research, 91:1-30 (2004).

Druker, "Imatinib mesylate in the treatment of chronic myeloid leukaemia," Expert Opinion on Pharmacotherapy, 4 (6):963-971 (2003).

Druker, "Inhibition of the Bcr-Abl tyrosine kinase as a therapeutic strategy for CML," Oncogene, 21(56):8541-8546 (2002).

Druker, "Inhibitors of Protein Kinases and Protein Phosphates," EDs Pinna & Cohen HEP, 167:391-410 (2005).

Druker, "Perspectives on the development of a molecularly targeted agent," Cancer Cell, 1(1):31-36 (2002).

Druker, "STI571 (Gleevec™) as a paradigm for cancer therapy," Trends in Molecular Medicine, 8(4 Suppl):S14-S18 (2002).

Griswold et al., "Kinase domain mutants of Bcr-Abl exhibit altered transformation potency, kinase activity, and substrate utilization, irrespective of sensitivity to imatinib," Molecular and Cellular Biology, 26(16):6082-6093 (2006).

Harlow et al., "Antibodies, a laboratory manual," Cold Spring Harbor Laboratory Press, 141-142 (1988).

Hughes et al., "Monitoring CML patients responding to treatment with tyrosine kinase inhibitors: Review and recommendations for harmonizing current methodology for detecting BCR-ABL transcripts and kinase domain mutations and for expressing results," Blood, 108(1):28-37 (2006).

Kougaku, "Anti-cancer drugs targeting cancer-related gene products," Tissue Culture Engineering, 27(6):32-35 (2001).

Kouklis et al., "In vitro assembly properties of vimentin mutagenized at the beta-site tail motif," Journal of Cell Science, 106(Pt. 3):919-928 (1993).

Kurzrock et al., "Philadelphia Chromosome-Positive Leukemias: From Basic Mechanisms to Molecular Therapeutics," Annals of Internal Medicine, 138:819-830 (2003).

La Rosée et al., "Activity of the Bcr-Abl kinase inhibitor PD180970 against clinically relevant Bcr-Abl isoforms that cause resistance to imatinib mesylate (Gleevec, STI571)," Cancer Research, 62(24):7149-7153 (2002).

La Rosée et al., "In vitro efficacy of combined treatment depends on the underlying mechanism of resistance in imatinib-resistant Bcr-Ab1-positive cell lines," Blood, 103(1):208-215 (2004).

La Rosée et al., "In vitro studies of the combination of imatinib mesylate (Gleevec) and arsenic trioxide (Trisenox) in chronic myelogenous leukemia," Experimental Hematology, 30(7):729-737 (2002).

La Rosée et al., "Insights from pre-clinical studies for new combination treatment regimens with the Bcr-Abl kinase inhibitor imatinib mesylate (Gleevec-Glivec) in chronic myelogenous leukemia: A translational perspective," Leukemia, 16(7):1213-1219 (2002).

Mauro et al., "STI571: A paradigm of new agents for cancer therapeutics," Journal of Clinical Oncology, 20 (1):325-334 (2002).

O'Dwyer et al., "STI571 as a targeted therapy for CML," Cancer Investigation, 21(3):429-438 (2003).

(56) References Cited

OTHER PUBLICATIONS

O'Hare et al., "Inhibition of wild-type and mutant Bcr-Abl by AP23464, a potent ATP-based oncogenic protein kinase inhibitor: Implications for CML," Blood, 104(8):2532-2539 (2004).

Pasternack et al., "Evaluation of the Gen-Probe *Chlamydia trachomatis* transcription-mediated amplification assay with urine specimens from women," Journal of Clinical Microbiology, 35(3):676-678 (1997).

Press et al., "A half-log increase in BCR-ABL RNA predicts a higher risk of relapse in patients with chronic myeloid leukemia with an imatinib-induced complete cytogenetic response," Clinical Cancer Research, 13(20):6136-6143 (2007).

Roumiantsev et al., "A point mutation in the Abl catalytic domain induces resistance to the Tyrosine kinase inhibitor STI 571," Blood, 96(11):470a (2000) (Abstract 2023).

Sawyers et al., "Imatinib induces hematologic and cytogenetic responses in patients with chronic myelogenous leukemia in myeloid blast crisis: results of a phase II study," Blood, 99(10):3530-3539 (2002).

Sherbenou et al., "Applying the discovery of the Philadelphia chromosome," Journal of Clinical Investigation, 117 (8):2067-2074 (2007).

Straub et al., "Cassette Mutagenesis of a Potential Substrate Recognition Region of Cytochrome P450 2C2," Journal of Biological Chemistry, 268(29): 21997-20003 (1993).

Tseng et al., "Synergistic interactions between imatinib mesylate and the novel phosphoinositide-dependent kinase-1 inhibitor OSU-03012 in overcoming imatinib mesylate resistance," Blood, 105(10):4021-4027 (2005).

* cited by examiner

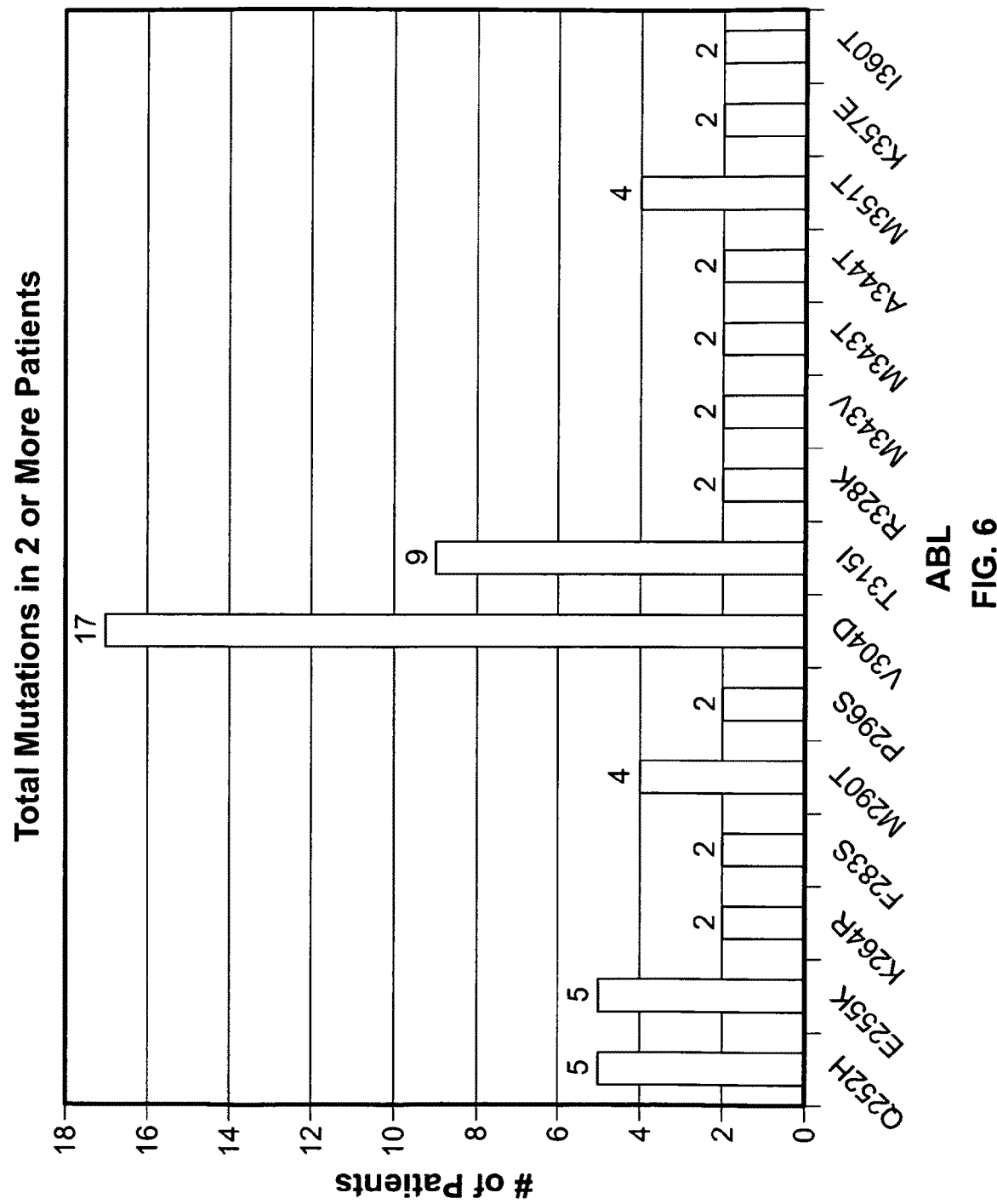

```
                           P-loop
      |  10      | * *20* *|  30      |  40
  1 DKWEMERTDITMKHKL GGGQYGEV YEGVWKKYSLTVAVKTLKE      43
                    ↓ ↓↓ ↓
                    E HH K
                      F
```

```
       50     |    60    |   70     |   80    |   90
          helix c
 44 DTM EVEEFLKEAAVMKEI KHPNLVQLLGVCTREPPFYIITEFMTYG   91
                                              ↓ ↓
                                              I L
```

```
       95     |   105    |  115     |  125    |  135
                                                catalytic
                                                 domain
 92 NLLDYLRECNRZEVNAVVLLYMATQISSAMEYLEKKNFI HRDLAAR   138
                                 ↓     ↓    ↓
                                 T     G    V
```

```
      |  145    |  155    |  165    |  175    |
                     activation loop
139 NCLVGENHLVKV ADFGLSRLMTGDTYTAHAGAKFP IKWTAPESLA   183
                ↓                ↓
                I                R
                                 P
```

FIG. 10

MUTATIONS IN THE BCR-ABL TYROSINE KINASE ASSOCIATED WITH RESISTANCE TO ST1-571

RELATED APPLICATIONS

This application is a continuation of U.S. application Ser. No. 10/171,889 filed Jun. 14, 2002, which issued as U.S. Pat. No. 7,521,175 which claims priority under Section 119(e) from U.S. Provisional Application Ser. No. 60/298,728 filed Jun. 14, 2001 and U.S. Provisional Application Ser. No. 60/331,709 filed Nov. 20, 2001, the contents of each of which are incorporated herein by reference.

STATEMENT OF GOVERNMENT SUPPORT

This invention was made with Government support by a USPHS National Research Service Award GM07185 (M.E.G.). The Government may have certain rights in this invention.

SEQUENCE LISTING

The instant application contains a Sequence Listing which has been submitted in ASCII format via EFS-Web and is hereby incorporated by reference in its entirety. Said ASCII copy, created on Dec. 22, 2011, is named 1496AUS4.txt and is 16,752 bytes in size.

FIELD OF THE INVENTION

The invention described herein relates to novel genes and their encoded proteins, and to diagnostic and therapeutic methods and compositions useful in the management of cancers that express them.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise and are predicted to become the leading cause of death in the developed world.

Cancers are characterized by multiple oncogenic events that collectively contribute to the phenotype of advanced stage disease. With the advent of new drugs that target specific molecular abnormalities, it is important to know whether the initial oncogenic event continues to play a functional role at later stages of tumor progression and at relapse with the development of chemotherapy resistance. This question has been addressed in transgenic mice through regulated expression of the initial oncogene. In three models testing different oncogenes in different tissues, the primary oncogene was required to maintain the tumor phenotype, despite the presence of numerous additional oncogene and tumor suppressor mutations (see, e.g. L. Chin et al., *Nature* 400, 468 (1999); D. W. Felsher et al., *Mol. Cell* 4, 199 (1999); and C. S. Huettner et al., *Nature Genet.* 24, 57 (2000)). Recent clinical trials of the Abelson tyrosine kinase (Abl) inhibitor STI-571 in chronic myeloid leukemia (CML) allow this question to be addressed directly in human cancer (see, e.g. B. J. Druker et al., *N. Engl. J. Med.* 344, 1038 (2001); and B. J. Druker et al., *N. Engl. J. Med.* 344, 1031 (2001)).

CML is a pluripotent hematopoietic stem cell disorder characterized by the Philadelphia (Ph) chromosome translocation (see, e.g. C. L. Sawyers, *N. Engl. J. Med.* 340, 1330 (1999); and S. Faderl et al., *N. Engl. J. Med.* 341, 164 (1999)). The resulting BCR-ABL fusion gene encodes a cytoplasmic protein with constitutive tyrosine kinase activity (see, e.g. J. B. Konopka et al., *Proc. Natl. Acad. Sci. U.S.A.* 82, 1810 (1985) and NCBI Accession NP_067585). Numerous experimental models have established that BCR-ABL is an oncogene and is sufficient to produce CML-like disease in mice (see, e.g. G. Q. Daley et al., *Science* 247, 824 (1990); and N. Heisterkamp et al., *Nature* 344, 251 (1990)). CML progresses through distinct clinical stages. The earliest stage, termed chronic phase, is characterized by expansion of terminally differentiated neutrophils. Over several years the disease progresses to an acute phase termed blast crisis, characterized by maturation arrest with excessive numbers of undifferentiated myeloid or lymphoid progenitor cells. The BCR-ABL oncogene is expressed at all stages, but blast crisis is characterized by multiple additional genetic and molecular changes.

A series of inhibitors, based on the 2-phenylaminopyrimidine class of pharmacophores, has been identified that have exceptionally high affinity and specificity for Abl (see, e.g., Zimmerman et al., Bloorg, Med. Chem. Lett. 7, 187 (1997). The most successful of these, STI-571 (formerly referred to as Novartis test compound CGP 57148 and also known as Gleevec and imatinib), has been successfully tested in clinical trail a therapeutic agent for CML. STI-571 is a 2-phenylamino pyrimidine that targets the ATP-binding site of the kinase domain of ABL (see, e.g. B. J. Druker et al., *Nature Med.* 2, 561 (1996)). In phase I clinical trials, STI-571 induced remissions in patients in chronic phase as well as blast crisis (see, e.g. B. J. Druker et al., *N. Engl. J. Med.* 344, 1038 (2001); and B. J. Druker et al., *N. Engl. J. Med.* 344, 1031 (2001)). While responses in chronic phase have been durable, remissions observed in blast crisis patients have usually lasted only 2-6 months, despite continued drug treatment (see, e.g. B. J. Druker et al., *N. Engl. J. Med.* 344, 1038 (2001)).

In view of the relapse observed in patients treated with STI-571 there is a need for an understanding of the mechanisms associated with STI-571 resistance in CML and related cancers as well as diagnostic and therapeutic procedures and compositions tailored to address this phenomena. The invention provided herein satisfies this need.

SUMMARY OF THE INVENTION

Clinical studies with the Abl tyrosine kinase inhibitor STI-571 in chronic myeloid leukemia (CML) demonstrate that many patients with advanced stage disease respond initially but then relapse. While, biochemical and molecular analysis of clinical materials from these patients shows that drug resistance is associated with reactivation of Bcr-Abl signal transduction, the specific events associated with this resistance have not been not well characterized.

The disclosure provided herein characterizes specific events associated with such drug resistance by identifying specific domains within protein kinases where amino acid mutations occur that impart resistance to the kinase inhibitor yet allow the kinase to retain its biological activity. The disclosure provided herein further identifies these regions as domains shown to be highly conserved among families of protein kinases (e.g. the c-Abl tyrosine kinase activation loop). Consequently this disclosure identifies those specific regions in protein kinases that are to be analyzed in a variety of diagnostic protocols which examine drug resistance.

The invention described herein further includes novel genes and their encoded proteins expressed in cancer cells that are associated with resistance to STI-571. Typically these STI-571 resistant genes and their encoded proteins are mutants of Bcr-Abl an oncogene that is expressed in chronic myeloid leukemias. The invention described herein discloses a number of Bcr-Abl Mutants Associated with Resistance to STI-571 hereinafter these mutants are collectively described using the acronym "MARS"), as well as diagnostic and therapeutic methods and compositions useful in the management of cancers that express these mutants.

A typical example of a MARS is a Bcr-Abl mutant having a single amino acid substitution in a Thr residue at position 315 of the Abl kinase (termed T315I Bcr-Abl). In clinical studies, patients exhibited STI-571 resistance associated with this mutation at residue 315, a residue in the Abl kinase domain known to form a critical hydrogen bond with this drug. Biochemical analyses of this mutant show that the Thr→Ile change is sufficient to confer STI-571 resistance in a reconstitution experiment. Additional MARS are identified in Tables I provided below. The disclosure provided herein presents evidence that genetically complex cancers retain dependence on an initial oncogenic events and provides a strategy for identifying inhibitors of STI-571 resistance. The disclosure provided herein further provides for a variety of diagnostic methods for examining the characteristics of cancers such as chronic myeloid leukemia.

All prior knowledge of the Bcr-Abl tyrosine kinase is based on published sequence that has been in the public domain for >15 years. The invention provides novel sequences of DNA of the Bcr-Abl tyrosine kinase fusion protein that causes chronic myeloid leukemia (CML), which is present in a high fraction of patients who develop resistance to the drug STI-571, which is soon to become standard of care for the treatment of CML. As disclosed herein, methods for evaluating the status of the MARS polypeptides and polynucleotides it can be used in the evaluation of cancers, for example to detect early relapse. Moreover, MARS polypeptides and polynucleotides can be used to create assays to identify drugs which inhibit the biological activity of these mutant proteins.

T315I Bcr-Abl provides a representative example of the inventions provided by the MARS disclosed herein. The T315I Bcr-Abl mutant disclosed herein contains an amino acid change in the kinase domain of Bcr-Abl that inhibits STI571 binding to Bcr-Abl. The T315I Bcr-Abl embodiment of the invention has been tested in a number of patient samples and confirmed at the sequence level. This mutant Bcr-Abl protein has been expressed in cells and shown to be resistant to STI-571. Therefore, patients develop resistance to the drug because it can no longer inhibit its kinase activity.

Knowledge of mutant sequences provide immediate utility for a number of methods. In particular, currently there are no methods for detecting or treating drug-resistant CML. Consequently, the invention provided herein provides diagnostic tests for early relapse in CML as well as for drug development in the field of tyrosine kinase inhibitors. For example, the disclosure provided herein allows one to detect the presence of drug resistant cells in CML patients prior to relapse, using, for example, PCR based assays. Representative embodiments of the invention include PCR and analogous assays that are used to detect resistant cells in patient blood samples.

The invention can also be practiced as a tool to identify molecules which bind and/or inhibit the mutant tyrosine kinases. A typical embodiment of this aspect of the invention is a method of identifying a compound which specifically binds to a mutant protein kinase such as a Bcr-Abl mutant shown in Table I by contacting the mutant with a test compound under conditions favorable to binding; and then determining whether said test compound binds to the mutant so that a compound which binds to the mutant is identified. Using such methods one can perform structure-based drug design and/or high throughput screening of chemical libraries to identify inhibitors of mutant tyrosine kinases. Such an inhibitor will have immediate clinical relevance.

The invention provides polynucleotides corresponding or complementary to all or part of the MARS genes, mRNAs, and/or coding sequences, preferably in isolated form, including polynucleotides encoding MARS proteins and fragments thereof, DNA, RNA, DNA/RNA hybrid, and related molecules, polynucleotides or oligonucleotides complementary to the MARS genes or mRNA sequences or parts thereof, and polynucleotides or oligonucleotides that hybridize to the MARS genes, mRNAs, or to MARS-encoding polynucleotides. Also provided are means for isolating cDNAs and the genes encoding MARS. Recombinant DNA molecules containing MARS polynucleotides, cells transformed or transduced with such molecules, and host-vector systems for the expression of MARS gene products are also provided. The invention further provides MARS proteins and polypeptide fragments thereof. The invention further provides antibodies that bind to MARS proteins and polypeptide fragments thereof, including polyclonal and monoclonal antibodies, murine and other mammalian antibodies, chimeric antibodies, humanized and fully human antibodies, and antibodies labeled with a detectable marker.

The invention further provides methods for detecting the presence and status of MARS polynucleotides and proteins in various biological samples, as well as methods for identifying cells that express MARS. A typical embodiment of this invention provides methods for monitoring MARS gene products in a tissue sample having or suspected of having some form of growth dysregulation such as cancer.

One preferred embodiment of the invention is a method of identifying a mutant Abelson tyrosine kinase expressed by a cell by determining a nucleotide sequence of a portion of the catalytic domain of the Abelson tyrosine kinase expressed by the cell and then comparing the nucleotide sequence so determined to that of the wild type sequence of the catalytic domain of the Abelson protein tyrosine kinase to identify the presence of a mutation within the catalytic domain, wherein the mutation so identified has the characteristics of occurring at a amino acid residue located within the polypeptide sequence of the Abelson protein tyrosine kinase at a amino acid residue that has homology to an amino acid position in a Bcr-Abl kinase shown in SEQ ID NO: 1 that is associated with a resistance to an inhibition of tyrosine kinase activity by a 2-phenylaminopyrimidine, wherein the homology between the amino acid residue located within the polypeptide sequence of the Abelson protein tyrosine kinase and the amino acid residue in the Bcr-Abl kinase shown in SEQ ID NO: 1 that is associated with a resistance to an inhibition of tyrosine kinase activity by a 2-phenylaminopyrimidine can be illustrated via a BLAST analysis.

Another embodiment of the invention is an isolated Bcr-Abl polypeptide comprising an amino acid sequence which differs from the sequence of the Bcr-Abl of SEQ ID NO:1 and has one or more amino acid substitutions at the residue position(s) in SEQ ID NO:1 selected from the group consisting of: D233, T243, M244, K245, G249, G250, G251, Q252, Y253, E255, V256L Y257, F259, K262, D263, K264, S265, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, and T406. A related embodiment of the invention is an isolated nucleic acid comprising a nucleotide sequence encoding the Bcr-Abl polypeptide. Other embodiments of the invention is a vector comprising this nucleic acid sequence, a host cell comprising such vectors (e.g. *E. coli*) as well as a method of making Bcr-Abl polypeptide variant polypeptide, comprising the steps of: providing a host cell comprising such a vector; (b) providing culture media; (c) culturing the host cell in the culture media under conditions sufficient to express the Bcr-Abl polypeptide variant polypeptide; (d) recovering the Bcr-Abl polypeptide variant polypeptide from the host cell or culture media; and (e) purifying the Bcr-Abl polypeptide variant polypeptide. Yet another embodiment of the invention is a Bcr-Abl polypeptide variant polypeptide that is chemically modified or conjugated or linked to a matrix or a heterologous protein.

The invention further provides various therapeutic compositions and strategies for treating cancers that express MARS, including methods for identifying molecules (e.g. STI-571 analogs) which inhibit the biological activities (e.g. kinase activity) of various MARS.

BRIEF DESCRIPTION OF THE FIGURES

FIG. 6. Bar graph schematic of total mutations in 2 or more patients.

FIG. 10. Imatinib-resistant mutations occur over a wide range of the Bcr-Abl kinase domain (SEQ ID NO: 20). The kinase domain amino acid sequence of wild-type Bcr-Abl is shown. Asterisks mark the conserved amino acids of the Gly-X-Gly-X-X-Gly-X-Val consensus sequence (SEQ ID NO: 21) found within the P-loop Amino acid substitutions found in STI-571-resistant patients are indicated beneath the wild-type sequence.

DETAILED DESCRIPTION OF THE INVENTION

Figure 1A:
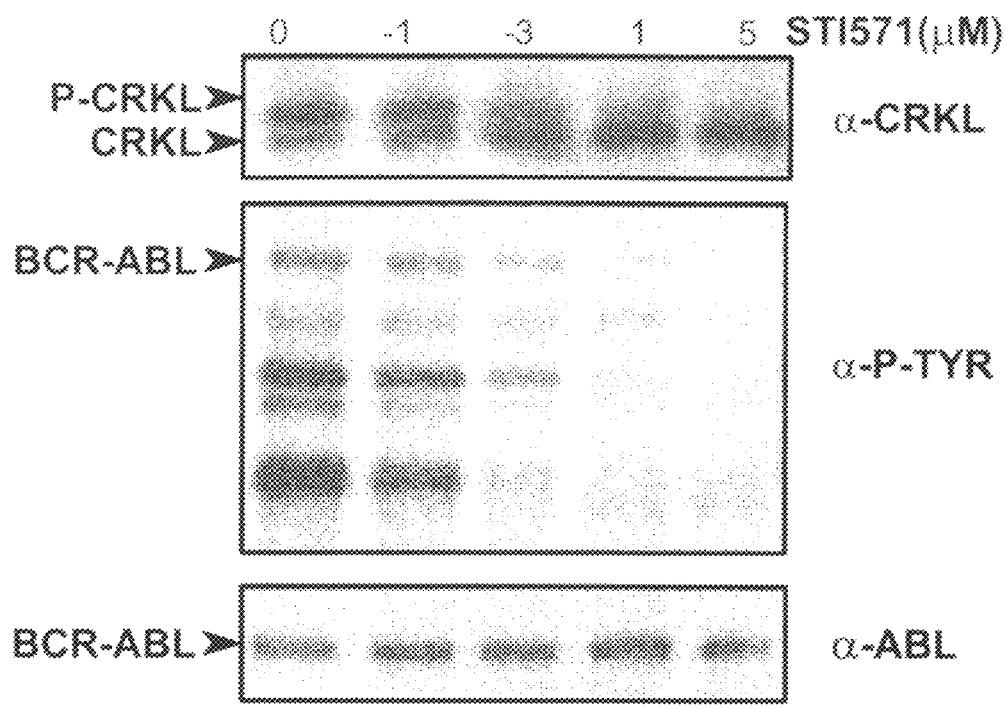
FIG. 1. Clinical relapse of STI-571-treated patients is associated with persistent Bcr-Abl kinase activity. (A) Immunoblot analyses of one CML patient's bone marrow cells after a 2-hour incubation with different concentrations of STI-571 in vitro. Whole cell lysates were separated by SDS-PAGE, transferred to nitrocellulose, and probed with Crkl (top panel), phosphotyrosine (middle panel), and Abl (bottom panel) antibodies. (B) Crkl immunoblot of whole cell lysates from CML patients prior to STI-571 therapy (left) and from Ph-positive blast crisis patients who achieved hematological remission (<5% blasts) on STI-571 but remained 100% BCR-ABL-positive (right). (C) Crkl immunoblots of whole cell lysates from lymphoid blast crisis or Ph-positive acute lymphoid leukemia patients (top panel) and myeloid blast crisis patients (middle panel) who relapsed after initially responding to STI-571 therapy. Phosphotyrosine immunoblot of patient cell lysates at time of relapse (bottom panel). Ph-positive cell line, K562, was used as a positive control for autophosphorylated Bcr-AbL (D) Crkl immunoblots of cell lysates from relapse patients taken prior to (pre-Tx) and during the course of (Tx and relapse) STI-571 therapy. Densitometric analyses of Crkl immunoblots (expressed as percentage of phosphorylated Crkl over total Crkl protein) are presented in bar graphs.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., 1989, Molecular Cloning: A Laboratory Manual, 2d ed., Cold Spring Harbor Laboratory Press, Cold Spring Harbor, N.Y. and Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

As used herein, the term "polynucleotide" means a polymeric form of nucleotides of at least about 10 bases or base pairs in length, either ribonucleotides or deoxynucleotides or a modified form of either type of nucleotide, and is meant to include single and double stranded forms of DNA.

As used herein, the term "polypeptide" means a polymer of at least about 6 amino acids. Throughout the specification, standard three letter or single letter designations for amino acids are used.

As used herein, a polynucleotide is said to be "isolated" when it is substantially separated from contaminant polynucleotides that correspond or are complementary to genes other than, for example, the MARS genes or that encode polypeptides other than MARS gene product or fragments thereof. As used herein, a polypeptide is said to be "isolated" when it is substantially separated from contaminant polypeptide that correspond to polypeptides other than the MARS polypeptides or fragments thereof. A skilled artisan can readily employ polynucleotide or polypeptide isolation procedures to obtain an isolated polynucleotides and polypeptides.

As used herein, the terms "hybridize", "hybridizing", "hybridizes" and the like, used in the context of polynucleotides, are meant to refer to conventional hybridization conditions, preferably such as hybridization in 50% formamide/ 6×SSC/0.1% SDS/100 µg/ml ssDNA, in which temperatures for hybridization are above 37 degrees C. and temperatures for washing in 0.1×SSC/0.1% SDS are above 55 degrees C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

"Moderately stringent conditions" may be identified as described by Sambrook et al., 1989, Molecular Cloning: A Laboratory Manual New York: Cold Spring Harbor Press, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

For purposes of shorthand designation of BCR-ABL variants described herein, it is noted that numbers refer to the amino acid residue position along the amino acid sequence of the BCR-ABL polypeptide. Amino acid identification uses the single-letter alphabet of amino acids, i.e.,

| Asp | D | Aspartic acid | Ile | I | Isoleucine |
|---|---|---|---|---|---|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | ASN | N | Asparagine |

In the context of amino acid sequence comparisons, the term "identity" is used to identify and express the percentage of amino acid residues at the same relative positions that are the same. Also in this context, the term "homology" is used to identify and express the percentage of amino acid residues at the same relative positions that are either identical or are similar, using the conserved amino acid criteria of BLAST analysis, as is generally understood in the art. For example, identity and homology values may be generated by WU-BLAST-2 (Altschul et al., Methods in Enzymology, 266: 460-480 (1996): http://blast.wustl/edu/blast/README-.html).

"Percent (%) amino acid sequence identity" with respect to the sequences identified herein is defined as the percentage of amino acid residues in a candidate sequence that are identical with the amino acid residues in the BCR-ABL sequence, after aligning the sequences and introducing gaps, if necessary, to achieve the maximum percent sequence identity. Alignment for purposes of determining percent amino acid sequence identity can be achieved in various ways that are within the skill in the art can determine appropriate parameters for measuring alignment, including assigning algorithms needed to achieve maximal alignment over the full-length sequences being compared. For purposes herein, percent amino acid identity values can also be obtained using the sequence comparison computer program, ALIGN-2, the source code of which has been filed with user documentation in the US Copyright Office, Washington, D.C., 20559, registered under the US Copyright Registration No. TXU510087. The ALIGN-2 program is publicly available through Genentech, Inc., South San Francisco, Calif. All sequence comparison parameters are set by the ALIGN-2 program and do not vary.

The terms "cancer", "cancerous", or "malignant" refer to or describe the physiological condition in mammals that is typically characterized by unregulated cell growth. Examples of cancer include but are not limited to, leukemia, lymphoma, blastoma, carcinoma and sarcoma. More particular examples of such cancers include chronic myeloid leukemia, acute lymphoblastic leukemia, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer.

The terms "treating", "treatment" and "therapy" as used herein refer to curative therapy, prophylactic therapy, and preventative therapy. The terms "individual selected for treatment" refer to an individual who has been identified as having a condition that artisans understand can respond to a specific therapy, and, consequentially is being considered for treatment (or being treated with) that therapy (e.g. an individual suffering from chronic myelogenous leukemia who is being treated with STI-571).

The term "mammal" as used herein refers to any mammal classified as a mammal, including humans, cows, horses, dogs and cats. In a preferred embodiment of the invention, the mammal is a human.

Additional definitions are provided throughout the subsections that follow.

The invention described herein relates to novel genes and their encoded proteins, termed Mutants Associated with Resistance to STI-571 (e.g., T315I Bcr-Abl), and to diagnostic and therapeutic methods and compositions useful in the management of various cancers that express MARS. Embodiments of the invention provided herein are illustrated by studies of the Bcr-Abl protein kinase in STI-571-treated patients. To characterize the mechanism of relapse in STI-571-treated patients, we first assessed the status of Bcr-Abl signaling in primary leukemia cells. As discussed in the Examples below, peripheral blood and/or bone marrow samples were obtained with appropriate informed consent from CML and Ph-positive ALL patients at UCLA who were enrolled in multicenter clinical trials of STI-571 sponsored by Novartis Pharmaceuticals. All patients had >30 percent blasts in the marrow prior to treatment. Responding patients had reduction in the percentage of bone marrow blasts to <15 percent (partial) or <5 percent (complete), as described in B. J. Druker et al., *N. Engl. J. Med.* 344, 1031 (2001). Progressive disease was defined as an increase in percentage of blasts after an initial response, despite continued STI-571 treatment. Mononuclear cells were isolated by centrifugation through Ficoll-Hypaque, washed twice in phosphate-buffered saline, counted and used immediately or cryopreserved.

A goal was to distinguish between Bcr-Abl dependent versus Bcr-Abl independent mechanisms of relapse. If Bcr-Abl remains critical for proliferation of the leukemia clone, then the Bcr-Abl signaling pathway should be reactivated. Alternatively, if expansion of the leukemia clone is independent of Bcr-Abl, then signaling through the Bcr-Abl pathway should remain impaired by STI-571. The most direct measure of signaling through Bcr-Abl pathway is the enzymatic activity of Bcr-Abl protein itself (see, e.g. J. B. Konopka et al., *Proc. Natl. Acad. Sci. U.S.A.* 82, 1810 (1985); S. S. Clark et al., *Science* 235, 85 (1987); and S. S. Clark et al., *Science* 239, 775 (1988)).

Although the enzymatic activity of Bcr-Abl protein is readily measured in cell lines, such assays are difficult to perform in a reproducible, quantitative fashion with clinical material because Bcr-Abl is subject to rapid degradation and dephosphorylation upon cell lysis. In a search for alternative measures of Bcr-Abl kinase activity, we found that the phosphotyrosine content of Crkl, an adaptor protein which is specifically and constitutively phosphorylated by Bcr-Abl in CML cells (see, e.g. J. ten Hoeve et al., *Blood* 84, 1731 (1994); T. Oda et al., *J. Biol. Chem.* 269, 22925 (1994); and G. L. Nichols et al., *Blood* 84, 2912 (1994)), could be measured reproducibly and quantitatively in clinical specimens (see Example 2 below). Crkl binds Bcr-Abl directly and plays a functional role in Bcr-Abl transformation by lining the kinase signal to downstream effector pathways (see, e.g. K. Senechal et al., *J. Biol. Chem.* 271, 23255 (1996)). When phosphorylated, Crkl migrates with altered mobility in SDS-PAGE gels and can be quantified using densitometry. As expected, Crkl phosphorylation in primary CML patient cells was inhibited in a dose-dependent manner when exposed to STI-571 and correlated with dephosphorylation of Bcr-Abl (FIG. 1A). This Crk1 assay allows for an assessment of the enzymatic activity of Bcr-Abl protein in a reproducible, quantitative fashion in clinical materials.

A recent preclinical study of STI-571 resistance in mice engrafted with a human blast crisis CML cell line demonstrated that al acid glycoprotein, an acute-phase reactant synthesized by the liver, can bind STI-571 in serum and block its activity against Bcr-Abl (see, e.g. C. Gambacorti-Passerini et al., *J. Natl. Cancer Inst.* 92, 1641 (2000)). This observation raises the possibility that STI-571 resistance in patients is due to a host-mediated response against the drug. Alternatively, resistance might be mediated by a cell-autonomous event in a leukemia subclone that allows escape from kinase inhibition by STI-571. To distinguish between these two possibilities, we determined the sensitivity of patient cells taken prior to treatment and at the time of relapse to STI-571 by measuring inhibition of Crkl phosphorylation. Briefly, purified cells were plated at 1–10×10$^6$/ml in RPMI-1640+10% human AB serum with varying concentrations of STI-571 for 24 hours. Proteins were extracted and subjected to immunoblot analysis.

Figures 2A, 2B:
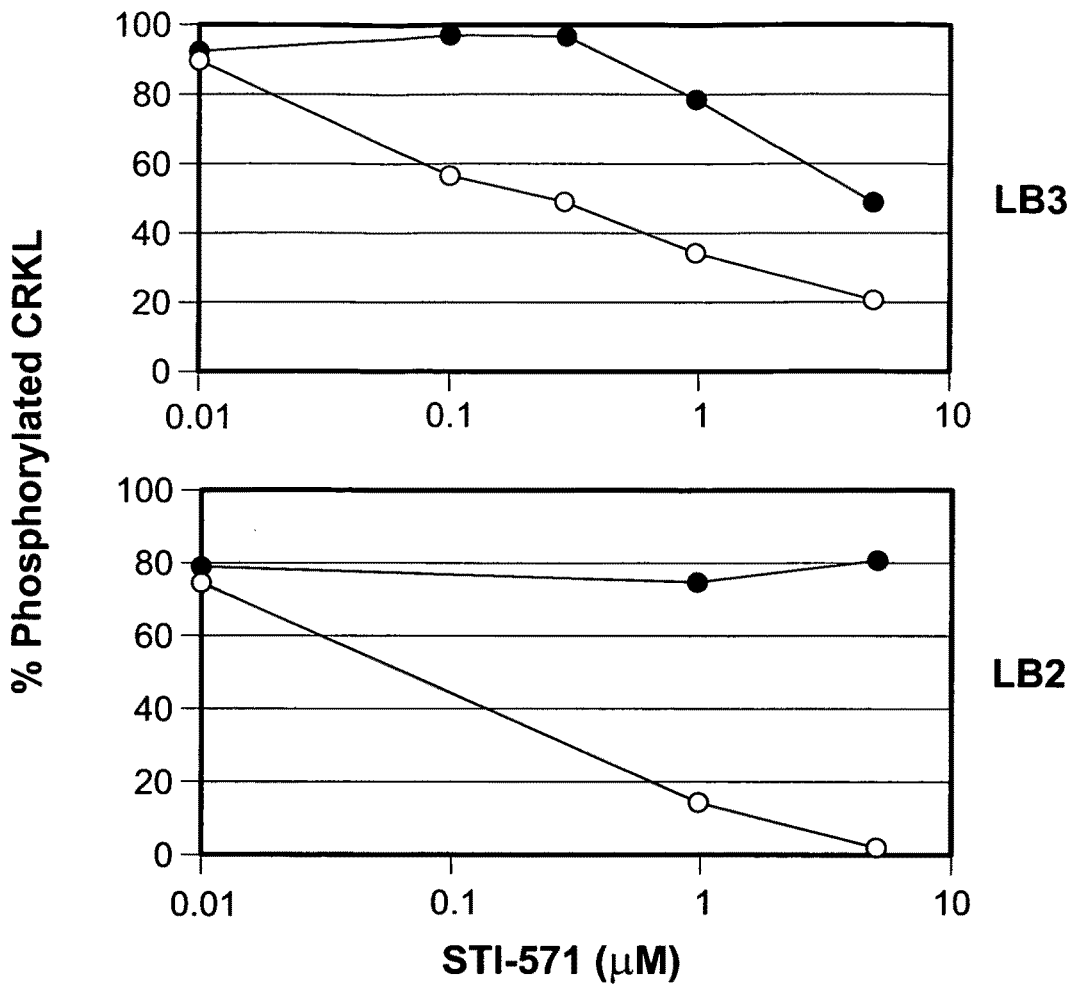
FIG. 2. Altered sensitivity of relapsed patient cells to STI-571. (A) STI-571 dose-response curves of Crkl phosphorylation in cells taken from blast crisis patients (LB3 and LB2) prior to STI-571 therapy (○) and at the time of relapse (●). Cells from both time points were exposed to increasing concentrations of STI-571, harvested, and analyzed by Crkl immunoblot and densitometry. (B) $IC_{50}$ values for inhibition of Crkl phosphorylation determined by exposure of cells isolated from untreated versus relapsed CML patients to increasing concentrations of STI-571, and subsequent Crkl immunoblot and densitometric analyses. Crkl phosphorylation in one relapsed patient sample (LB2) could not be inhibited with high concentrations of STI-571. ($IC_{50}$=concentration of STI-571 required to reduce CRKL phosphorylation by 50%).

If STI-571 resistance is a consequence of a host response, pretreatment and relapse leukemia cells should be equally sensitive to ex vivo STI-571 treatment. However, if STI-571 is cell-intrinsic, leukemia cells obtained at relapse should be less sensitive to STI-571 than pretreatment cells. In those patients for whom we had sufficient matched clinical material, a 10-fold or greater shift in sensitivity to STI-571 was observed at relapse (FIG. 2A). Aggregate analysis of 11 samples confirmed that higher concentrations of STI-571 are required to inhibit Crkl phosphorylation in patients cells obtained at relapse versus pre-treatment (FIG. 2B).

Since these ex vivo studies provide evidence that STI-571 resistance is cell-intrinsic, we considered several possible mechanisms. Some CML cell lines that develop resistance to STI-571 after months of in vitro growth in sub-therapeutic doses of the drug have amplification of the BCR-ABL gene (see, e.g. E. Weisberg et al., *Blood* 95, 3498 (2000); P. le Coutre et al., *Blood* 95, 1758 (2000); and F. X. Mahon et al., *Blood* 96, 1070 (2000)). We performed dual-color fluorescence in situ hybridization (FISH) experiments to show that BCR-ABL gene amplification is similarly implicated in STI-571 resistance in human clinical samples (see Example 3 below).

Figure 4A:
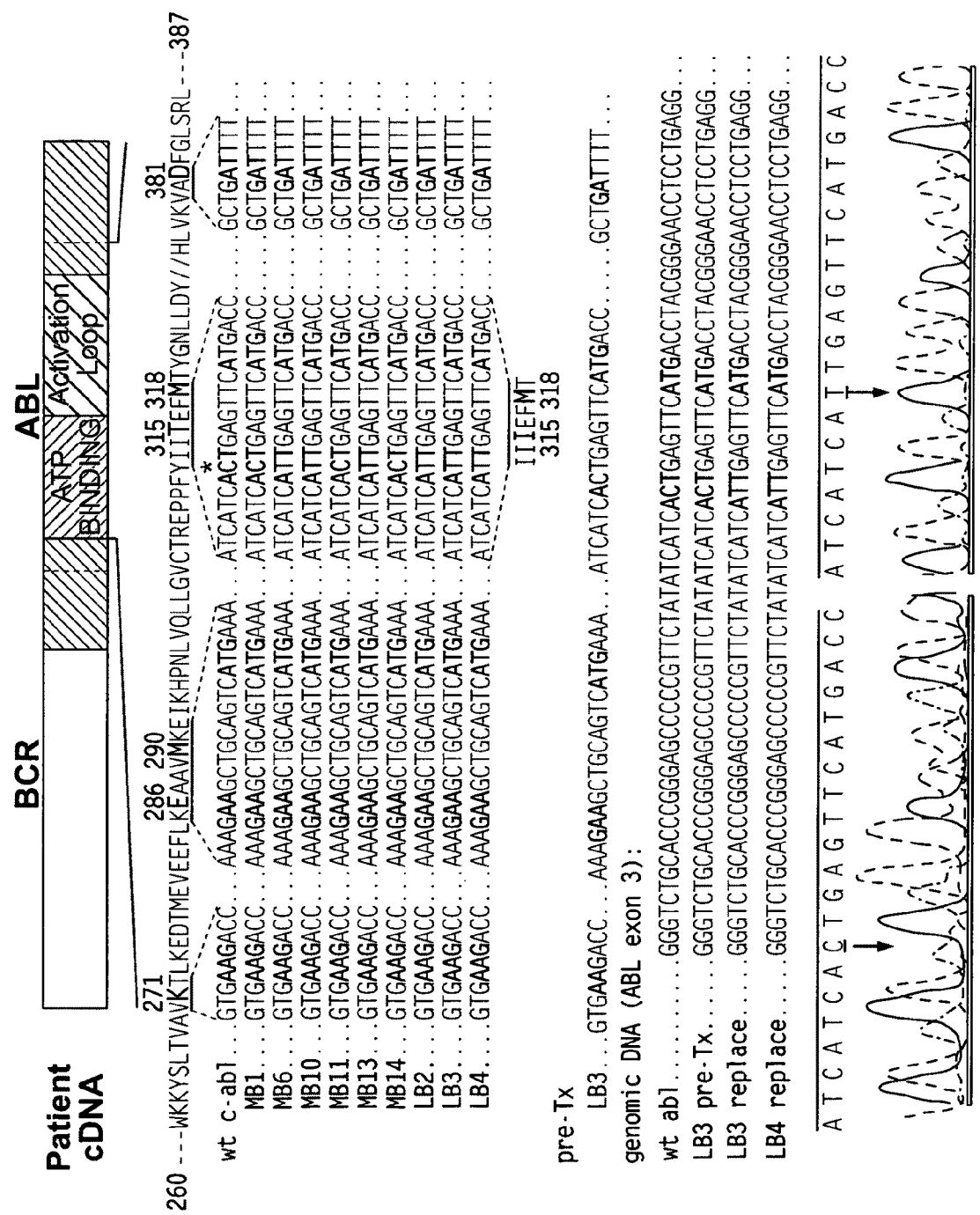
FIG. 4. Point mutation in the ATP-binding pocket of the Abl kinase domain confers STI-571 resistance in relapsed patients. (A) Schematic of PCR strategy to determine the sequence of a 578 base pair region of BCR-ABL that corresponds to the ATP-binding pocket and activation loop of the kinase domain in patient samples. Amino acid sequence of the region of Abl analyzed is shown in black (SEQ ID NO: 12). Residues predicted to form hydrogen bonds with STI-571, based on crystal structure data, are in boldface and are numbered from the first amino acid of c-Abl (GenBank accession number: M14752, shown in Table II) (SEQ ID NO: 1). Corresponding nucleotide sequence (shown in red) was aligned with sequences obtained from nine patient cDNAs (first column discloses SEQ ID NO: 13, second column discloses SEQ ID NO: 14, third columns discloses SEQ ID NOS 15, 15, 17, 17, 15, 17, 15, 17, 17 and 17, respectively, in order of appearance, and fourth column discloses SEQ ID NO: 16; "pre-Tx" disclosed as SEQ ID NOS 13-16, respectively, in order of appearance). The C→T mutation at ABL nucleotide 944 (detected in six patients at relapse and in no pre-treatment samples) is shown in blue. Sequence of wild-type ABL exon 3 (GenBank accession number: NT008338.2) (SEQ ID NO: 18) was aligned with sequences obtained from patient genomic DNA (SEQ ID NOS 18, 19 and 19, respectively, in order of appearance) prior to treatment and at relapse. Examples of primary sequence data (represented as chromatographs) from wild-type BCR-ABL (left) (SEQ ID NO: 15) and BCR-ABL with the C→T point mutation (right) (SEQ ID NO: 17). (B) Model of STI-571-binding pocket of wild-type Abl in complex with STI-571 (left panel) and predicted structure of STI-571-binding pocket of T315I mutant Abl in complex with STI-571 (right panel). In the molecular structures representing STI-571 and Abl residue 315, nitrogen atoms are shown in blue and oxygen atoms are shown in red. Van-der-Waals interactions are depicted in grey for STI-571 (both panels), in blue for wild-type Abl residue $Thr^{315}$ (left panel), and in red for mutant Abl residue $Ile^{315}$ (right panel). Polypeptide backbone of the Abl kinase domain is represented in green. (C) Immunoblots of whole cell lysates isolated from transfected 293T cells (wild-type p210 BCR-ABL shown in left panels and T315I mutant shown in right panels) after a 2-hour incubation with different concentrations of STI-571. Blots were probed with phosphotyrosine (top panels) and Abl (bottom panels) antibodies.

Through the disclosure, data from various groups of patients is discussed. Tables IA-IF provide a summary of patient data. As illustrated in Example 1 below, we also considered the possibility that mutations in BCR-ABL might confer resistance to STI-571. Consequently, a 579 base pair region corresponding to the ATP-binding pocket and the activation loop of the kinase domain of Bcr-Abl was sequenced in the 9 patients for whom RNA was available at the time of relapse (FIG. 4A). A single, identical C→T nucleotide change was detected at ABL nucleotide 944 in six of nine cases examined (FIG. 4A). In all six patients a mixture of wild-type and mutant cDNA clones were found, with the frequency of mutant clones ranging from 17% to 70%. The mutation was found in three of three patients with lymphoid disease and in three of six patients with myeloid blast crisis. The presence of the mutation was confirmed by analysis of genomic DNA (FIG. 4A).

Figure 4B:
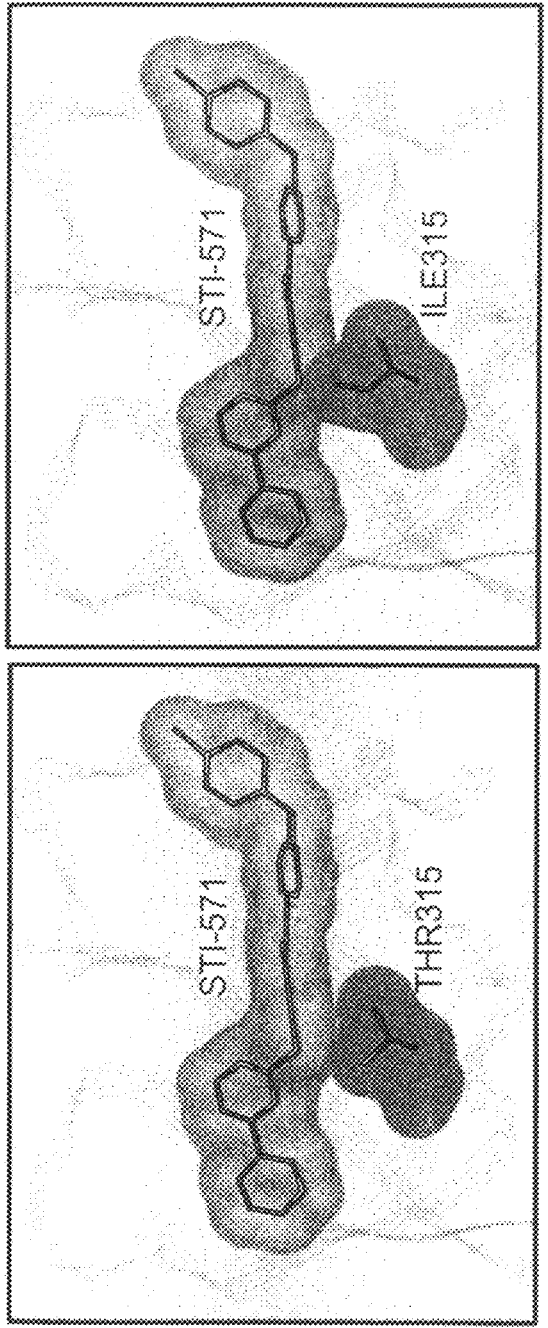

In the MARS designated T315I Bcr-Abl, a single nucleotide C→T change results in a threonine to isoleucine substitution at position 315 of c-Abl. The recently-solved crystal structure of the catalytic domain of Abl complexed with a variant of STI-571 identified the amino acid residues within the ATP-binding site and activation loop of c-Abl that are required for STI-571 binding and thus inhibition of Abl kinase activity (see, e.g. T. Schindler et al., *Science* 289, 1938 (2000)). Thr$^{315}$ is among those that form critical hydrogen bonds with STI-571. The potential consequence of the T315I substitution on the STI-571 binding pocket was modeled based on the crystal structure of the wild-type Abl kinase domain in complex with STI-571 (FIG. 4B). The absence of the oxygen atom normally provided by the side chain of Thr$^{315}$ would preclude formation of a hydrogen bond with the secondary amino group of STI-571. In addition, isoleucine contains an extra hydrocarbon group in the side chain, which would result in steric clash with STI-571 and presumably inhibit binding. Notably, the model predicts that the T315I mutation should not interfere with ATP binding. The structure of the kinase domain of Hck in complex with an ATP analog (AMP-PNP) was superimposed onto the model of the Ile315 Abl kinase domain.

T315I Bcr-Abl is discussed as a representative embodiment of the MARS disclosed herein (e.g. those described in Table IA below). In certain descriptions of the invention provided herein, embodiments of a single gene are used (T315I Bcr-Abl, for example) to illustrate typical embodiments of the invention that apply to all of the MARS disclosed herein (e.g. E255K, Q252H, V304D, M351T, E355G etc. as shown in Table I) In this context, artisans understand that discussing a typical embodiment directed to a single species (e.g. T315I) when the embodiments are commonly applicable to the other species disclosed herein (e.g. E255K, Q252H, V304D, M351T, E355G etc.) eliminates unnecessary redundancy in the descriptions of the invention.

The T315I mutation is shown to preserve kinase activity and, based upon the crystal structure of the kinase domain when bound to STI-571, is predicted to result in ineffective binding of STI-571 to BCR/ABL. In an effort to define the full spectrum of kinase domain mutations in a larger sample size, we sequenced the BCR/ABL kinase domain in 18 patients with CML in myeloid blast crisis. In 13 patients, samples obtained at the time of relapse after a partial or complete response to STI-571 (acquired resistance) were analyzed. In 5 patients who did not respond to STI-571 (de novo resistance), analysis was performed on samples obtained prior to treatment. To ensure detection of subclones with kinase domain mutations that might account for a minority of BCR/ABL expressing cells in the blood, we typically sequenced ten independent clones from each patient sample. A mutation was considered present only if it was detected by sequencing of both cDNA strands. The previously identified T315I mutation was found in 3 additional patients.

In conjunction with our preliminary analysis of 11 patients (Gorre et al., 2001, Science, August 3; 293(5531):876-80), the T315I mutation has also been detected in subsequent studies of 9 of 28 patients (6/25 myeloid blast crisis, 3/3 with lymphoid blast crisis or Ph+ ALL). Two other mutations, M351T and E255K, were also found in 4 patients and 3 patients respectively. Additional mutations were also found but did not always represent the dominant subclone at time of relapse. These findings indicate that BCR/ABL kinase domain mutations occur commonly in CML blast crisis and can be detected, in some cases, prior to STI-571 treatment. These mutations may be a reflection of genetic instability associated with disease progression or, possibly, prior treatment exposure. Following the protocols used to examine the T315I mutation, which we have previously shown to cause in term resistance to STI-571, the significance of these additional mutations in STI-571 drug resistance can be defined.

Figure 4C:
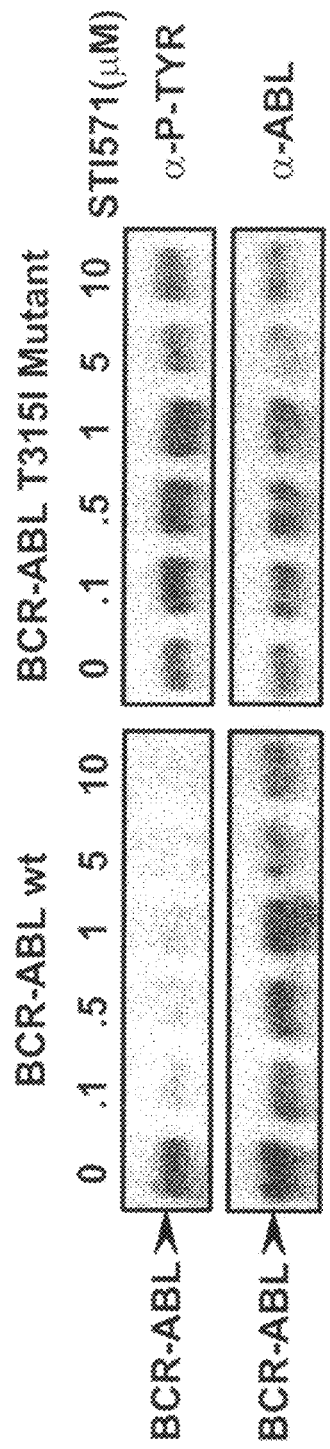
Figure 5:
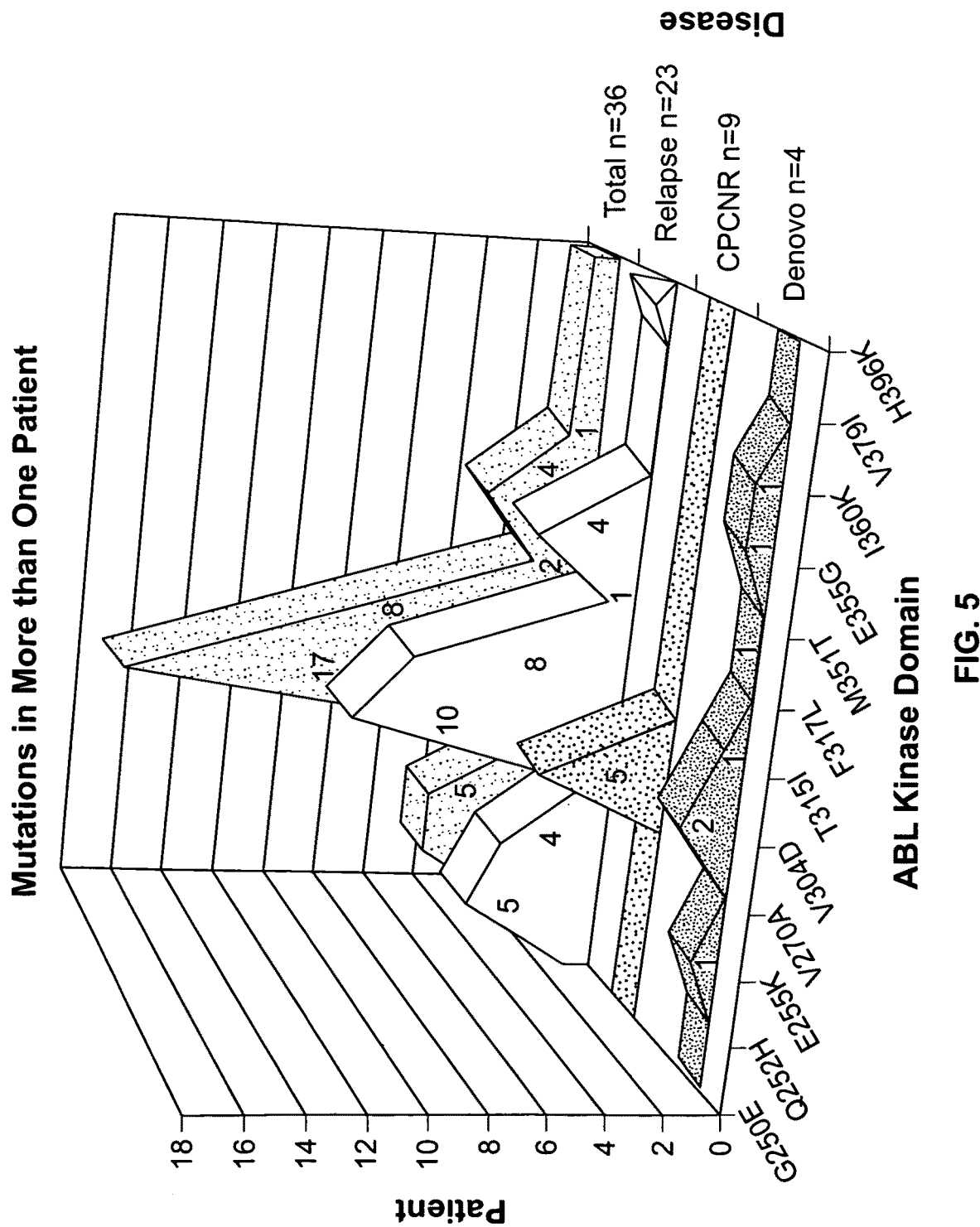
FIG. 5. Graphic schematic of mutations in more than one patient.

To confirm that this amino acid substitution interferes with STI-571 activity, we engineered the T315I mutation into wild-type p210 Bcr-Abl (see, e.g. Full-length p210 Bcr-Abl was subcloned into the pSRaMSVtkNeo retrovirus vector (see, e.g. A. J. Muller et al., *Mol. Cell Biol.* 11, 1785 (1991)). A fragment containing the C to T mutation at ABL nucleotide 944 was made by PCR and swapped with the corresponding sequence in pSRaMSVtkNeo p210 Bcr-Abl wild-type to create the pSRaMSVtkNeo p210 Bcr-Abl T315I mutant. The resulting construct was confirmed by sequencing. Cells were transfected with wild-type or T315I p210 Bcr-Abl and cultured in the presence of increasing concentrations of STI-571. Briefly, the transient transfection of 293T cells was performed using $CaCl_2$ (see, e.g. A. J. Muller et al., *Mol. Cell. Biol.* 11, 1785 (1991)). After a 24-hour transfection, cells were incubated with varying concentrations of STI-571 (provided by Novartis Pharmaceuticals, Basel, Switzerland) for 2 hours. Proteins were extracted and subjected to immunoblot analysis. As shown by Abl immunoblot analysis, the expression of wild-type and T315I mutant Bcr-Abl proteins was similar, and was not changed by STI-571 (FIG. 4C, bottom panels). Based on anti-phosphotyrosine immunoblot analysis, the kinase activities of wild-type Bcr-Abl and the T315I mutant appear comparable in the absence of STI-571. Whereas wild-type Bcr-Abl kinase activity was inhibited by STI-571, the T315I mutant retained high levels of phosphotyrosine at all concentrations of inhibitor tested (FIG. 4C, top panels).

In summary, our preliminary analysis of 11 patients with advanced stage CML who underwent disease progression after an initial response to STI-571 shows that reactivation of Bcr-Abl signaling occurred in all patients, despite continued STI-571 treatment. Therefore, the primary explanation for disease progression in these patients appears to be Bcr-Abl dependent proliferation rather than secondary oncogenic signals that permit Bcr-Abl independent growth. It is possible that studies of a larger number of patients may identify exceptions to this theme, as has been reported in transgenic mice expressing conditional oncogenes where an occasional tumor can escape dependence on the initiating oncogene (see, e.g. L. Chin et al., *Nature* 400, 468 (1999); D. W. Felsher et al., *Mol. Cell.* 4, 199 (1999); and C. S. Huettner et al., *Nature Genet.* 24, 57 (2000)). In the majority of patients we studied, the mechanism of resistance is a consequence of mutation or amplification of the target oncogene BCR-ABL (one patient had both events). These results provide evidence in a genetically complex human cancer that a single molecular target remains relevant in late stage, relapsed disease.

Interestingly for example, the identity of the Abl kinase domain mutation found in these patients bears remarkable similarity to a threonine to isoleucine change in v-Src versus c-Src at position 338, which corresponds to $Thr^{315}$ in c-Abl. Despite the fact that v-Src and c-Src have almost identical kinase domain sequences (98% identity), v-Src is approximately 50-fold more resistant than c-Src to kinase inhibition by the Src inhibitor PP1 (see, e.g. Y. Liu et. al., *Chem. Biol.* 6, 671 (1999).

Eleven Patients described in our preliminary study obtained complete hematologic remissions and, in some cases, complete cytogenetic remissions on STI-571, then relapsed within two to six months. This clinical scenario must be distinguished from those of patients who obtain only partial responses to STI-571 or fail to respond at all. In a phase II trial of 260 patients treated with STI-571 in myeloid blast crisis, only about 20% of patients fell into the former group. Therefore, the 11 patients described in our study represented a highly select population. This distinction is important, because patients with partial hematologic responses and no cytogenetic response will have a substantial number of mature BCR-ABL expressing hematopoietic cells that persist during treatment and are not representative of the relapsing, drug-resistant subclone. Since the current protocols for mutation detection do not specifically isolate relapsing, drug-resistant cells from other BCR-ABL ex-pressing blood cells, failure to detect a mutation might be explained by an insensitive assay. In contrast, the dominant population of BCR-ABL expressing cells in patients who relapse after a cytogenetic response will, by definition, be representative of the resistant subclone. Indeed, we found the T315I mutation in more than 80% of BCR-ABL expressing cells from three such patients.

With respect to methodology, we subcloned our PCR products rather than perform direct sequencing, and we sequenced at least 10 independent clones per patient. All mutations required confirmation by sequencing in both directions. We chose this strategy to maximize our sensitivity of detecting mutations that may be present in a minority of BCR-ABL-expressing cells. In addition, this method provided a rough quantitative estimate of the fraction of BCR-ABL-expressing cells that contained the mutation, so that clonal evolution could be monitored over time. In retrospect, this method allowed us to find the T315I mutation in several patients in whom the resistant clone represented less than 20% of the BCR-ABL-expressing cells.

Although the development of STI-571 resistance presents new therapeutic challenges, the fact that Bcr-Abl remains active in STI-571-resistant cells provides evidence that the chimeric oncoprotein remains a rational drug target. Because a significant fraction of the patients examined to date share an identical mutation associated with drug resistance, it may be possible to identify an inhibitor of the mutant BCR-ABL allele that would have broad utility. In addition, knowledge of this mutation provides for the development of a wide variety of assays to evaluate this mutation, for example to detect drug resistant clones prior to clinical relapse. See, e.g. B. J. Druker et al., *N. Engl. J. Med.* 344, 1038 (2001); A. Goga et al., *Cell* 82, 981 (1995); E. Abruzzese et al., *Cancer Genet. Cytogenet.* 105, 164 (1998); J. D. Thompson et al., *Nucleic. Acids Res.* 25, 4876 (1997); A. J. Muller et al., *Mol. Cell. Biol.* 11, 1785 (1991).

As noted herein, analysis has revealed that STI-571 resistance can occur through at least two distinct mechanisms. Some patients develop chromosomal amplification of the genomic region encoding Bcr-Abl, resulting presumably in levels of Bcr-Abl protein that overcome the intracellular concentration of STI-571 (Gorre et al., *Science* 293:876-880 (2001)). A second mechanism involves point mutations in the kinase domain that presumably interfere with drug-protein binding without compromising kinase activity. The best characterized of these involves a substitution of isoleucine for threonine at amino acid position 315 (T315I) which alters the shape of the drug-binding pocket based on a crystallographic-based model (Gorre et al., *Science* 293:876-880 (2001)). A limited number of other mutations within the kinase domain has been reported at frequencies ranging from two of 44 cases (Barthe et al., *Science* 293:2163 (2001); Hochhaus et al., *Science* 293:2163 (2001)) to seven of eight in cases of acquired resistance (Von Bubnoff et al., *Lancet* 359:487-491 (2001); *Lancet* 359:487-491 (2001)). The result of one small study revealed no detectable mutations in a single patient with accelerated phase CML at the time of relapse, but found unique mutations, including E255K in each of five patients with Philadelphia chromosome-positive acute lymphoblastic leukemia (ALL), as well as in one patient with CML in lymphoid blast crisis (Von Bubnoff et al., *Lancet* 359:487-491 (2001)). A separate study also focused upon Philadelphia chromosome-positive ALL and detected E255K in six of nine patients at the time of relapse, as well as T315I in one of nine patients (Hofmann et al., *Blood* 99:1860-1862 (2002)). Most recently, results from a heterogenous group of patients revealed the presence of Bcr-Abl kinase domain mutations in two of four cases of relapsed myeloid blast crisis (one patient was found to harbor T315I, and the second revealed evidence of a novel mutation, G250E), and in two of seven patients with chronic phase disease who suffered progressive disease after initial hematologic response. Evidence of new mutations G250E, F317L, and M351T was presented, but no biologic or biochemical assays were reported (Branford et al., *Blood* 99:3472-3475 (2002)).

Given the reliance of leukemic cells upon Bcr-Abl activity at the time of STI-571 resistance, efforts to overcome STI-571 resistance must be equipped to deal with the most common mechanisms of resistance. Other investigators have reported widely varying frequencies of kinase domain mutations using methodology that involved direct sequencing of cDNA, which represents a consensus of sequences presence at the time of relapse. We sought to define the full spectrum of Bcr-Abl kinase domain mutations in cases of resistance using methods of mutation detection with superior sensitivity. Here we report our sequence analyses of the Bcr-Abl kinase domain in patients treated with STI-571. These include cases of acquired resistance of myeloid blast crisis phase, cases of myeloid blast crisis exhibiting de novo resistance, cases of lymphoid blast crisis, and cases of chronic phase cytogenetic refractoriness/relapse. We found evidence of Bcr-Abl kinase domain mutations in nearly all cases of acquired resistance.

Analysis of a subgroup of the more common mutations provides evidence that these mutant isoforms retain the biologic activity of Bcr-Abl but exhibit varying degrees of resistance to STI-571 in both biochemical and biological assays. Kinase domain point mutations apparently represent a common mechanism through which resistance to STI-571 is acquired. Additionally, we provide the first evidence of polyclonal resistance to STI-571 in individual patients. Efforts to target Bcr-Abl in the setting of STI-571-resistance will need to address the activities of the numerous mutant Bcr-Abl isoforms. Medical management of CML patients receiving targeted therapy will likely be facilitated by routine periodic assessment for kinase domain mutations. Lastly, we provide evidence for pre-existing kinase domain mutations in a small number of patients with STI-571-refractory myeloid blast crisis prior to institution of therapy, suggesting that the evolution of chronic phase CML to blast crisis CML may be, in some cases, facilitated by the accumulation of activating Bcr-Abl kinase domain mutations. Human malignancies, even those believed to rely upon a very small number of genetic alterations, likely comprise a significantly heterogeneous population of cells, and the developing field of targeted therapy of malignancy appears to face daunting obstacles.

In an effort to define the true incidence and full spectrum of kinase domain mutations that are capable of causing resistance in cases of myeloid blast crisis, we performed sensitive sequence analysis of the Bcr-Abl kinase domain in patients whose disease relapsed after an initial response to STI-571 treatment ("acquired resistance"). We identified different mutations in patients with relapsed myeloid blast crisis in the vast majority of cases evaluated. Evidence of mutation was found in all four of the variable P-loop consensus (Gly-X-Gly-X-X-Gly-X-Val) amino acids (SEQ ID NO: 21). Mutations were found as far as 140 amino acids away from the P-loop, and could be grouped by location into categories. Moreover, we provide evidence that resistance frequently involves a polyclonal expansion of Bcr-Abl expressing cells.

In vitro analysis of a subset of kinase domain mutations demonstrated varying degrees of STI-571 resistance relative to wild-type Bcr-Abl. We also analyzed the Bcr-Abl kinase domain in patients with chronic phase CML who had no cytogenetic response to STI-571 and found evidence of kinase domain mutations in a number of cases analyzed. A subset of these kinase domain mutations were identical to those seen in relapsed myeloid blast crisis cases. Significantly, the presence of kinase domain mutation in this setting strongly correlated with disease progression and decreased overall survival. Lastly, we found evidence of STI-571-resistant kinase domain mutations prior to STI-571 treatment in a subset of patients with myeloid blast crisis who subsequently failed to respond to STI-571.

Multiple mutations in the Bcr-Abl kinase domain can be detected at the time of resistance in cases of myeloid blast crisis. Cytogenetic analysis of patients with myeloid blast crisis whose disease initially responded to STI-571 revealed persistence of the Philadelphia chromosome in nearly 100 percent. We envisioned the possibility of resistant clones emerging from this population of Bcr-Abl containing cells, and therefore likely comprising a subset of the Philadelphia chromosome-containing cells at the time of relapse. By sequencing ten independent PCR products per patient sample and requiring two independent isolates of a given mutation, we detect mutations that comprise as few as twenty percent of the population of Bcr-Abl sequences. Sequence analysis of the Bcr-Abl kinase domain revealed evidence of point mutations in sixteen of seventeen cases of relapsed myeloid blast crisis (MBC) CML at the time of relapse (see Table IV). The previously identified T315I mutation was detected. E255K, which has been previously described (Von Bubnoff et al., Lancet 359:487-491 (2001); Hofmann et al., Blood 99:1860-1862 (2002); Branford et al., Blood 99:3472-3475 (2002)), was also detected. M351T was also recently reported (Branford et al., Blood 99:3472-3475 (2002)) and was also detected. The novel mutation Q252H as well as the recently reported G250E (Branford et al., Blood 99:3472-3475 (2002)) were found at the time of relapse. Patients had one of two alternative substitutions at position Y253; including mutations which substituted histidine for tyrosine (Y253H), as previously described (Von Bubnoff et al., Lancet 359:487-491 (2001); Branford et al., Blood 99:3472-3475 (2002)). Interestingly, a novel conversion of tyrosine to phenylalanine (Y253F) was also observed. Phenylalanine is highly conserved at this position in the Src-family of tyrosine kinases, and when engineered in to c-Abl, this mutation has been demonstrated to impart oncogenicity as reflected by cellular transformation assays (Allen et al., J Biol Chem 275:19585-19591 (1996)). We have recently found the sensitivity of Y253F to STI-571 to be intermediate between wild-type Bcr-Abl and the T315I mutant. Patients exhibited mutations within the activation loop at position H396, involving substitution to either proline or arginine. Interestingly, several tyrosine kinases, including Hck, c-Src, v-src, lck, and Fyn all have an arginine at this position. Unique examples of the novel mutations V304D, E355G, and F359V, as well as the recently reported F317L (Branford et al., Blood 99:3472-3475 (2002)) were each observed. Using our method of detection analysis, we were able to detect Bcr-Abl kinase domain mutations in the vast majority of samples obtained from patients with relapsed myeloid blast crisis, including a number of novel mutations.

In addition to offering greater sensitivity of mutation detection, our methodology afforded the ability to assess for polyclonal resistance to STI-571, i.e. the presence of more than one resistant clone in a given patient. Indeed, a significant percentage of patients with myeloid blast crisis exhibiting acquired resistance to STI-571 were found to harbor more than one independent mutation. Samples obtained prior to treatment in cases of acquired resistance exhibited no evidence of mutation.

To address whether the surprisingly high frequency and variety of kinase domain mutations represented artifact introduced during the PCR amplification process, we sequenced ten independent subclones of the Abl kinase domain obtained from each of two healthy blood donors. Using our criteria of at least two independent isolates out of ten clones, we found no evidence of Abl kinase domain mutation. We therefore conclude that the Bcr-Abl kinase domain mutations described here are highly unlikely to be the result of PCR-introduced error, and most probably represent accurate reflections of kinase domain sequence heterogeneity in these STI-571-resistant patients.

Imatinib-resistant cases of lymphoid blast crisis reveal kinase domain mutations similar to myeloid blast crisis. Analysis of samples obtained from four of five patients with lymphoid blast crisis (LBC) at the time of relapse revealed the presence of Bcr-Abl kinase domain mutations. Again, clear evidence for polyclonal resistance was observed, with the coexistence of four separate mutations (Y253F, E255K, T315I, and M351T) in a single patient. Another patient harbored both E255K and Y253F. Two additional patients were found to harbor T315I in the absence of any other mutations.

Bcr-Abl kinase domain mutations can be detected in chronic phase patients who fail to achieve cytogenetic remission or lose an established major cytogenetic response and are associated with disease progression and decreased survival. Cells from chronic phase patients who failed to obtain cytogenetic remission or who lost a previously achieved cytogenetic remission were subjected to sequence analysis of the Bcr-Abl kinase domain. Analysis was performed on samples obtained at the time of sustained hematologic response. A number of patients were found to harbor mutations. Three of these mutations were also observed in cases of relapsed myeloid blast crisis described above (E255K, F317L, F359V). F317L was recently described in a single patient (Branford et al., Blood 99:3472-3475 (2002)) with chronic phase disease and cytogenetic persistence who subsequently suffered progressive disease. The last mutation, V379I, has not been documented in any other patient to date. Of the patients we studied, four have suffered progressive disease and have since discontinued STI-571. Among these, three have died and the fourth is living following subsequent allogeneic stem cell transplantation. Three of these four patients had Bcr-Abl kinase domain mutations (E255K, F317L, F359V) while one had no evidence of mutation. The patient harboring the V379I mutation continues to have a complete hematologic remission in response to STI-571 in the absence of a cytogenetic response. We conclude that kinase domain mutations occur in chronic phase patients who lose cytogenetic or hematologic responses to STI-571, and in a subset of chronic phase patients who have persistence of the Philadelphia chromosome in the setting of complete hematologic response.

Bcr-Abl kinase domain mutations can be detected prior to STI-571 treatment in patients with myeloid blast crisis that exhibit de novo resistance, but not in patients with STI-571-sensitive myeloid blast crisis or chronic phase CML. To determine whether Bcr-Abl kinase domain mutations may play a role in de novo resistance to STI-571, we analyzed pre-treatment samples from four patients with MBC who failed to achieve even a transient response to STI-571. One patient exhibited T315I prior to initiation of therapy. Also detected in the same patient was a Bcr-Abl allele that contained two mutations, M343T and F382L. A second patient had the E255K mutation prior to STI-571 treatment.

Bcr-Abl kinase domain mutations retain catalytic activity, and are capable of conferring STI-571 resistance in vitro. To assess whether the novel mutations observed were capable of conferring resistance to STI-571 in vitro, we performed site-directed mutagenesis of Bcr-Abl in a retroviral expression plasmid. In an illustrative embodiment of the invention, eight of the observed mutations (G250E, Q252H, Y253F, E255K, T315I, F317L, M351T, and E355G) were independently introduced into pSRalphaP210Bcr-Abl. While these mutants are provided as preferred embodiments of the invention described herein, those skilled in the art can generate comparable mutants of any one of the MARS described herein such as those identified in Table I.

Figure 9:
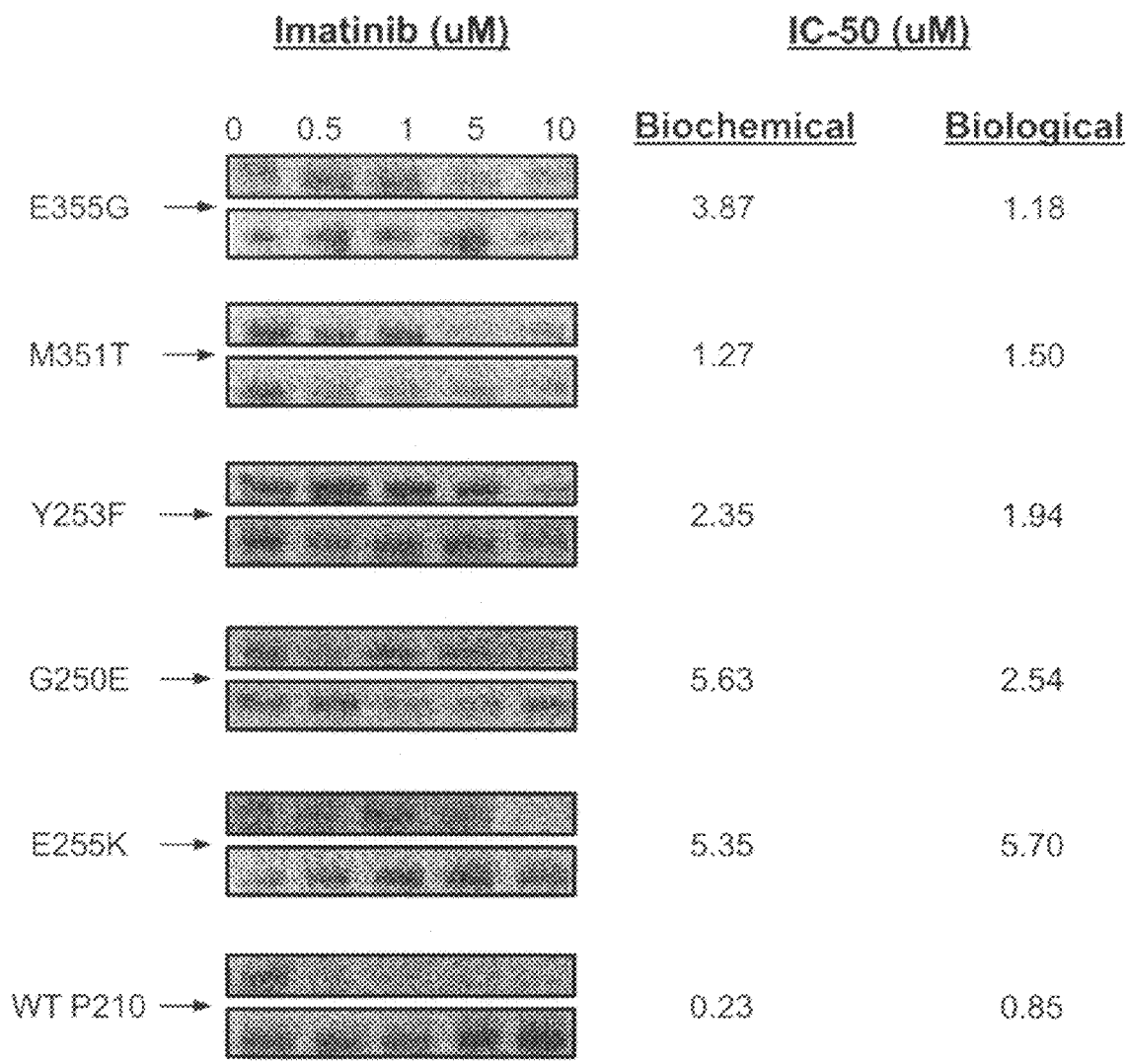
FIG. 9. Bcr-Abl kinase domain mutants exhibit varying degrees of biochemical and biologic resistance to STI-571. Western blot using an anti-phosphotyrosine antibody (4G10) of lysates prepared from Ba/F3 populations infected with retroviruses expressing the Bcr-Abl isoforms indicated and grown in the absence of IL-3 were exposed to varying concentrations of STI-571 for two hours are shown. Biochemical IC-50s for each of the mutations is shown. Biologic IC-50s were determined by viable cell count of cells after 48 hours of STI-571 exposure.
Figure 11:
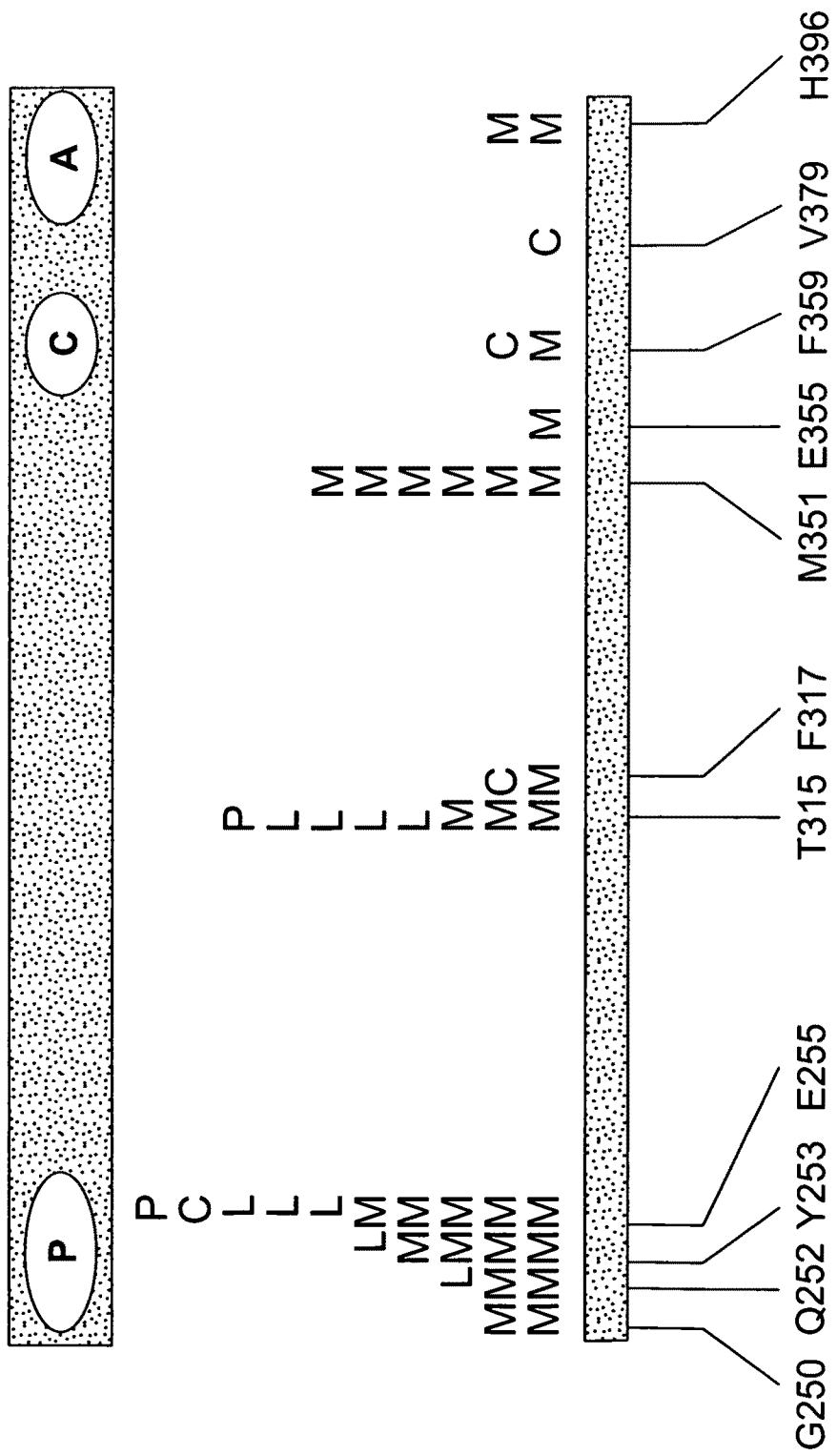
FIG. 11. Summary of STI-571-resistant Bcr-Abl kinase domain mutations. Each letter represents a patient with in whom the corresponding mutation was detected. Chronic phase patients are represented by the letter "C." Relapsed myeloid blast crisis patients are indicated by the letter "M." Patients with relapsed lymphoid blast crisis are represented by the letter "L." "R" indicates mutations prior to STI-571 treatment in patients with myeloid blast crisis who were refractory to treatment. Note that kinase domain is not drawn to scale.

Successful introduction of the expected mutations was confirmed by sequence analysis of the kinase domain. The eight mutations were each transiently transfected into 293-T cells, and found to exhibit varying degrees of sensitivity to STI-571, with IC-50 for enzymatic inhibition in cells ranging from 1.27 uM to 5.63 uM as documented by phosphotyrosine-containing Bcr-Abl (see FIG. 9). The murine hematopoietic cell line Ba/F3 requires exogenous IL-3 in the absence of Bcr-Abl. Stable Ba/F3 cell lines, capable of growing in the absence of interleukin-3, were derived for each of the eight mutant isoforms, demonstrating that each of the eight mutant isoforms retains biologic activity in this assay. The effect of varying concentrations of STI-571 on cellular viability after 48 hours was determined. Again, the eight mutant isoforms were found to exhibit varying degrees of sensitivity to STI-571. Several of the mutants appeared to impart only moderate resistance, retaining sensitivity to concentrations of STI-571 which are theoretically achievable in patients (see FIG. 9).

Analysis of cells containing kinase domain mutations reveals no evidence of point mutation in Bcr-Abl immediately sequences 5' to the kinase domain or in the tyrosine kinase domain of c-Kit. Genomic instability during advanced phase CML has been previously described. The high frequency of kinase domain mutations observed in our study, in addition to the finding of subpopulations of different mutations in individual patients, could theoretically be a reflection of a global decrease in DNA mismatch repair, or alternatively, may reflect a strong selection for these isoforms in the presence of STI-571. In an effort to address this issue, sequencing of a 700 bp fragment of Bcr-Abl immediately 5' to the kinase domain was performed in five patients in whom several kinase domain mutations were detected. No evidence of additional mutation was found in these samples. We also assessed the kinase domain of the related tyrosine kinase c-Kit, which resides on chromosome 4 and exhibits sensitivity to STI-571 at concentrations equivalent to Bcr-Abl, in the same group of five patients. No evidence of c-Kit kinase domain mutation was detected, arguing against the possibility of widespread genomic instability. We hypothesize that the increased genomic instability associated with blast crisis may result in a low background of Bcr-Abl sequence variants, and STI-571 strongly selects for the emergence of kinase-active STI-571-resistant Bcr-Abl isoforms.

From the disclosure provided herein we conclude that with use of sensitive detection methods, Bcr-Abl kinase domain mutations can be detected in nearly all patients with relapsed myeloid blast crisis; that resistance frequently involves the coexistence of cell populations containing different kinase domain mutations; that Bcr-Abl kinase domain mutations exhibit a wide range of STI-571 resistance in vitro; that kinase domain mutations occur in a subset of chronic phase CML patients with persistence of the Philadelphia chromosome, and portend a poor prognosis; and that some STI-571-resistant kinase domain mutations can be occasionally detected in advanced phase cases CML prior to STI-571 treatment, and therefore may contribute to the leukemic drive in cells that harbor them. Bcr-Abl kinase domain mutations may thus contribute to the natural progression of CML from chronic to advanced phases in some cases. Given our findings, we believe routine sensitive sequence analysis of the Bcr-Abl kinase domain in patients being treated with STI-571 is warranted.

As noted above, the disclosure provided herein supports kinase domain mutation as the primary mechanism for STI-571 failure. Previous studies of kinase domain mutations have been performed largely on isolated cases of Philadelphia chromosome-positive ALL and CML in lymphoid blast crisis. Our finding of Bcr-Abl kinase domain mutations in nearly all cases of relapsed myeloid blast crisis was not expected based upon previous reports. Because the complete cytogenetic remission rate is lower in myeloid blast crisis patients treated with Gleevec, it is possible that resistance to Gleevec in patients with lymphoid blast crisis CML and Ph+ ALL more commonly represents greater genetic homogeneity. Less sensitive methods of mutation detection may therefore adequately demonstrate the presence of nucleotide substitutions in these cases, yet fail to reliably detect mutations in relapsed myeloid blast crisis cases.

While some previous studies suggested a predominance of one to two different kinase domain mutations in the majority of STI-571-resistant cases, our expanded analysis of the Bcr-Abl kinase domain in resistant cases reveals a large spectrum of such mutations (see FIG. 10). Inspection of the P-loop, which contains the consensus sequence Gly-X-Gly-X-X-Gly-X-Val (SEQ ID NO: 21), reveals the presence of STI-571-resistant mutations at each of the non-conserved amino acid sites. Moreover, kinase domain mutations are exceedingly common in cases of acquired resistance.

The methodology utilized in the current study represents the only technique by which the sequence of individual mRNA molecules can be determined. We demonstrate here that cells from patients with acquired resistance to STI-571 frequently represent a polyclonal population, with different cells containing different Bcr-Abl kinase domain mutations. Furthermore, this methodology affords increased sensitivity by enabling the detection of mutant isoforms that comprise as little as approximately 20 percent of the resistant population of cells. In many of our examples of polyclonal resistance, direct sequencing would be predicted to yield a consensus wild-type kinase domain sequence, due to lack of a clonally dominant clone. Moreover, we provide the first direct evidence for the presence of two separate kinase domain mutations on a single strand of DNA. The method of mutation detection employed here is thus expected to be superior to the method of direct cDNA sequencing utilized by other investigators, particularly in cases where emerging resistance is the result of polyclonal expansion.

We further document the first evidence of kinase domain mutations in cases of myeloid blast crisis prior to treatment with STI-571. While it is formally possible that such mutants merely reflect genomic instability, the finding of such mutants at a frequency of twenty percent is more suggestive of a significant clonal expansion of these cells. It is possible that certain kinase domain mutations may confer a growth advantage in affected cells. The viral oncogene v-abl is known to contain point mutations in addition to alternative N-terminal coding sequences when compared with murine c-abl. In this study we detected T315I prior to treatment in a patient whose disease subsequently failed to respond to STI-571. Interestingly, at the corresponding residue in the src gene, v-src differs from its cellular counterpart by substitution of isoleucine for threonine. Given a complete lack of kinase-domain mutations in pretreatment samples obtained from patients who subsequently responded to STI-571, the presence of kinase domain mutations prior to treatment may represent a marker for refractory disease, most likely related to increased genetic heterogeneity.

We detected kinase domain mutations in the majority of chronic phase patients who subsequently suffered progressive disease, and in only one of nine patients who have a continued hematologic response on STI-571 despite the persistence of the Philadelphia chromosome. The ability to detect kinase domain mutations in this setting thus appears to serve as a strong predictor for the likelihood of hematologic relapse. Moreover, all three patients with disease progression had evidence of their mutations prior to exhibiting clinical signs of progressive disease. Periodic mutation analysis in this setting may be warranted to facilitate alternative therapies. The only example of a detectable mutation in chronic phase CML without disease progression consisted of the V379I mutation, which has not been detected in any other patients. Given the correlation between the kinase domain mutations which have been shown to be functionally active in this study and disease progression in the chronic phase despite STI-571 therapy, it may be useful to periodically perform kinase domain mutation analysis of patients on STI-571 who have any degree of persistence of the Philadelphia chromosome in an effort to anticipate disease progression and to facilitate the prompt institution of allogeneic transplantation or other treatment options.

Our finding of mutant P210 isoforms in the overwhelming majority of patients at the time of acquired resistance reinforces point mutation in the Bcr-Abl kinase domain as a primary reason for STI-571 failure. The future of targeted therapy for CML is thus dependent upon overcoming STI-571 resistance mediated by Bcr-Abl kinase domain mutations. The differential sensitivity of kinase domain mutant isoforms to STI-571 deserves consideration. Given the sensitivity of some mutants, such as F317L, M351T, and E355G, to concentrations of STI-571 theoretically obtainable in humans, trials of higher doses of STI-571 may be warranted in some cases of acquired resistance. However, a few mutations, such as T315I, E255K, and G250E, clearly confer resistance to very high concentrations of STI-571. We speculate that medical management in the future of both chronic and advanced phase CML exhibiting acquired resistance to STI-571 will necessitate mutation-specific PCR, and depending upon the presence or absence of certain mutations, dose escalation can be attempted. Should a highly resistant mutant isoform, such as T315I, E255K, or G250E subsequently achieve clonal dominance, second generation drugs with activity against the most STI-571-resistant isoforms could then be employed.

The clinical applicability of highly sensitive methods for mutation detection is most well-established in the treatment of human immunodeficiency virus (HIV), where, armed with a number of targeted therapies, clinicians make treatment decisions periodically based upon the spectrum of retroviral mutations detected in the blood of their patients. Occasionally, drug-resistant mutations significantly hamper the ability of virus to replicate, and anti-retroviral agents are withdrawn in an effort to allow re-establishment of wild-type HIV. It will be important to characterize the biochemical and biological activity of each of the various mutant Bcr-Abl isoforms. If, in comparison with wild-type Bcr-Abl, some STI-571-resistant mutations actually impart decreased growth promoting effects, intermittent STI-571 therapy could be instituted in an effort to delay disease progression toward the blast crisis stage.

The development of STI-571 for the treatment of CML continues to represent a major advance toward the future of targeted therapy for human malignancies. Our work clearly implicates the activity of Bcr-Abl as essential to the malignant clone in nearly all acquired resistance cases studied. Imatinib is used much more commonly to treat chronic phase CML. Here we have provided examples of kinase domain mutations in four of fourteen cases of cytogenetic persistence despite STI-571 therapy. The presence of kinase domain mutation strongly correlated with subsequent development of progressive disease and decreased overall survival. The activity of Bcr-Abl therefore remains an optimal target for future therapies. In light of our findings, attempts to understand acquired resistance to other malignancies treated with STI-571, such as metastatic gastrointestinal stromal tumors, might logically begin with sensitive sequence analysis of the c-Kit kinase domain. We envision the future of clinical management for CML to involve, in addition to the routine usage of sensitive kinase domain mutation detection methods, combination molecular therapy, using multiple agents with the ability to target Bcr-Abl as well as kinase-active STI-571-resistant isoforms in addition to downstream effectors.

Typical embodiments of the invention are described below.

MARS Polynucleotides

A number of specific sequences of MARS are identified in Table I below. One aspect of the invention provides polynucleotides corresponding or complementary to all or part of a MARS gene, mRNA, and/or coding sequence, preferably in isolated form, including polynucleotides encoding a MARS protein and fragments thereof, DNA, RNA, DNA/RNA hybrid, and related molecules, polynucleotides or oligonucleotides complementary to a MARS gene or mRNA sequence or a part thereof, and polynucleotides or oligonucleotides that hybridize to a MARS gene, mRNA, or to a MARS encoding polynucleotide (collectively, "MARS polynucleotides"). As used herein, the MARS gene and protein is meant to include the MARS genes and proteins specifically described herein and the genes and proteins corresponding to MARS proteins. Typical embodiments of the invention disclosed herein include MARS polynucleotides containing specific portions of the MARS mRNA sequence (and those which are complementary to such sequences), for example, those that encode the T315I codon sequence.

Therefore, one specific aspect of the invention provides polynucleotides corresponding or complementary to all or part of a T315I Bcr-Abl gene, mRNA, and/or coding sequence, preferably in isolated form, including polynucleotides encoding a T315I Bcr-Abl protein and fragments thereof, DNA, RNA, DNA/RNA hybrid, and related molecules, polynucleotides or oligonucleotides complementary to a T315I Bcr-Abl gene or mRNA sequence or a part thereof, and polynucleotides or oligonucleotides that hybridize to a T315I Bcr-Abl gene, mRNA, or to a T315I Bcr-Abl encoding polynucleotide (collectively, "T315I Bcr-Abl polynucleotides"). As used herein, the T315I Bcr-Abl gene and protein is meant to include the T315I Bcr-Abl genes and proteins specifically described herein and the genes and proteins corresponding to T315I Bcr-Abl proteins. Typical embodiments of the invention disclosed herein include T315I Bcr-Abl polynucleotides containing specific portions of the T315I Bcr-Abl mRNA sequence (and those which are complementary to such sequences), for example, those that encode the T315I codon.

The MARS polynucleotides of the invention are useful for a variety of purposes, including but not limited to their in the detection of the MARS gene(s), mRNA(s), or fragments thereof; as reagents for the diagnosis and/or prognosis of cancers; as coding sequences capable of directing the expression of MARS polypeptides; as tools for modulating or inhibiting the function of the MARS protein.

Further specific embodiments of this aspect of the invention include primers and primer pairs, which allow the specific amplification of the MARS polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a MARS polynucleotide in a sample and as a means for detecting a cell expressing a MARS protein.

Examples of such probes and primers include polypeptides comprising all or part of a human MARS cDNA sequence shown in Table I. Examples of primer pairs capable of specifically amplifying MARS mRNAs (e.g. those primers disclosed herein) are readily ascertainable by those skilled in the art. As will be understood by the skilled artisan, a great many different primers and probes may be prepared based on the sequences provided in herein and used effectively to amplify and/or detect a MARS mRNA.

Recombinant DNA Molecules and Host-Vector Systems

The invention also provides recombinant DNA or RNA molecules containing a MARS polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a MARS polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 cell). Examples of suitable mammalian cells include various cancer cell lines, other transfectable or transducible cell lines, including those mammalian cells routinely used for the expression of recombinant proteins (e.g., COS, CHO, 293, 293T cells etc.). More particularly, a polynucleotide comprising the coding sequence of a MARS may be used to generate MARS proteins or fragments thereof using any number of host vector systems routinely used and widely known in the art.

A wide range of host vector systems suitable for the expression of MARS proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαt-kneo (Muller et al., 1991, MCB 11:1785). Using these expression vectors, MARS may be preferably expressed in cell lines, including for example CHO COS, 293, 293T, rat-1, 3T3 etc. The host vector systems of the invention are useful for the production of a MARS protein or fragment thereof. Such host-vector systems may be employed to study the functional properties of MARS and MARS mutations.

MARS Polypeptides

Another aspect of the present invention provides MARS proteins and polypeptide fragments thereof. The MARS proteins of the invention include those specifically identified herein. Fusion proteins that combine parts of different MARS proteins or fragments thereof, as well as fusion proteins of a MARS protein and a heterologous polypeptide are also included. Such MARS proteins will be collectively referred to as the MARS proteins, the proteins of the invention, or MARS. As used herein, the term "MARS polypeptide" refers to a polypeptide fragment or a MARS protein of at least about 6 amino acids (e.g. a Bcr-Abl polypeptide having about 6 contiguous amino acids including a MARS such as T315I, preferably at least about 10-15 amino acids).

Proteins encoded by the MARS genes, or by fragments thereof, will have a variety of uses, including but not limited to generating antibodies and in methods for identifying ligands and other agents (e.g. small molecules such as 2-phenylpyrimidines) and cellular constituents that bind to a MARS gene product. Antibodies raised against a MARS protein or fragment thereof may be useful in diagnostic and prognostic assays, imaging methodologies (including, particularly, cancer imaging), and therapeutic methods in the management of human cancers characterized by expression of a MARS protein, including but not limited to cancer of the lymphoid lineages. Various immunological assays useful for the detection of MARS proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting leukemia cells (e.g., in radioscintigraphic imaging methods).

MARS Antibodies

The term "antibody" is used in the broadest sense and specifically covers single anti-MARS monoclonal antibodies (including agonist, antagonist and neutralizing antibodies) and anti-MARS antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

Another aspect of the invention provides antibodies that immunospecifically bind to MARS proteins and polypeptides. The most preferred antibodies will specifically bind to a MARS protein and will not bind (or will bind weakly) to Bcr-Abl proteins and polypeptides. Anti-MARS antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

For some applications, it may be desirable to generate antibodies which specifically react with a particular MARS protein and/or an epitope within a particular structural domain. For example, preferred antibodies useful for diagnostic purposes are those which react with an epitope in a mutated region of the MARS protein as expressed in cancer cells. Such antibodies may be generated by using the MARS proteins described herein, or using peptides derived from various domains thereof, as an immunogen.

MARS antibodies of the invention may be particularly useful in cancer (e.g. chronic myelogenous leukemia) therapeutic strategies, diagnostic and prognostic assays, and imaging methodologies. Similarly, such antibodies may be useful in the diagnosis, and/or prognosis of other cancers, to the extent MARS is also expressed or overexpressed in other types of cancer. The invention provides various immunological assays useful for the detection and quantification of MARS and mutant MARS proteins and polypeptides. Such assays generally comprise one or more MARS antibodies capable of recognizing and binding a MARS or mutant MARS protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancer cells are also provided by the invention, including but limited to radioscintigraphic imaging methods using labeled MARS antibodies. Such assays may be used clinically in the detection, monitoring, and prognosis of cancers, particularly chronic myeloid leukemia.

Mars Transgenic Animals

Nucleic acids that encode MARS can also be used to generate either transgenic animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding T315I Bcr-Abl can be used to clone genomic DNA encoding T315I Bcr-Abl in accordance with established techniques and the genomic sequences used to generate transgenic animals that contain cells that express DNA encoding T315I Bcr-Abl. Methods for generating transgenic animals, particularly animals such as mice or rats, have become conventional in the art and are described, for example, in U.S. Pat. Nos. 4,736,866 and 4,870,009. Typically, particular cells would be targeted for MARS transgene incorporation with tissue-specific enhancers. Transgenic animals that include a copy of a transgene encoding MARS introduced into the germ line of the animal at an embryonic stage can be used to examine the effect of increased expression of DNA encoding MARS. Such animals can be used as tester animals for reagents thought to confer protection from, for example, pathological conditions associated with its expression. In accordance with this facet of the invention, an animal is treated with the reagent and a reduced incidence of the pathological condition, compared to untreated animals bearing the transgene, would indicate a potential therapeutic intervention for the pathological condition.

Methods for the Detection of MARS

Another aspect of the present invention relates to methods for detecting MARS polynucleotides and MARS proteins, as well as methods for identifying a cell that expresses MARS. The expression profile of MARS makes them diagnostic markets for disease states. As discussed in detail below, the status of MARS gene products in patient samples may be analyzed by a variety protocols that are well known in the art including immunohistochemical analysis, the variety of Northern blotting techniques including in situ hybridization, RT-PCR analysis (for example on laser capture micro-dissected samples), western blot analysis and tissue array analysis.

More particularly, the invention provides assays for the detection of MARS polynucleotides in a biological sample, such as cell preparations, and the like. A number of methods for amplifying and/or detecting the presence of MARS polynucleotides are well known in the art and may be employed in the practice of this aspect of the invention.

In one embodiment, a method for detecting a MARS mRNA in a biological sample comprises producing cDNA from the sample by reverse transcription using at least one primer; amplifying the cDNA so produced using a MARS polynucleotides as sense and antisense primers to amplify MARS cDNAs therein; and detecting the presence of the amplified MARS cDNA. Any number of appropriate sense and antisense probe combinations may be designed from the nucleotide sequences provided for the MARS and used for this purpose.

The invention also provides assays for detecting the presence of a MARS protein in a biological sample. Methods for detecting a MARS protein are also well known and include, for example, immunoprecipitation, immunohistochemical analysis, Western Blot analysis, molecular binding assays, ELISA, ELIFA and the like. For example, in one embodiment, a method of detecting the presence of a MARS protein in a biological sample comprises first contacting the sample with a MARS antibody, a MARS-reactive fragment thereof, or a recombinant protein containing an antigen binding region of a MARS antibody; and then detecting the binding of MARS protein in the sample thereto.

Methods for identifying a cell that expresses MARS are also provided. In one embodiment, an assay for identifying a cell that expresses a MARS gene comprises detecting the presence of MARS mRNA in the cell. Methods for the detection of particular mRNAs in cells are well known and include, for example, hybridization assays using complementary DNA probes (such as in situ hybridization using labeled MARS riboprobes, Northern blot and related techniques) and various nucleic acid amplification assays (such as RT-PCR using complementary primers specific for MARS, and other amplification type detection methods, such as, for example, branched DNA, SISBA, TMA and the like).

A significant aspect of the invention disclosed herein is the discovery that amino acid substitutions in the Bcr-Abl polypeptide sequence shown in SEQ ID NO: 1 can produce cancer cells having a resistance to tyrosine kinase inhibitors such as STI-571. Specifically those skilled in that art understand that the physiological mechanisms of drug resistance are diverse and that drug resistance typically occurs through other mechanisms such as an increase in the expression of proteins that export the drug out of the cell (see, e.g. Suzuki et al., Curr Drug Metab 2001 December; 2(4):367-77). Consequently, the disclosure herein provides the scientific evidence to confirm the Bcr-Abl polypeptide sequence shown in SEQ ID NO: 1 as a target for analysis in methods relating to identifying drug resistant cells, such as methods of identifying an amino acid substitution in at least one Bcr-Abl polypeptide expressed in human cancer cell from an individual selected for treatment with a tyrosine kinase inhibitor.

A preferred embodiment of the invention is a method of identifying at least one amino acid substitution in at least one Bcr-Abl polypeptide having some level of tyrosine kinase activity that is expressed in a human cancer cell from an individual selected for treatment with a tyrosine kinase inhibitor, the method comprising determining the polypeptide sequence of at least one Bcr-Abl polypeptide expressed by the human cancer cell and comparing the polypeptide sequence of the Bcr-Abl polypeptide expressed by the human cancer cell to the Bcr-Abl polypeptide sequence shown in SEQ ID NO: 1 so that an amino acid substitution in the Bcr-Abl polypeptide expressed by the human cancer cell can be identified. In preferred methods of the invention, an amino acid substitution so identified confers some level of resistance to STI-571.

A significant aspect of the invention disclosed herein is the delineation of a discreet region in the Bcr-Abl polypeptide sequence shown in SEQ ID NO: 1 that contains mutations that can produce cancer cells having a resistance to tyrosine kinase inhibitors such as STI-571. This discovery allows artisans to focus on this region in diagnostic protocols so as to facilitate such analyses. In this context, a preferred method of the invention is a method of identifying an amino acid substitution in at least one Bcr-Abl polypeptide expressed in a human cancer cell from an individual selected for treatment with a tyrosine kinase inhibitor, the method comprising determining the polypeptide sequence of at least one Bcr-Abl polypeptide expressed by the human cancer cell and comparing the polypeptide sequence of the Bcr-Abl polypeptide expressed by the human cancer cell to the Bcr-Abl polypeptide sequence shown in SEQ ID NO: 1 so that an amino acid substitution in the Bcr-Abl polypeptide expressed by the human cancer cell can be identified, wherein the amino acid substitution occurs in a region of the Bcr-Abl polypeptide sequence shown in SEQ ID NO: 1 comprising residue D233 through residue T406. Without being bound by a specific scientific theory, the data disclosed herein provides evidence that this region defines boundaries for the structural architecture of the portions of Bcr-Abl that are predominantly involved in an interaction with STI-571.

Another significant aspect of the invention disclosed herein is the delineation of a discreet subregions in the Bcr-Abl polypeptide sequence shown in SEQ ID NO: 1 that contains the mutations that can produce cancer cells having a resistance to tyrosine kinase inhibitors such as STI-571. This discovery allows artisans to focus on such subregions in diagnostic protocols so as to facilitate such analyses. In this context, a preferred method of the invention is a method of identifying an amino acid substitution in at least one Bcr-Abl polypeptide expressed in a human cancer cell from an individual selected for treatment with a tyrosine kinase inhibitor, the method comprising determining the polypeptide sequence of at least one Bcr-Abl polypeptide expressed by the human cancer cell and comparing the polypeptide sequence of the Bcr-Abl polypeptide expressed by the human cancer cell to the Bcr-Abl polypeptide sequence shown in SEQ ID NO: 1 so that an amino acid substitution in the Bcr-Abl polypeptide expressed by the human cancer cell can be identified, wherein the amino acid substitution occurs in the P-loop (residue G249 through residue V256 of the Bcr-Abl polypeptide sequence shown in SEQ ID NO: 1), helix C (residue E279 through residue I293 of the Bcr-Abl polypeptide sequence shown in SEQ ID NO: 1), the catalytic domain (residue H361 through residue R367 of the Bcr-Abl polypeptide sequence shown in SEQ ID NO: 1) or the activation loop (residue A380 through residue P402 of the Bcr-Abl polypeptide sequence shown in SEQ ID NO: 1). Alternatively, the amino acid substitution is proximal (e.g. within about 10 amino acid residues) to one of these subregions in a manner that perturbs the function of the subregion.

A particularly significant aspect of the invention disclosed herein is the delineation of a discreet residue positions in the Bcr-Abl polypeptide sequence shown in SEQ ID NO: 1 that, when mutated, can produce cancer cells having a resistance to tyrosine kinase inhibitors such as STI-571. This discovery allows artisans to focus on such residue positions in diagnostic protocols so as to facilitate such analyses. In this context, a preferred method of the invention is a method of identifying an amino acid substitution in at least one Bcr-Abl polypeptide expressed in a human cancer cell from an individual selected for treatment with a tyrosine kinase inhibitor, the method comprising determining the polypeptide sequence of at least one Bcr-Abl polypeptide expressed by the human cancer cell and comparing the polypeptide sequence of the Bcr-Abl polypeptide expressed by the human cancer cell to the Bcr-Abl polypeptide sequence shown in SEQ ID NO: 1 so that an amino acid substitution in the Bcr-Abl polypeptide expressed by the human cancer cell can be identified, wherein the amino acid substitution occurs at residue D233, T243, M244, K245, G249, G250, G251, Q252, Y253, E255, V256L Y257, F259, K262, D263, K264, S265, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, or T406.

This identification of discreet residue positions in the Bcr-Abl polypeptide sequence shown in SEQ ID NO: 1 that, when mutated, can produce cancer cells having a resistance to tyrosine kinase inhibitors such as STI-571 is significant in part because of art which teaches that in situations where methodical experimentation has established that the properties of a specific residue at a particular position within the polypeptide chain are crucial for maintaining some aspect of a protein's functional integrity, an alteration in the size, shape, charge, hydrogen-bonding capacity or chemical reactivity of the amino acid side chain at one of these "active" amino acid positions is likely to affect the properties of the protein in some way (See e.g. Rudiger et al., Peptide Hormones, University Park Press (1976)). For this reason, the skilled artisan would reasonably expect a substitution in a residue shown to be important for the inhibition of tyrosine kinase activity by STI-571 in the wild type protein to effect the ability of STI-571 to inhibit the kinase activity of the Bcr-Abl polypeptide. As disclosed herein, the specific effects of any substitution mutation (or a truncation, a deletion, a frame shift etc.) on STI-571 resistance can be examined by protocols such as those disclosed in the examples below.

In specific embodiments of the methods disclosed herein, the amino acid substitution is D233H, T243S, M244V, G249D, G250E, G251S, Q252H, Y253F, Y253H, E255K, V256L, Y257F, Y257R, F259S, K262E, D263G, K264R, S265R, V268A, V270A, T272A, Y274C, Y274R, D276N, T277P, M278K, E82G, F283S, A288T, A288V, M290T, K291R, E292G, I293T, P296S, L298M, L298P, V299L, Q300R, G303E, V304A, V304D, C305S, C305Y, T306A, F311L, I314V, T315A, T315I, E316G, F317L, M318T, Y320C, Y320H, G321E, D325H, Y326C, L327P, R328K, E329V, Q333L, A337V, V339G, L342E, M343V, M343T, A344T, A344V, I347V, A350T, M351T, E352A, E352K, E355G, K357E, N358D, N358S, F359V, I360K, I360T, L364H, E373K, N374D, K378R, V379I, A380T, A380V, D381G, F382L, T389S, T392A, T394A, A395G, H396K, A399G, P402T or T406A. While the identification of substitutions is a preferred embodiment of the invention, the methods disclosed herein can also be used to identify other mutations that are associated with resistance to tyrosine kinase inhibitors such as STI-571 such as truncations that result from a mutation that introduces a stop codon at an amino acid residue position such as K245STOP or E334STOP.

Embodiments of the invention include those that examine any one to all of the amino acid positions in the Bcr-Abl polypeptide sequence (e.g. M1, L2, E3 through V1128, Q1129 and R1130) as occurs when one compares the sequence of a polypeptide expressed by a cancer cell with the polypeptide sequence shown in SEQ ID NO: 1. In this context, in preferred embodiments of the invention, one can examine residue G250, Q252, E255, K264, V270, F283, M290, P296, V304, T315, F317, R328, M343, M343, A344, M351T, E35, K357, I360, V379 or H396. In specific embodiments one can examine residue G250, Q252, Y253, E255, T315, F317, M351 or E355.

As is known in the art, it may be desirable to examine one residue but not necessarily all of the amino acid positions in the Bcr-Abl polypeptide sequence. Consequently, another embodiment of the invention is a method of identifying an amino acid substitution in at least one Bcr-Abl polypeptide expressed in a human cancer cell from an individual selected for treatment with a tyrosine kinase inhibitor, the method comprising determining the polypeptide sequence of at least one Bcr-Abl polypeptide expressed by the human cancer cell and comparing the polypeptide sequence of the Bcr-Abl polypeptide expressed by the human cancer cell to the Bcr-Abl polypeptide sequence shown in SEQ ID NO: 1 so that an amino acid substitution in the Bcr-Abl polypeptide expressed by the human cancer cell can be identified, wherein the amino acid substitution does not occur at residue G250, Q252, E255, K264, V270, F283, M290, P296, V304, T315, F317, R328, M343, M343, A344, M351T, E35, K357, I360, V379 or H396. Corresponding embodiments of the invention include those that examine one or more amino acid mutations in a Bcr-Abl polypeptide but do not examine another specific amino acid position in the Bcr-Abl polypeptide sequence (e.g. methods which examine residue position 315 but not residue position 255).

The polynucleotide and/or polypeptide sequences of Bcr-Abl can be identified by any one of a wide variety of protocols known in the art such as those disclosed herein. In preferred methods, the Bcr-Abl polynucleotide expressed by the human cancer cell is isolated by the polymerase chain reaction. In addition, methods used in the identification of one Bcr-Abl polypeptide expressed in a human cancer cell from an individual selected for treatment with one tyrosine kinase inhibitor can be identical to methods used in the identification of one Bcr-Abl polypeptide expressed in a human cancer cell from an individual selected for treatment with another tyrosine kinase inhibitor. In illustrative methods of the invention, the kinase inhibitor is a 2-phenylaminopyrimidine.

As noted herein, the methods of the present invention can be used in determining whether or not to treat an individual with a specific tyrosine kinase inhibitor such as STI-571. Another embodiment of the invention disclosed herein is a method of identifying a mutation in a Bcr-Abl polynucleotide in a mammalian cell, wherein the mutation in a Bcr-Abl polynucleotide is associated with resistance to inhibition of Bcr-Abl tyrosine kinase activity by a 2-phenylaminopyrimidine, the method comprising determining the sequence of at least one Bcr-Abl polynucleotide expressed by the mammalian cell and comparing the sequence of the Bcr-Abl polynucleotide to the Bcr-Abl polynucleotide sequence encoding the polypeptide sequence shown in SEQ ID NO: 1, wherein the mutation in the Bcr-Abl polynucleotide comprises an alteration at amino acid residue position: D233, T243, M244, K245, G249, G250, G251, Q252, Y253, E255, V256L Y257, F259, K262, D263, K264, S265, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, or T406 of the polypeptide sequence shown in SEQ ID NO: 1. As used herein, "a Bcr-Abl polynucleotide associated with resistance to inhibition of Bcr-Abl tyrosine kinase by a 2-phenylaminopyrimidine" refers to a Bcr-Abl polynucleotide that has been identified in cancer cells that exhibit some level of resistance to a 2-phenylaminopyrimidine such as STI-571 (or analogs or derivatives thereof) and which encodes a polypeptide having at least one amino acid difference from the polypeptide sequence shown in SEQ ID NO: 1 (e.g. those disclosed in Table IA). Preferably the Bcr-Abl polynucleotide associated with resistance to inhibition of Bcr-Abl tyrosine kinase by a 2-phenylaminopyrimidine encodes a polypeptide that exhibits exhibit some level of resistance to a 2-phenylaminopyrimidine such as STI-571.

Optionally, in the methods disclosed above, the mammalian cell is a human cancer cell. In preferred methods, the human cancer cell is a chronic myeloid leukemia cell. In highly preferred methods, the human cancer cell is obtained from an individual treated with STI-571. Optionally, the amino acid substitution in the Bcr-Abl polypeptide expressed in human cancer cell confers resistance to inhibition of tyrosine kinase activity by STI-571.

MARS expression analysis may also be useful as a tool for identifying and evaluating agents that modulate MARS gene expression. Identification of a molecule or biological agent that could inhibit MARS activity is of therapeutic value.

Monitoring the Status of MARS

The finding that MARS mRNA is expressed in cancers demonstrating STI-571 resistance provides evidence that mutations in Bcr-Abl are associated with STI-571 resistance and therefore identifies these genes and their products as targets that the skilled artisan can use to evaluate biological samples from individuals suspected of having a disease associated with MARS expression. In this context, the evaluation of the status of MARS genes and their products can be used to gain information on the disease potential of a tissue sample.

The term "status" in this context is used according to its art accepted meaning and refers to the condition a gene and its products including, but not limited to the integrity and/or methylation of a gene including its regulatory sequences, the location of expressed gene products (including the location of MARS expressing cells), the presence, level (e.g. the percentage of MARS expressing myeloid cancer cells in a total population of myeloid cancer cells), and biological activity of expressed gene products (such as MARS mRNA polynucleotides and polypeptides), the presence or absence of transcriptional and translational modifications to expressed gene products as well as associations of expressed gene products with other biological molecules such as protein binding partners. The status of MARS can be evaluated by a wide variety of methodologies well known in the art, typically those discussed below.

The status of MARS may provide information useful for predicting susceptibility to particular disease stages, progression, and/or tumor aggressiveness. The invention provides methods and assays for determining MARS status and diagnosing cancers that express MARS. MARS status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the status of the MARS gene and gene products can be found, for example in Ausubul et al. eds., 1995, Current Protocols In Molecular Biology, Units 2 [Northern Blotting], 4 [Southern Blotting], 15 [Immunoblotting] and 18 [PCR Analysis].

A typical aspect of the invention is directed to assessing the effectiveness of STI-571 in a therapeutic regimen. In a representative embodiment, a method for assessing the effectiveness of STI-571 comprises detecting MARS mRNA or MARS protein in a tissue sample, its presence indicating a likely resistance to STI-571, wherein the degree of MARS mRNA expression (e.g. the percentage of clones that express one or more MARS) is proportional to the likelihood of resistance to STI-571.

Another aspect of the invention is directed to examining the stage of cancer in an individual. In one embodiment, a method for examining a stage of cancer comprises detecting MARS mRNA or MARS protein in a tissue sample, its presence indicating susceptibility to cancer, wherein the degree of MARS mRNA expression present is proportional to the degree of susceptibility. In a specific embodiment, the presence of MARS in a tissue sample is examined, with the presence of MARS in the sample providing an indication of a stage of leukemia (or the emergence or existence of a leukemia). In a closely related embodiment, one can evaluate the integrity MARS nucleotide and amino acid sequences in a biological sample in order to identify perturbations in the structure of these molecules such as insertions, deletions, substitutions and the like, with the presence of one or more perturbations in MARS gene products in the sample providing an indication of cancer stage or susceptibility (or the emergence or existence of a cancer type or stage).

Yet another related aspect of the invention is directed to methods for gauging tumor aggressiveness. In one embodiment, a method for gauging aggressiveness of a tumor comprises determining the level of MARS mRNA or MARS protein expressed by cells in a sample of the tumor, comparing the level so determined to the level of MARS mRNA or MARS protein expressed in a corresponding control tissue, wherein the degree of MARS mRNA expression present is proportional to the degree of aggressiveness. In a specific embodiment, aggressiveness of leukemias is evaluated by determining the extent to which MARS is expressed in the tumor cells, with relatively higher numbers of cells expressing one or more MARS indicating more aggressive tumors (e.g. in that they are resistant to a therapeutic agent such as STI-571).

Yet another related aspect of the invention is directed to methods for observing the progression of a malignancy in an individual over time. In one embodiment, methods for observing the progression of a malignancy in an individual over time comprise determining the level of MARS mRNA or MARS protein expressed by cells in a sample of the tumor, comparing the level so determined to the level of MARS mRNA or MARS protein expressed in an equivalent tissue sample taken from the same individual at a different time, wherein the degree of MARS mRNA or MARS protein expression in the tumor sample over time provides information on the progression of the cancer. In a specific embodiment, the progression of a cancer is evaluated by determining the extent to which MARS expression in the tumor cells alters over time, with higher expression levels over time indicating a progression of the cancer.

Gene amplification provides an additional method of assessing the status of Bcr-Abl. Gene amplification may be measured in a sample directly, for example, by conventional Southern blotting, Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

The above diagnostic approaches may be combined with any one of a wide variety of prognostic and diagnostic protocols known in the art. For example, another embodiment of the invention disclosed herein is directed to methods for observing a coincidence between the expression of MARS gene and/or MARS gene products and a factor that is associated with malignancy as a means of diagnosing and prognosticating the status of a tissue sample. In this context, a wide variety of factors associated with malignancy may be utilized such as the expression of genes otherwise associated with malignancy as well as gross cytological observations (see e.g. Bocking et al., 1984, Anal. Quant. Cytol. 6(2):74-88; Eptsein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of MARS gene and MARS gene products and an additional factor that is associated with malignancy are useful, for example, because the presence of a set or constellation of specific factors that coincide provides information crucial for diagnosing and prognosticating the status of a tissue sample.

In a typical embodiment, methods for observing a coincidence between the expression of MARS gene and MARS gene products (or perturbations in MARS gene and MARS gene products) and a factor that is associated with malignancy entails detecting the overexpression of MARS mRNA or protein in a tissue sample and then detecting the altered expression of another oncogene such RAS, or a tumor suppressor such as p53 or Rb, in a tissue sample, and observing a coincidence of MARS mRNA or protein expression and, for example, RAS mRNA or protein overexpression. In a specific embodiment, the expression of MARS and RAS mRNA in tissue is examined. In a preferred embodiment, the coincidence of MARS and RAS mRNA overexpression in the sample provides an indication of leukemia stage, or the emergence or existence of a leukemia.

Preferred embodiments of the invention described herein include methods for characterizing a cancer genotype and/or phenotype such as the genotype and/or phenotype of cancers of the myeloid lineage. Specific embodiments of the invention described herein include methods of assessing the likelihood of resistance to a nucleotide analog such as 2-phenylamino pyrimidine. Particular embodiments of the invention described herein include methods for specifically identifying cells having some degree of resistance to STI-571. Such methods typically include the step of sequencing a target kinase such as Bcr-Abl to identify a mutation associated with a specific genotype or phenotype such as resistance to STI-571. Preferably the mutation is within a domain shown to be associated with the cancer genotype and/or phenotype (e.g. the ATP binding domain of Bcr-Abl). More preferably the mutation is in a Bcr-Abl residue identified in Table I below (or in an equivalent residue of a kinase having homology to Bcr-Abl).

A variety of permutations of these methods are provided by the invention disclosed herein. For example, the invention disclosed herein allows artisans to examine MARS in a variety of contexts to determine whether different mutations segregate with specific clinical phenotypes (e.g. lymphoid versus myeloid disease) or with different clinical patterns of STI-571 resistance (e.g. refractory disease; delayed relapse versus rapid relapse). The invention further allows those skilled in the art to determine whether kinase domain mutations restricted to patients with advanced stage disease or also occur in chronic phase patients. The invention also allows those skilled in the art to determine whether one or more mutations are a manifestation of the clonal diversity and genetic instability associated with disease progression. The invention also allows those skilled in the art to determine whether such mutations are a consequence of prior exposure to chemotherapy, or occur only in patients exposed to STI-571. The invention also allows those skilled in the art to determine the biological implications for other targeted kinase inhibitors currently in clinical development.

Methods for detecting and quantifying the expression of MARS mRNA or protein are described herein and use standard nucleic acid and protein detection and quantification technologies well known in the art. Standard methods for the detection and quantification of MARS mRNA include in situ hybridization using labeled MARS riboprobes, northern blot and related techniques using MARS polynucleotide probes, RT-PCR analysis using primers specific for MARS, and other amplification type detection methods, such as, for example, branched DNA, SISBA, TMA and the like. In a specific embodiment, semi-quantitative RT-PCR may be used to detect and quantify MARS mRNA expression as described in the Examples that follow. Any number of primers capable of amplifying MARS may be used for this purpose, including but not limited to the various primer sets specifically described herein. Standard methods for the detection and quantification of protein may be used for this purpose. In a specific embodiment, polyclonal or monoclonal antibodies specifically reactive with the MARS protein may be used in an immunohistochemical assays of samples. Antibodies directed against MARS protein can also be used to detect MARS in a patient specimen (e.g., blood or other sample) using conventional techniques such as fluorescence-activated cell sorting (FACS) and/or ELISA.

As discussed in detail below, once a mutant sequence is identified one can then identify compounds which bind and/or inhibit the activity of the mutant kinases.

Methods for Identifying and Characterizing MARS

The disclosure provided herein allows those skilled in the art to identify and characterize cells having a genotype and/or phenotype associated with a cancer such as a genotype and/or phenotype associated with cancers of the myeloid lineage. Specific embodiments of the invention described herein include methods for the identification and characterization of Bcr-Abl mutants associated resistance to a nucleotide analog such as 2-phenylamino pyrimidine. Particular embodiments of the invention described herein include methods for the identification and characterization of cells having some degree of resistance to an inhibitor such as STI-571.

A first method for characterizing cells having a genotype and/or phenotype associated with a cancer includes the sequencing of Bcr-Abl in those cells to identify one or more mutations associated with a particular phenotype (e.g. resistance to STI-571) such as a mutation in a domain or region shown to be associated with a specific genotype and/or phenotype (e.g. the ATP binding domain of Bcr-Abl). Preferably the mutation is in a Bcr-Abl residue identified in Table I below.

A related method for characterizing cells having a genotype and/or phenotype associated with a cancer and/or cancer stage includes considering the location of the mutation in the context of the crystal structure of the ABL kinase domain bound to a variant STI-571 (see, e.g. Schindler et al., Science. 2000 Sep. 15; 289(5486):1938-42). This definition of the crystal structure allows one to evaluate whether the mutation might interfere with the anti-leukemia activity of STI-571. Based on this analysis, one can prioritize mutations for direct experimental analysis of ABL kinase activity, leukemogenicity and level of inhibition by STI-571.

Another method for characterizing cells having a genotype and/or phenotype associated with a cancer and/or cancer stage includes analyzing another factor associated a genotype and/or phenotype associated with a cancer in a target cell being examined such as the stage of the disease progression, the relative frequency of the mutant within the population (e.g. is the clone a dominant population which provides evidence that they have a growth advantage).

Another method for characterizing cells having a genotype and/or phenotype associated with a cancer includes engineering selected mutations into wild-type BCR-ABL cDNA to create a mutant allele whose enzymological and biological properties can be examined directly. Enzymology can be performed by measuring tyrosine kinase activity in vitro or in cells using standard assays known in the art (see, e.g. those cited in Example 1). Biological activity can be measured using standard oncogene transformation assays using growth factor dependent hematopoietic cell lines or primary mouse bone marrow cells (see, e.g. those cited in Example 1). In this way, resistance to STI-571 can be measured using such kinase assays and transformation assays.

Those skilled in the art will understand that the above described assays for characterizing cells having a genotype and/or phenotype associated with a cancer can be performed independently or in combination with each other.

Mutations in Related Molecules

Residues shown to mutated in MARS occur in domains that are highly conserved among members of the protein kinase family (see, e.g. Hanks et al., Science 241: 42-51 (1988)). The finding that a highly conserved residue is mutated in cancers and that this mutation is associated with resistance to a chemotherapeutic agent provides evidence that this domain is associated with dysregulated cell growth and therefore identifies these domains and residue position as a targets that the skilled artisan can use to evaluate the status of related members of the tyrosine kinase family (see, e.g. those identified in FIG. 1 of Hanks et al., Science 241: 42-51 (1988)), from individuals suspected of having a disease associated with the dysregulation of that member of the tyrosine kinase family.

In this context, the evaluation of the status of a domain and/or residue in the tyrosine kinase family member can be used to gain information on the disease potential of a tissue sample. For example, in a syndrome in which the dysregulation of a specific tyrosine kinase family member is known or suspected (preferably one that exhibits a pattern of pathology that is similar to that seen with Bcr-Abl), one can determine if a mutation has occurred at that residue in order to obtain evidence of genetic changes associated with growth dysregulation (e.g. resistance to a chemotherapeutic agent). Methods for the detection of mRNAs having such specific mutations in cells are well known and include, for example, hybridization assays using complementary DNA probes (such as in situ hybridization, Northern blot and related techniques) and various nucleic acid amplification assays (such as RT-PCR using complementary primers specific for the mRNA of interest, and other amplification type detection methods, such as, for example, branched DNA, SISBA, TMA and the like). As discussed below, methods for identifying molecules that interact with such mutant members of the tyrosine kinase family are also provided.

Embodiments of the invention include methods for identifying a functional hotspot (e.g. a region in a protein which has significant functional importance in kinase activity and drug resistance) in a target kinase comprising sequencing at least a portion of the target kinase to identify a mutation and comparing the location of the mutation to the location of functional hotspots identified in a homologous kinase (e.g. Bcr-Abl), wherein the identification of a mutation in a target kinase that corresponds to a hotspot in a homologous kinase provides evidence that the mutation in the target kinase is in a functional hotspot. Typically the hotspot occurs in a Bcr-Abl domain having mutations associated with STI-571 resistance (e.g. the activation loop). More preferably the hotspot occurs in a Bcr-Abl residue identified in Table I. Preferably, the homologous kinase is Bcr-Abl and the homologies are compared via a BLAST analysis. The target kinase may be any one of a wide variety of kinases known in the art such as c-kit, PDGFR, EGFR and VEGFR or one of the kinases identified in FIG. 1 of Hanks et al., Science 241: 42-51 (1988). Optionally these methods can be used to characterize cells from patients suffering from a pathology associated with aberrant expression of the target kinase.

Other embodiments of the invention include methods for assessing the likelihood of a target kinase having a resistance to a nucleotide analog such as 2-phenylamino pyrimidine comprising sequencing at least a portion of the target kinase to identify a mutation, wherein the identification of a mutation in a target kinase that corresponds to a hotspot in a homologous kinase provides evidence that target kinase will be resistant to the inhibitor. Preferably the hotspot occurs in a Bcr-Abl domain having mutations associated with STI-571 resistance. More preferably the hotspot occurs in a Bcr-Abl residue identified in Table I. Preferably, the homologous kinase is Bcr-Abl and the homologies are compared via a BLAST analysis. The target kinase may be any one of a wide variety of kinases known in the art such as c-kit, PDGFR, EGFR and VEGFR or one of the kinases identified in FIG. 1 of Hanks et al., Science 241: 42-51 (1988) which is incorporated herein by reference. Optionally these methods can be used to characterize cells from patients suffering from a pathology associated with aberrant expression of the target kinase.

The invention disclosed herein includes the identification of amino acid residues in Bcr-Abl that are mutated in a manner characterized such that they retain kinase activity yet are associated with resistance to inhibition of kinase activity by a 2-phenylaminopyrimidine. One embodiment of an invention provided by this disclosure is a method of identifying such a mutation in an Abelson protein kinase, wherein the mutation is associated with the resistance to an inhibition of kinase activity by a 2-phenylaminopyrimidine, the method comprising: determining an amino acid sequence of a portion of a polynucleotide encoding the Abelson protein kinase to determine the presence of a mutation, wherein the mutation occurs at a amino acid residue at the same relative position as a mutation in the C-Abl protein kinase shown in SEQ ID NO: 1 that is associated with STI-571 resistance as determined using the homology criteria of BLAST analysis. In this context, skilled artisans understand that mutations in the C-Abl protein kinase shown in SEQ ID NO: 1 that are associated with STI-571 resistance include mutations in the C-Abl protein kinase which have, for example, been identified in cancer cells isolated from individuals shown to exhibit a resistance to a therapeutic regime involving a 2-phenylaminopyrimidine such as STI-571. As disclosed herein, mutants of the C-Abl protein kinase shown in SEQ ID NO: 1 that are identified as being associated with STI-571 resistance are readily characterized by any one of a wide variety of techniques that are well known in the art in view of the extensive biological characterization of c-Abl, Bcr-Abl and/or one of the Abelson protein kinases such as ARG etc. Such protocols include analyses based on the understanding of the biological significance of a domain or residue within these proteins that has been characterized as having significance in kinase activity or small molecule interaction (see, e.g. Example 3 below which identifies various previously identified domains as well as residues which directly interact with STI-571 via previously described crystallographic analyses etc). Such protocols further include biological analyses of biological activity of these mutants including for example, the well known assays for characterizing the kinase activities and transforming abilities of Abelson protein kinases that are cited in Example 1 below.

A related embodiment is a method of identifying a mutant Abelson protein tyrosine kinase expressed by a cell by determining a nucleotide sequence of a portion of a polynucleotide encoding the kinase domain of the Abelson protein tyrosine kinase expressed by the cell and then comparing the nucleotide sequence so determined to that of the wild type sequence of the Abelson protein tyrosine kinase to identify the presence of a mutation, wherein the mutation so identified has the characteristics of occurring at a amino acid residue located within the polypeptide sequence of the Abelson protein tyrosine kinase at the same relative position as a mutation in the C-Abl protein kinase shown in SEQ ID NO: 1 that has been identified as being associated with a resistance to an inhibition of tyrosine kinase activity by a 2-phenylaminopyrimidine, as determined using the homology parameters of a BLAST analysis (e.g. c-src position 338 which corresponds to position 315 in SEQ ID NO: 1). In a specific version of this embodiment, the cell expressing the mutant Abelson protein tyrosine kinase is found in a population of cancer cells that has been observed in clinical populations to exhibit a resistance to an inhibition of tyrosine kinase activity by a 2-phenylaminopyrimidine (e.g. STI-571). In a highly preferred embodiment the mutation in the C-Abl protein kinase shown in SEQ ID NO: 1 that has been identified as being associated with a resistance to an inhibition of tyrosine kinase activity by a 2-phenylaminopyrimidine is a Bcr-Abl residue identified in Table I.

Yet another embodiment of the invention is a method of identifying a mutant Abelson tyrosine kinase expressed by a cell by determining a nucleotide sequence of a portion of the catalytic domain of the Abelson tyrosine kinase expressed by the cell (and more preferably the nucleotide binding site within the catalytic domain) and then comparing the nucleotide sequence so determined to that of the wild type sequence of the catalytic domain of the Abelson protein tyrosine kinase to identify the presence of a mutation within the catalytic domain, wherein the mutation so identified has the characteristics of occurring at a amino acid residue located within the polypeptide sequence of the Abelson protein tyrosine kinase at a amino acid residue that has homology to an amino acid position in a C-Abl kinase shown in SEQ ID NO: 1 that is associated with a resistance to an inhibition of tyrosine kinase activity by a 2-phenylaminopyrimidine, wherein the homology between the amino acid residue located within the polypeptide sequence of the Abelson protein tyrosine kinase and the amino acid residue in the C-Abl kinase shown in SEQ ID NO: 1 that is associated with a resistance to an inhibition of tyrosine kinase activity by a 2-phenylaminopyrimidine can be illustrated via a BLAST analysis.

As used herein, an Abelson tyrosine kinase refers to the family of kinases known in the art to be closely related to the c-Abl protein or have domains that share a high degree of homology with a domain in the c-Abl protein. For example, the Philadelphia translocation is known to result in the expression of a family of chimeric proteins in which a portion of the Bcr protein is fused to c-Abl protein. A specific grouping of Abelson tyrosine kinase family members are those which exhibit an amino acid sequence homology that is structurally and/or functionally related such that a 2-phenylaminopyrimidine can interact with these molecules and inhibit their kinase activities (e.g. Bcr-Abl, TEL-Abl, c-kit, PDGFR, EGFR and VEGFR).

Another representative member of the Abelson tyrosine kinase family is the protein designated ARG. An analysis of the amino acid sequence of the ARG protein reveals that it is closely related to that of c-Abl (see, e.g., Kruh et al., PNAS 1990, 87(15): 5802-6 and Wang et al., Oncogene 1996, 13(7): 1379-85). Specifically, c-Abl and ARG are strikingly similar with regard to overall structural architecture as well as the amino acid sequences of their tyrosine kinase domains. Additional members of the family include for example, Dash, Nabl, and Fes/Fps (see e.g. Hunter et al., Science 241, 42-51 (1988)).

As is known in the art, the Abelson tyrosine kinase family of protein kinases contain a catalytic domain that has a highly conserved structural and functional architecture (see, e.g. Sicheri et al., Curr Opin Struct Biol. 1997 December; 7(6): 777-85; and Sicheri et al., Nature. 1997 Feb. 13; 385(6617): 602-9). Understandably, because regions within the catalytic domain of these tyrosine kinases are known to be highly conserved among members of this gene family, it is observed that STI-571 also interacts with representative members of this family such as c-kit and PDGFR (see, e.g., Tuveson et al., Oncogene. 2001 Aug. 16; 20(36):5054-8; Buchdunger et al., J Pharmacol Exp Ther. 2000 October; 295(1):139-45; Wang et al., Oncogene. 2000 Jul. 20; 19(31):3521-8; Heinrich et al., Blood. 2000 Aug. 1; 96(3):925-32; and Carroll et al., Blood. 1997 Dec. 15; 90(12):4947-52).

As noted above, the catalytic domains of these protein kinases have a highly conserved structural and functional architecture which allows for the interaction of compounds of the 2-phenylaminopyrimidine class of molecules to interact with this domain and further provides the basis for a variety of comparative analyses as well as rational drug design (see, e.g., Traxler et al., Med Res Rev. 2001 November; 21(6):499-512; Traxler et al., J Med Chem. 1999 Mar. 25; 42(6):1018-26; and Parang et al., Nat Struct Biol. 2001 January; 8(1):37-41 Singh et al., J Med Chem. 1997 Mar. 28; 40(7):1130-5 and Furet et al., J Comput Aided Mol Des. 1995 December; 9(6): 465-72. Moreover, because the crystal structure of the catalytic domain of Abl complexed 2-phenylaminopyrimidines such as variants of STI-571 has been determined, this provides information as to how this class of molecules interacts with these highly conserved regions within these kinases (see, e.g., Schindler et al., Science. 2000 Sep. 15; 289(5486):1938-42). Such analyses are enhanced by the fact that the crystal structures of a number of other tyrosine kinase inhibitors have also been determined (see, e.g., Schindler et al., Mol Cell. 1999 May; 3(5):639-48; Mohammadi et al., EMBO J. 1998 Oct. 15; 17(20):5896-904).

As disclosed herein, the domain comprising the ATP binding site is identified as a region that is mutated in Bcr-Abl proteins exhibiting resistance to STI-571. Interestingly, other chemical classes of TK inhibitors are known to bind the ATP binding site including quinazolines and pyrazolo-pyrrolo-pyridopyrimidines (see, e.g., Tian et al., Biochemistry. 2001 Jun. 19; 40(24):7084-91; Fry et al., Science. 1994 Aug. 19; 265(5175):1093-5; Rewcastle et al., J Med Chem. 1996 Feb. 16; 39(4):918-28; Rewcastle et al., J Med Chem. 1995 Sep. 1; 38(18):3482-7; Toledo et al., Curr Med Chem. 1999 September; 6(9):775-805; and Bridges et al., Curr Med Chem. 1999 September; 6(9):825-43). Consequently, TK inhibitors which bind an ATP binding site having a high homology to the ATP binding site of Bcr-Abl (and mutants exhibiting resistance to such inhibitors) can be analogously identified and characterized using the disclosure provided herein.

The invention provided herein identifies specific regions within conserved protein kinase family members that impart resistance to a class of tyrosine kinase inhibitors, thereby identifying these regions as the targets of the diagnostic protocols described herein. In particular, while certain amino acid residues known to be involved in an interaction with kinase inhibitors such as 2-phenylaminopyrimidines have been identified, it was not known whether a mutation could occur at a residue within a domain having a specific biological activity that would inhibit the interaction between the kinase and the kinase inhibitor yet allow the kinase to retain a biological activity associated with a pathological condition, particularly in cases where the mutation is observed in clinical specimens. The disclosure provided herein identifies specific target domains (e.g. the ATP-binding domain) within protein kinases in which amino acid mutations can occur that render the kinase resistant to kinase inhibitors such as 2-phenylaminopyrimidines yet allow the kinase to retain a biological activity that is associated with a pathological condition (e.g. chronic myeloid leukemia). By identifying a specific region in protein kinases in which mutations having these dual characteristics occur, the disclosure provided herein allows the skilled artisan to employ diagnostic procedures that are tailored to specifically analyze polynucleotides encoding these regions (e.g. in PCR protocols used to identify protein kinases likely to be resistant to kinase inhibitors). In this way, the disclosure provided herein can reduce the amount of experimentation necessary to characterize a mutant protein kinase that is associated with a pathological condition. Such analyses are facilitated by the fact that these target domains are so highly conserved among a variety of protein kinases they are readily identified, and therefore easily targeted in protocols used to identify the presence of such mutations in these domains.

Typical embodiments of the invention include a method of identifying a mutation in the catalytic domain of a target protein kinase comprising determining the amino acid sequence of the catalytic domain and comparing it to the wild type sequence of the target protein kinase catalytic domain to identify a mutation therein, wherein the catalytic domain of the target protein kinase has at least about 60, 70, 80, 85, 90 or 95% homology to the catalytic domain of c-able catalytic domain shown in SEQ ID NO: 1. A related embodiment is a method of identifying a mutation in the activation loop domain of a target protein kinase comprising determining the amino acid sequence of the activation loop domain and comparing it to the wild type sequence of the target protein kinase activation loop domain to identify a mutation therein, wherein the activation loop domain of the target protein kinase has at least about 60, 70, 80, 85, 90 or 95% homology to the activation loop domain of c-able activation loop domain shown in SEQ ID NO: 1. A related embodiment is a method of identifying a mutation in the nucleotide binding pocket of a target protein kinase comprising determining the amino acid sequence of the nucleotide binding pocket and comparing it to the wild type sequence of the target protein kinase nucleotide binding pocket domain to identify a mutation therein, wherein the nucleotide binding pocket domain of the target protein kinase has at least about 60, 70, 80, 85, 90 or 95% homology to the nucleotide binding pocket domain of c-able catalytic domain shown in SEQ ID NO: 1. A related embodiment is a method of identifying a mutation in a target tyrosine kinase that is likely to be associated with resistance to a tyrosine kinase inhibitor comprising determining the amino acid sequence of the P-loop, helix c, activation loop or catalytic sequences as well as sequences within about 10 amino acids of the respective domain(s), and comparing it to the wild type sequence of the target protein kinase P-loop, helix c, activation loop or catalytic sequences as well as sequences within about 10 amino acids of the respective domain(s) to identify a mutation therein, wherein the P-loop, helix c, activation loop or catalytic sequences as well as sequences within about 10 amino acids of the respective domain(s) of the target protein kinase has at least about 60, 70, 80, 85, 90 or 95% homology to the P-loop, helix c, activation loop or catalytic sequences as well as sequences within about 10 amino acids of these domains in c-Abl.

Another related embodiment is a method of isolating a polynucleotide encoding a mutated catalytic domain of a target protein kinase comprising employing PCR to amplify the catalytic domain of a target protein kinase, wherein the target protein kinase exhibits a biological activity that is associated with a pathological condition and wherein the target protein kinase exhibits a resistance to tyrosine kinase inhibitors, and wherein the catalytic domain of the target protein kinase has at least about 60, 70, 80, 85, 90 or 95% homology to the catalytic domain of c-able catalytic domain shown in SEQ ID NO: 1, comparing the polynucleotide sequence encoding the amino acid sequence of the catalytic domain and comparing it to the polynucleotide sequence encoding the amino acid sequence wild type amino acid sequence of the target protein kinase catalytic domain so that a polynucleotide encoding a mutated catalytic domain is identified.

In a specific embodiment of these methods, at least one amino acid residue that is mutated in the domain has homology to a residue identified in Table I. In another specific embodiment, the target protein kinase having the mutation exhibits a kinase activity that is associated with a pathological condition (e.g. cancer). In another specific embodiment, the kinase activity of the target protein kinase that is associated with a pathological condition (e.g. cancer) is resistant to inhibition by a tyrosine kinase inhibitor. In another specific embodiment, the kinase activity of the target protein kinase that is associated with a pathological condition (e.g. cancer) is resistant to inhibition by a 2-phenylaminopyrimidine. In another specific embodiment, the target protein kinase is shown in Table 2 of Hanks et al., Science 241: 42-51 (1988). In another specific embodiment, the target protein kinase is a Bcr-Abl, a TEL-Abl, a c-kit, a PDGFR, an EGFR, an VEGFR.

A related embodiment comprises a method of characterizing a property of a protein tyrosine kinase, wherein the protein kinase has at least about 60, 70, 80, 85, 90 or 95% homology to c-able shown in SEQ ID NO: 1 comprising determining whether the protein tyrosine kinase exhibits an activity that is associated with a pathological condition (e.g. via a procedure identified herein or citations in the art), determining whether the protein tyrosine kinase exhibits resistance to a tyrosine kinase inhibitor (e.g. via a procedure identified herein or citations in the art), determining an amino acid sequence of the protein tyrosine kinase, determining whether the amino acid sequence of the protein tyrosine kinase contains a mutated residue, determining whether the mutated residue occurs in the catalytic domain, the activation loop and/or the ATP binding domain and/or determining whether the mutated residue has homology to a residue shown in Table I, wherein the presence of a mutated residue occurring in the catalytic domain, the activation loop and/or the ATP binding domain and/or wherein the mutated residue has homology to a residue shown in Table I provides evidence that the mutation so identified inhibits the interaction between the kinase and the kinase inhibitor yet allow the kinase to retain its kinase activity. In a specific embodiment, the kinase activity of the protein kinase that is associated with a pathological condition is resistant to inhibition by a 2-phenylaminopyrimidine. In another specific embodiment, the protein kinase is a protein kinase shown in Table 2 of Hanks et al., Science 241: 42-51 (1988). In another specific embodiment, the protein kinase is a Bcr-Abl, a TEL-Abl, a c-kit, a PDGFR, an EGFR, an VEGFR.

Yet another embodiment of the invention is a method of identifying a mutant Abelson protein tyrosine kinase expressed by a mammalian cancer cell by determining a nucleotide sequence of a portion of a polynucleotide encoding the kinase domain of the Abelson protein tyrosine kinase expressed by the cell and then comparing the nucleotide sequence so determined to that of the wild type sequence of the Abelson protein tyrosine kinase to identify the presence of a amino acid substitution in the mutant Abelson protein tyrosine kinase, wherein any amino acid substitution so identified has the characteristics of occurring at a amino acid residue located within the polypeptide sequence of the Abelson protein tyrosine kinase at the same relative position as an amino acid substitution in the C-Abl protein kinase shown in SEQ ID NO: 1 that has been identified as being associated with a resistance to an inhibition of tyrosine kinase activity by a 2-phenylaminopyrimidine, as can be determined using the homology parameters of a WU-BLAST-2 analysis. In preferred embodiments of the invention, the mutant Abelson tyrosine kinase expressed by the cell is a mutant c-Abl (see, e.g. NCBI Accession P00519), Bcr-Abl (see, e.g. NCBI Accession NP_067585), PDGFR (see, e.g. NCBI Accession NP002600), c-kit (see, e.g. NCBI Accession CAA29458), TEL-Abl (see, e.g. NCBI Accession CAA84815), or TEL-PDGFR (see, e.g. NCBI Accession AAA19786). A related embodiment of the invention comprises repeating steps (a)-(b) another mammalian cancer cell obtained from a different individual; and then cataloging the mutations found in the mutant Abelson protein tyrosine kinases present in the mammalian cancer cells. Preferably in such methods, the cell expressing the mutant Abelson protein tyrosine kinase is found in a population of mammalian cancer cells that are observed to exhibit a resistance to an inhibition of tyrosine kinase activity after exposure to a 2-phenylaminopyrimidine. In such methods, the mammalian cancer cell is can be a human cancer cell obtained from an individual selected for treatment with a tyrosine kinase inhibitor comprising a 2-phenylaminopyrimidine. Preferably, the amino acid substitution confers resistance to inhibition of tyrosine kinase activity by a 2-phenylaminopyrimidine.

In a specific embodiment of such methods, the mutation in the C-Abl protein kinase shown in SEQ ID NO: 1 that has been identified as being associated with a resistance to an inhibition of tyrosine kinase activity by a 2-phenylaminopyrimidine occurs at the same relative position as amino acid residue D233, T243, M244, K245, G249, G250, G251, Q252, Y253, E255, V256L Y257, F259, K262, D263, K264, S265, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, or T406. Typically, the amino acid substitution occurs at the same relative position as amino acid residue G250, Q252, E255, K264, V270, F283, M290, P296, V304, T315, F317, R328, M343, M343, A344, M351T, E35, K357, I360, V379 or H396.

The disclosure provided herein allows a mutant identified by one the methods disclosed herein to be further characterized. Specifically, by utilizing enzymological and/or biological assays described herein as well as those known in the art (illustrated by those disclosed, for example, in the Examples below), a mutant that is found to occur in a conserved target domain of a protein kinase can be readily characterized to assess the biological significance of this mutation (e.g. rendering the protein kinase resistant to kinase inhibitors such as 2-phenylaminopyrimidines yet allowing the kinase to retain a biological activity that is associated with a pathological condition). Moreover, in the context of proteins in which a target protein is identified, the disclosure herein of assays for the measurement of the phosphotyrosine content in an analogous fashion to the assays of Crkl, an adaptor protein which is specifically and constitutively phosphorylated by Bcr-Abl in CML cells (see, e.g., FIGS. 1 and 2).

In addition to the mutations identified in Table I, scanning amino acid analysis can also be employed in comparative analyses of compounds such as 2-phenylaminopyrimidines to identify the significance of one or more amino acids which are structurally and/or functionally involved in the interaction between Abelson tyrosine kinases and compounds such as 2-phenylaminopyrimidines (see, e.g. U.S. Pat. Nos. 6,004,931 and 5,506,107). Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, J. Mol. Biol., 150:1 (1976)]. If alanine substitution does not yield adequate amounts of variant, an isosteric amino acid can be used.

Identification of Molecules that Interact with MARS

As illustrated in Example 8, the MARS protein and nucleic acid sequences disclosed herein allow a skilled artisan to identify proteins, small molecules and other agents that interact with MARS, as well as pathways activated by MARS via any one of a variety of art accepted protocols. For example, using the disclosure provided herein, one can employ methods used in the art to evaluate the interaction between STI-571 and Bcr-Abl to evaluate interactions between test molecules and MARS.

A representative embodiment of this invention comprises a method of screening for a molecule that interacts with an MARS amino acid sequence comprising the steps of contacting a population of molecules with the MARS amino acid sequence, allowing the population of molecules and the MARS amino acid sequence to interact under conditions that facilitate an interaction, determining the presence of a molecule that interacts with the MARS amino acid sequence, and then separating molecules that do not interact with the MARS amino acid sequence from molecules that do. In a specific embodiment, the method further comprises purifying a molecule that interacts with the MARS amino acid sequence. The identified molecule can be used to modulate a function performed by MARS.

This embodiment of the invention is well suited to screen chemical libraries for molecules which modulate, e.g., inhibit, antagonize, or agonize or mimic, the activity of BCR-ABL as measured by one of the assays disclosed herein. The chemical libraries can be peptide libraries, peptidomimetic libraries, chemically synthesized libraries, recombinant, e.g., phage display libraries, and in vitro translation-based libraries, other non-peptide synthetic organic libraries (e.g. libraries of 2-phenylaminopyrimidines, quinazolines or pyrazolo-pyrrolo-pyridopyrimidines and the like etc.).

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Chemical (synthetic) libraries, recombinant expression libraries, or polysome-based libraries are exemplary types of libraries that can be used.

In one embodiment, one can screen peptide libraries to identify molecules that interact with MARS protein sequences. In such methods, peptides that bind to a molecule such as MARS are identified by screening libraries that encode a random or controlled collection of amino acids. Peptides encoded by the libraries are expressed as fusion proteins of bacteriophage coat proteins, the bacteriophage particles are then screened against the protein of interest.

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with MARS protein sequences are disclosed for example in U.S. Pat. No. 5,723,286 issued 3 Mar. 1998 and U.S. Pat. No. 5,733,731 issued 31 Mar. 1998.

Small molecules and ligands that interact with MARS can be identified through related embodiments of such screening assays. For example, small molecules can be identified that interfere with protein function, including molecules that interfere with a MARS's ability to mediate phosphorylation and de-phosphorylation.

A typical embodiment is a method of identifying a compound which specifically binds a MARS shown in Table I, wherein said MARS exhibits tyrosine kinase activity, comprising the steps of contacting said MARS with a test compound under conditions favorable to binding; and then determining whether said test compound binds to said MARS so that a compound which binds to said MARS can be identified. As the interaction between various Abelson tyrosine kinases and a variety of test compounds have been previously described, skilled artisans are familiar with the conditions conducive to binding. A specific embodiment of this aspect of the invention includes the steps of transfecting cells with a construct encoding the MARS, contacting said cells with said test compound that is tagged or labelled with a detectable marker and then analyzing said cells for the presence bound test compound. In contexts where the transfected cells are observed to preferentially bind the test compound as compared to cells that have not been transfected with a MARS construct, this indicates that the test compounds is binding to the MARS protein expressed by those cells.

A test compound which binds said MARS may then be further screened for the inhibition of a biological activity (e.g. tyrosine kinase activity) of said MARS. Such an embodiment includes, for example determining whether said test compound inhibits the tyrosine kinase activity of the MARS by utilizing molecular biological protocols to create recombinant contracts whose enzymological and biological properties can be examined directly. A specific biological activity such as resistance to STI-571 can be measured using standard kinase assays and transformation assays. Enzymology is performed for example, by measuring tyrosine kinase activity in vitro or in MARS expressing cells using standard assays (see, e.g. one of those cited in the Examples below). Alternatively, biological activity is measured using standard oncogene transformation assays (see, e.g. one of those cited in the Examples below).

A specific embodiment of the invention entails determining whether a test compound inhibits the biological activity of a MARS tyrosine kinase inhibitor in a procedure that is analogous for examining how STI-571 inhibits the tyrosine kinase activity of Bcr-Abl. Such methods typically comprise the steps of examining the kinase activity or growth potential of a MARS expressing cell line in the absence of a test compound and comparing this to the kinase activity or growth potential of a MARS expressing cell line in the presence of a test compound, wherein an decrease in the kinase activity or growth potential of the MARS expressing cell line in the presence of a test compound indicates that said compound may be an inhibitor of the biological activity of said MARS.

Yet another embodiment of the invention is a method of identifying a compound which specifically binds a mutant Bcr-Abl polypeptide; wherein the Bcr-Abl polypeptide comprises an amino acid substitution that occurs in a region of the Bcr-Abl polypeptide sequence shown in SEQ ID NO: 1 comprising residue D233 through residue T406, the method comprising the steps of: contacting the mutant Bcr-Abl polypeptide with a test compound under conditions favorable to binding; and determining whether the test compound specifically binds to the mutant Bcr-Abl polypeptide such that a compound which binds to the mutant Bcr-Abl polypeptide can be identified. The binding of the compound is typically determined by any one of a wide variety of assays known in the art such as ELISA, RIA, and/or BIAcore assays.

In preferred embodiments, the amino acid substitution in the mutant Bcr-Abl polypeptide occurs at residue D233, T243, M244, K245, G249, G250, G251, Q252, Y253, E255, V256L Y257, F259, K262, D263, K264, S265, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, or T406. In a specific embodiment of the invention, the amino acid substitution is D233H, T243S, M244V, G249D, G250E, G251S, Q252H, Y253F, Y253H, E255K, V256L, Y257F, Y257R, F259S, K262E, D263G, K264R, S265R, V268A, V270A, T272A, Y274C, Y274R, D276N, T277P, M278K, E282G, F283S, A288T, A288V, M290T, K291R, E292G, I293T, P296S, L298M, L298P, V299L, Q300R, G303E, V304A, V304D, C305S, C305Y, T306A, F311L, I314V, T315A, T315I, E316G, F317L, M318T, Y320C, Y320H, G321E, D325H, Y326C, L327P, R328K, E329V, Q333L, A337V, V339G, L342E, M343V, M343T, A344T, A344V, I347V, A350T, M351T, E352A, E352K, E355G, K357E, N358D, N358S, F359V, I360K, I360T, L364H, E373K, N374D, K378R, V379I, A380T, A380V, D381G, F382L, T389S, T392A, T394A, A395G, H396K, A399G, P402T or T406A.

A related embodiment of the invention consists of the method described above and further comprising determining whether the test compound inhibits the tyrosine kinase activity of the mutant Bcr-Abl polypeptide by transfecting mammalian cells with a construct encoding the mutant Bcr-Abl polypeptide, contacting the mammalian cells with the test compound; and then monitoring the mammalian cells for the tyrosine kinase activity of the mutant Bcr-Abl polypeptide, wherein an inhibition in tyrosine kinase activity in the presence of the test compound as compared to the absence of the test compound identifies the test compound as an inhibitor of the mutant Bcr-Abl polypeptide. In preferred embodiments of the invention the tyrosine kinase activity of the mutant Bcr-Abl polypeptide is measured by examining the phosphotyrosine content of Crkl.

As illustrated in the Examples below, yet another embodiment of the invention is a method of determining whether a test compound inhibits the tyrosine kinase activity of a mutant Bcr-Abl polypeptide, wherein the Bcr-Abl polypeptide comprises an amino acid substitution that occurs in a region of the Bcr-Abl polypeptide sequence shown in SEQ ID NO: 1 comprising residue D233 through residue T406, the method comprising the steps of transfecting mammalian cells (e.g. 293-T cells) with a construct encoding the mutant Bcr-Abl polypeptide so that the mutant Bcr-Abl polypeptide is expressed by the mammalian cells, contacting the mammalian cells with the test compound and then monitoring the mammalian cells for the tyrosine kinase activity of the mutant Bcr-Abl polypeptide, wherein an inhibition in tyrosine kinase activity in the presence of the test compound as compared to the absence of the test compound identifies the test compound as an inhibitor of the mutant Bcr-Abl polypeptide. In specific embodiments of the invention, the amino acid substitution occurs at residue D233, T243, M244, K245, G249, G250, G251, Q252, Y253, E255, V256L Y257, F259, K262, D263, K264, S265, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, or T406.

Preferably in such methods, the tyrosine kinase activity of the mutant Bcr-Abl polypeptide is measured by examining the phosphotyrosine content of Crkl. Alternatively, the tyrosine kinase activity of the mutant Bcr-Abl polypeptide is measured via Western blot analysis using an anti-phosphotyrosine antibody to examine the phosphotyrosine content of lysates of the mammalian cells. These methods can be used to examine a wide variety of compounds such as 2-phenylaminopyrimidines or pyrido[2,3-d]pyrimidines.

Typically the amino acid substitution occurs at residue G250, Q252, E255, K264, V270, F283, M290, P296, V304, T315, F317, R328, M343, M343, A344, M351T, E35, K357, I360, V379 or H396. In certain embodiments of the invention, the amino acid substitution does occur at one of the residues identified in Table IA (e.g. residue T315) but not another of the residues identified in Table IA (e.g. residue E255).

Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a MARS protein or a MARS gene or message, respectively. Where the kit utilizes nucleic acid hybridization to detect the target nucleic acid, the kit may also have containers containing nucleotide(s) for amplification of the target nucleic acid sequence and/or a container comprising a reporter means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

EXAMPLES

Example 1

Illustrative Materials and Methods for Examining BCR-ABL

In an illustrative strategy for examining MARS, our laboratory has embarked on a large scale sequencing project to identify mutations in the ABL kinase domain in patients with chronic myeloid leukemia. A preferred experimental strategy is to use PCR to amplify a region of the BCR-ABL transcript using primers specific to BCR and ABL, subclone this product and sequence at least 10 independent clones in both directions. This strategy allows one to quantify fluctuations in different clones from the same patient over time. Several different groups of patients have been analyzed in order to determine if the frequency and type of ABL mutation differs with disease stage or prior treatment. These groups include: chronic phase untreated with STI-571 (Gleevec), chronic phase treated with STI-571, blast crisis untreated with STI-571 and blast crisis treated with STI-571. Using this strategy we have found over 40 such mutations. Typical methodologies are for such protocols are provided below.

Example 1A

Figure 8:
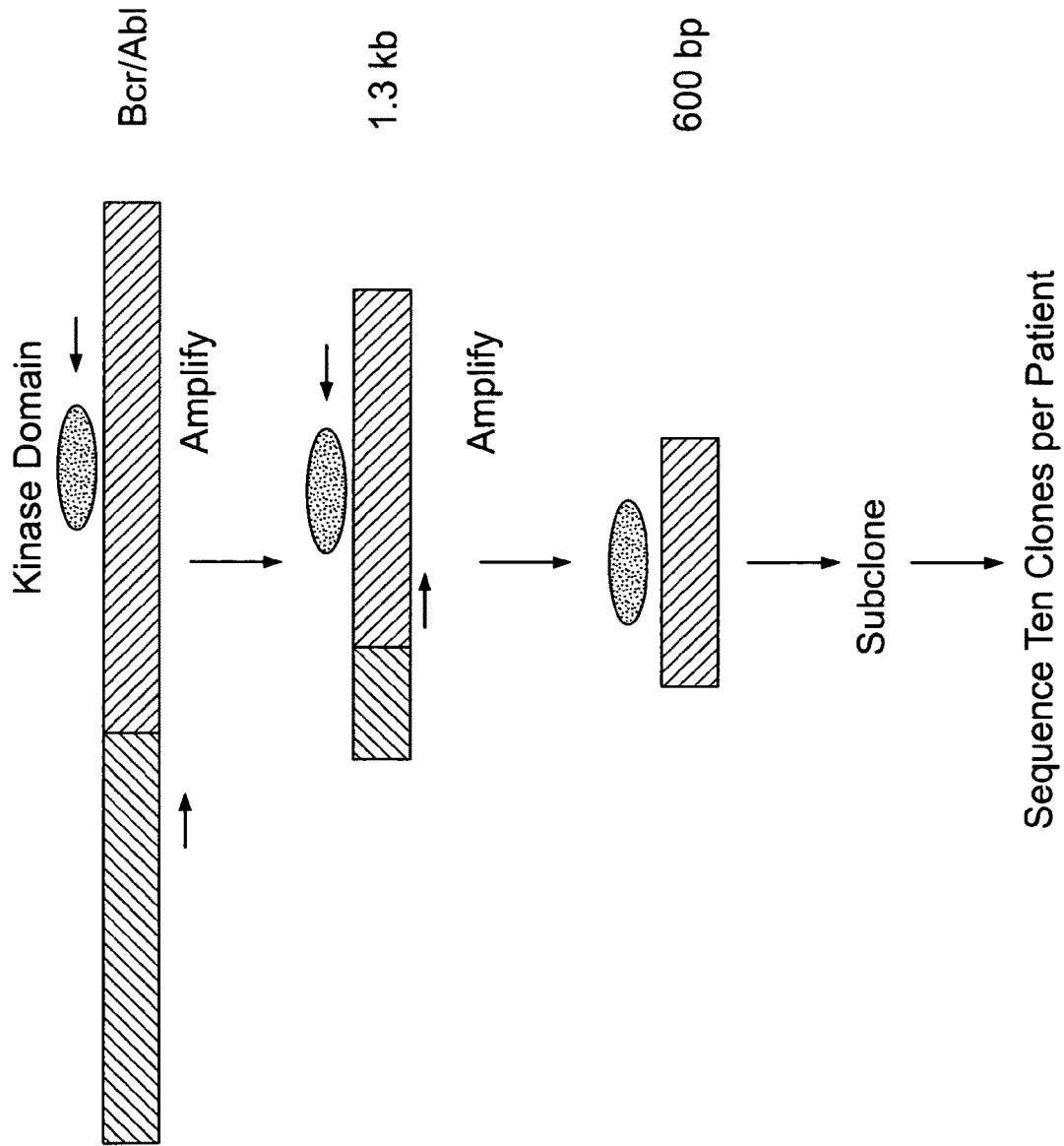
FIG. 8. Schematic of Bcr-Abl kinase domain sequencing methodology. Bcr-Abl cDNA is represented with Bcr sequences stippled, and Abl sequences in black. Horizontal arrows represent PCR primers. Initial PCR results in amplification of a 1.3 kb Bcr-Abl subfragment which serves as template for a second round PCR of the kinase domain which is then subcloned. Ten independent clones per patient time point were sequenced. Sequence deviations from wild-type Bcr-Abl observed in at least two of ten clones were considered mutations.

Illustrative Methods for Examining BCR-ABL Polynucleotide and Polypeptide Sequences Blood samples were obtained from consenting patients enrolled in clinical trials at UCLA assessing the efficacy of STI-571 in the treatment of CML. RNA was extracted using TriReagent or TriAzol. cDNA synthesis was performed using MMTV reverse transcriptase. Polymerase chain reaction (PCR) was performed using the following primers: CM10 (5'-GAAGCTTCTCCCTGACATCCGT-3') (SEQ ID NO: 6) and 3' Abl KD (5'-GCCAGGCTCTCGGGTGCAGTCC-3') (SEQ ID NO: 7). The resultant 1.3 kb fragment was excised from a low melting point agarose gel following electrophoresis. A second PCR was performed on the gel-purified 1.3 kb fragment to isolate the kinase domain using the primers 5' Abl KD (5'-GCGCAACAAGCCCACTGTCTATGG-3') (SEQ ID NO: 8) and 3' Abl KD. The resultant 0.6 kb fragment was ligated into pBluescript II KS+ digested with Eco RV. Bacterial transformants were plated on media containing ampicillin and X-gal. Ten white colonies per cDNA were inoculated into media and miniprep DNA was isolated. Sequencing of each clone was performed using M13 universal forward and reverse primers. Because two rounds of amplification were employed, a mutation was considered present if it was detected on both strands of at least two independent clones per patient (see FIG. 8). Analysis of the Abl kinase domain from two healthy blood donors was performed using PCR of the Abl kinase domain, followed by subsequent reamplification to control for the number of amplification cycles to which patient samples were subjected. Sequence analysis of a 0.7 kb portion of Bcr-Abl immediately 5' to the kinase domain was performed by amplification of the previously described 1.3 kb fragment using CM10 and 5' Abl KD reverse complement (5'-CCATAGACAGTGGGCTTGTTGCGC-3') (SEQ ID NO: 9) followed by ligation into pBluescript II KS+ as above. The kinase domain of c-Kit was amplified using the following primers: (5'-TGAGGAGATAAATGGAAACAA-3') (SEQ ID NO: 10) and (5'-AACTCGTCATCCTCCATGAT-3') (SEQ ID NO: 11). To control for the number of cycles used for the Bcr-Abl kinase domain, a second amplification was performed; the resultant 0.6 kb fragment was subcloned into pBluescript II KS+ and ten independent colonies were sequenced.

Expression vectors of mutant P210 isoforms were created as follows. Oligonucleotides containing various point mutations were synthesized by Gibco/BRL. PSRalphaP210Bcr-Abl was used as the template DNA for site-directed mutagenesis reactions utilizing the mutant oligonucleotides and the QuikChange mutagenesis kit (Stratagene). Successful mutagenesis was confirmed by sequence analysis of the kinase domain. Other P210 abl constructs are known in the art (see, e.g. Sun et al., Cancer Res. 2002, 62(11): 3175-3183; Dugray et al., Leukemia 2001 15(10): 1658-1662; and Heisterkamp et al., Transgenic Res. 1991 1(1): 45-53).

293-T cells were co-transfected with mutant P210 expression vectors and a packaging plasmid (Ecopack, kindly provided by R. van Etten). Media containing virus was used to infect Ba/F3 cells. Stable lines were selected in the presence of G418 and IL-3. Subsequently, IL-3 was removed from the media. Expression of Bcr-Abl was document by Western blot analysis. To determine the biochemical sensitivity of mutant P210 isoforms to STI-571, cells were incubated in the presence of STI-571 (kindly provided by Novartis, Switzerland) at 0, 0.5, 1, 5, and 10 micromoles per liter. After two hours of incubation, cell lysates were prepared in 1% Triton. Western blot analysis using AB-3 (Oncogene Research Products) or 4G10 Upstate Biochemicals) was performed. To determine the biological sensitivity to STI-571, Ba/F3 cells expressing various isoforms of P210 were incubated in the presence of STI-571 kindly provided by Novartis, Switzerland) at 0, 0.5, 1, 5, and 10 micromoles per liter. After 24 hours of incubation, live cells were quantitated by trypan blue stain exclusion.

Example 1B

Illustrative Methods for Examining Discreet Regions in BCR-ABL

In certain contexts, it may be desirable to amplify a specific region in BCR-ABL such as one of the functional domains discussed herein. In this context, a 579 base pair region corresponding to the ATP-binding pocket and the activation loop of the kinase domain of Bcr-Abl was sequenced in the 9 patients for whom RNA was available at the time of relapse (FIG. 4A). Briefly, RNA was extracted from purified peripheral blood or bone marrow cells with Trireagent-LS (Molecular Research Center, Inc., Cincinnati, Ohio). 2 mg of total RNA was subjected to RT-PCR using Oligo dT primers. A 1327-bp cDNA fragment was amplified by PCR with a 5' BCR-specific primer (5'-GAAGCTTCTCCCTGGCATC-CGT-3') (SEQ ID NO: 6) and a 3' ABL-specific primer (5'-GCCAGGCTCTCGGGTGCAGTCC-3') (SEQ ID NO: 7). In two patients, the BCR-ABL fragment could not be amplified; therefore, a 579-bp fragment was amplified using an alternative 5' ABL-specific primer (5'-GCGCAACAAGCCCACT- GTCTATGG-3') (SEQ ID NO: 8) and the same 3' ABL primer. PCR products were cloned into the pCR2.1 TA cloning vector (Invitrogen, Carlsbad, Calif.). Both strands of a 579-bp region were sequenced with the 5' ABL primer and M13 forward primer or M13 forward and reverse primer set for the 1327-bp and the 579-bp fragments, respectively, on an ABI prism 377 automated DNA sequencer (PE Applied Biosystems, Foster City, Calif.). Sequence analysis was performed using the ClustalW alignment algorithm). A single, identical C→T nucleotide change was detected at ABL nucleotide 944 in six of nine cases examined (FIG. 4A). In all six patients a mixture of wild-type and mutant cDNA clones were found, with the frequency of mutant clones ranging from 17% to 70%. The mutation was found in three of three patients with lymphoid disease and in three of six patients with myeloid blast crisis. The presence of the mutation was confirmed by analysis of genomic DNA (FIG. 4A). Briefly, genomic DNA was extracted from purified bone marrow or peripheral blood cells with the QiaAMP Blood Mini Kit (Qiagen, Inc., Valencia, Calif.). A 361-bp DNA fragment was amplified by PCR with two primers (5'-GCAGAGTCAGAATCCTTCAG-3' (SEQ ID NO: 2) and 5'-TTTGTAAAAGGCTGCCCGGC-3' (SEQ ID NO: 3) which are specific for intron sequences 5' and 3' of ABL exon 3, respectively. PCR products were cloned and sequenced. Analysis of RNA or genomic DNA from pre-treatment samples failed to provide evidence of the mutation prior to STI-571 therapy; however, we cannot rule out the possibility that rare cells bearing the mutation exist prior to treatment.

Example 2

Illustrative Methods for Measuring of BCR-ABL Kinase Activity Via the Phosphotyrosine Content of CRKL Although the enzymatic activity of Bcr-Abl protein is readily measured in cell lines (e.g. via one of the assays discussed herein below), at times such assays can be difficult to perform in a reproducible, quantitative fashion with clinical materials because Bcr-Abl is subject to rapid degradation and dephosphorylation upon cell lysis. In a search for alternative measures of Bcr-Abl kinase activity, we found that the phosphotyrosine content of Crkl, an adaptor protein which is specifically and constitutively phosphorylated by Bcr-Abl in CML cells (see, e.g. J. ten Hoeve et al., Blood 84, 1731 (1994); T. Oda et al., J. Biol. Chem. 269, 22925 (1994); and G. L. Nichols et al., Blood 84, 2912 (1994)), could be measured reproducibly and quantitatively in clinical specimens. Crkl binds Bcr-Abl directly and plays a functional role in Bcr-Abl transformation by linking the kinase signal to downstream effector pathways (see, e.g. K. Senechal et al., J. Biol. Chem. 271, 23255 (1996)). When phosphorylated, Crkl migrates with altered mobility in SDS-PAGE gels and can be quantified using densitometry. As expected, Crkl phosphorylation in primary CML patient cells was inhibited in a dose-dependent manner when exposed to STI-571 and correlated with dephosphorylation of Bcr-Abl (FIG. 1A). This Crkl assay allows for an assessment of the enzymatic activity of Bcr-Abl protein in a reproducible, quantitative fashion in clinical materials.

Briefly, cells are lysed in 1% Triton X-100 buffer with protease and phosphatase inhibitors (see, e.g. A. Goga et al., Cell 82, 981 (1995)). Equal amounts of protein, as determined by the BioRad DC protein assay (Bio-Rad Laboratories, Hercules, Calif.), are separated by SDS-PAGE, transferred to nitrocellulose and immunoblotted with phosphotyrosine antibody (4G10, Upstate Biotechnologies, Lake Placid, N.Y.), Abl antibody (pex5, (see, e.g. A. Goga et al., Cell 82, 981 (1995)), β-actin antibody (Sigma Chemicals, St. Louis, Mo.) or Crkl antiserum (Santa Cruz Biotechnology, Santa Cruz, Calif.). Immunoreactive bands are visualized by ECL (Amersham Pharmacia Biotech, Piscataway, N.J.). Several exposures are obtained to ensure linear range of signal intensity. Optimal exposures are quantified by densitometry using ImageQuant software (Molecular Dynamics, Sunnyvale, Calif.)).

Figure 1B:
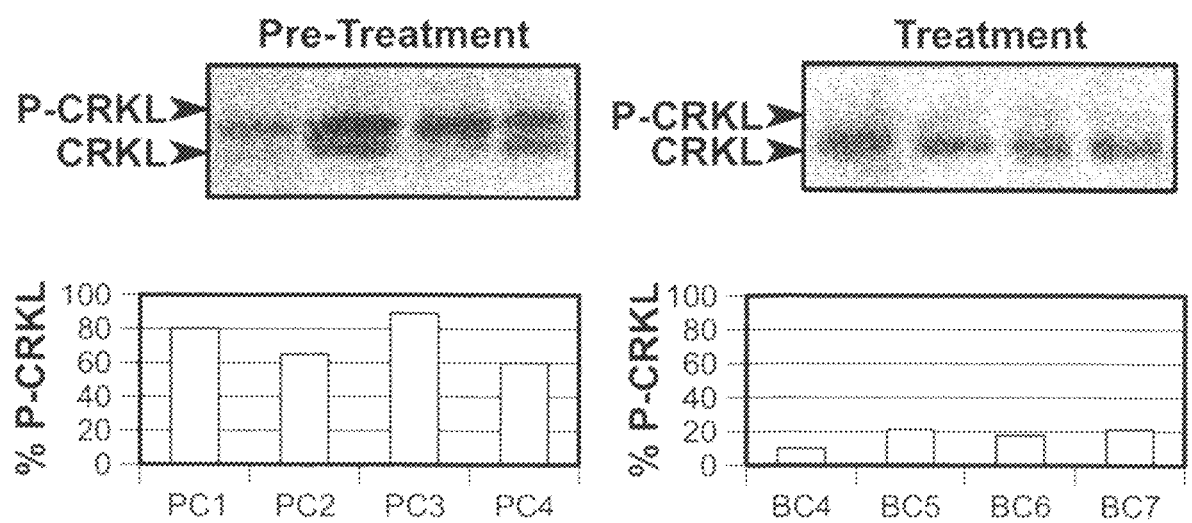
Figure 1C:
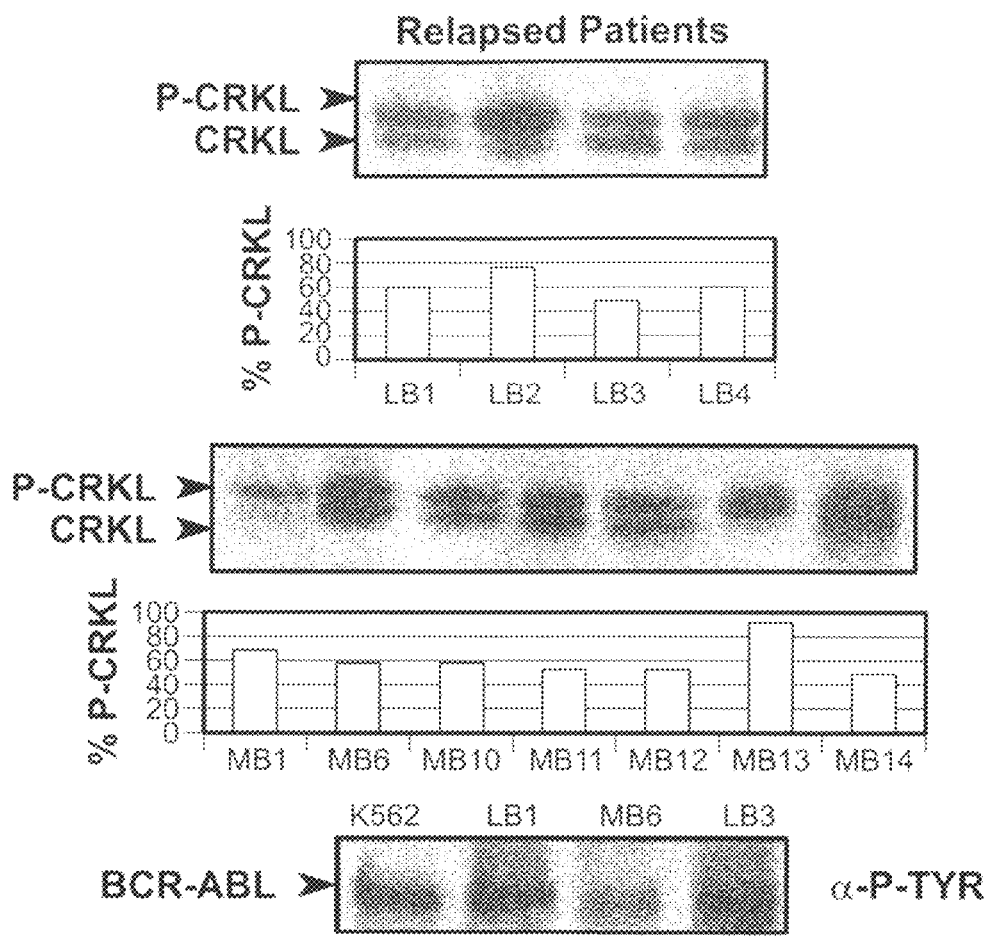
Figure 1D:
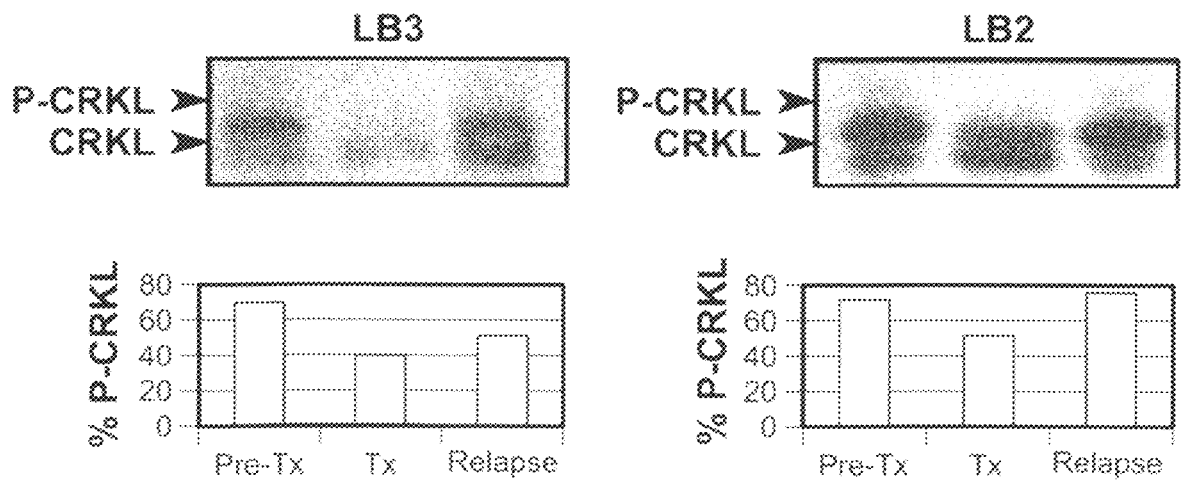

To establish the dynamic range of this assay in patient material, we measured Crkl phosphorylation in cells from BCR-ABL-negative individuals (n=4), untreated CML patients (n=4), as well as from patients who responded to STI-571 therapy but whose bone marrow cells remained 100% Ph-chromosome-positive (n=8). The mean level of Crkl phosphorylation in cells from CML patients prior to STI-571 treatment was 73±13.3% (FIG. 1B). At the time of response the mean was 22±9.9% (FIG. 1B), similar to the mean level of Crkl phosphorylation in cells from BCR-ABL-negative individuals (22±6.0%) (see, e.g. M. E. Gorre, C. L. Sawyers). We next measured levels of Crkl phosphorylation in primary leukemia cells from 11 patients who responded to STI-571 but subsequently relapsed on treatment. In these cases, which included one patient with lymphoid blast crisis, three with Ph+ acute lymphoid leukemia, and seven with myeloid blast crisis, the mean level of Crkl phosphorylation at relapse was 59±12.5% (FIG. 1C). Anti-phosphotyrosine immunoblot analysis of a subset of these samples confirmed that Bcr-Abl was phosphorylated on tyrosine at relapse (FIG. 1C). Longitudinal analysis of blood or bone marrow samples obtained from a subset of these patients before and throughout the course of STI-571 treatment confirmed that Crkl phosphorylation fell during the response to treatment, but increased at the time of relapse (FIG. 1D). Therefore, disease progression in patients who initially respond to STI-571 is associated with failure to maintain effective inhibition of Bcr-Abl kinase activity.

Example 3

Figure 3A:
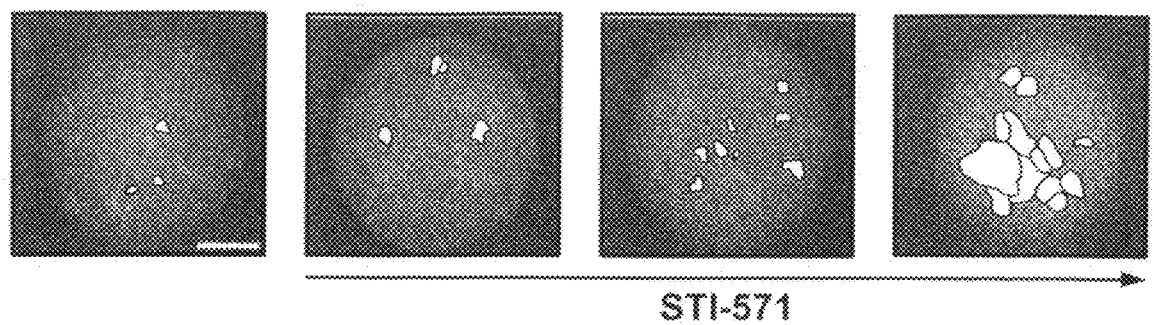
FIG. 3. BCR-ABL amplification in patients who relapsed after an initial response to STI-571. (A) BCR-ABL FISH analyses of interphase nuclei from blast crisis patient M13 prior to and during STI-571 therapy. Nuclei are visualized with DAPI stain (blue), ABL probe is labeled with Spectrum Orange (red signal) and BCR probe is labeled with Spectrum Green (green signal). BCR-ABL gene fusions, indicated by yellow signals, show an increase in BCR-ABL gene amplification during STI-571-resistant disease progression. (Bar=10μ. (B) BCR-ABL FISH analyses of interphase nuclei from blast crisis patient M14 prior to, during, and after removal from STI-571 therapy showing BCR-ABL-amplified phenotype and reversion to non-amplified phenotype upon removal from STI-571 therapy. (Bar=10μ. (C) Giemsa stained image (left panel; Bar=5μ) and dual color FISH images (middle and right panels; Bars=3μ of sample from patient LB1 showing duplicated inverted Ph-chromosome. Arrows indicate BCR-ABL gene fusions. (D) Quantitative PCR analysis of genomic DNA from BCR-ABL-amplified patients (MB13, MB14, LB1) and one non-amplified patient LB3 (control) confirming increased ABL gene copy number in all three patients.
Figure 3B:
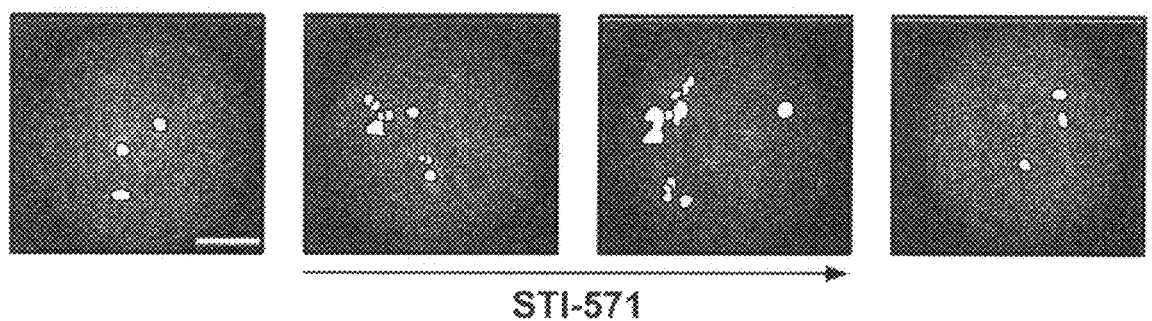
Figure 3C:
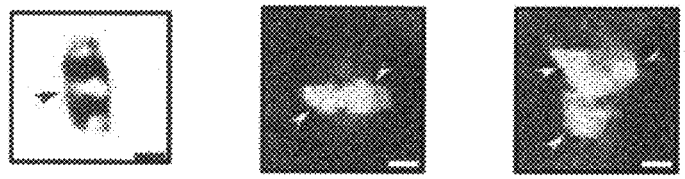

Illustrative Methods for Examining Amplification of the BCR-ABL Gene in Mammalian Cells Some CML cell lines that develop resistance to STI-571 after months of in vitro growth in sub-therapeutic doses of the drug have amplification of the BCR-ABL gene (see, e.g. E. Weisberg et al., Blood 95, 3498 (2000); P. le Coutre et al., Blood 95, 1758 (2000); and F. X. Mahon et al., Blood 96, 1070 (2000)). We performed dual-color fluorescence in situ hybridization (FISH) experiments to determine if BCR-ABL gene amplification could be similarly implicated in STI-571 resistance in human clinical samples. Briefly, interphase and metaphase cells were prepared (see, e.g. E. Abruzzese et al., Cancer Genet. Cytogenet. 105, 164 (1998)) and examined using Locus Specific Identifier (LSI) BCR-ABL dual color translocation probe (Vysis, Inc., Downers Grove, Ill.)). Multiple copies of the BCR-ABL gene were detected in interphase nuclei in three (two myeloid blast crisis, one lymphoid blast crisis) of the patients who relapsed after initially responding to STI-571 (FIG. 3). Further cytogenetic and FISH characterization of metaphase spreads from these patients showed a unique inverted duplicate Ph-chromosome with interstitial amplification of the BCR-ABL fusion gene (FIG. 3C). In one patient, the inverted duplicate Ph-chromosome could be detected prior to the initiation of STI-571. In all three cases, additional copies of the aberrant Ph-chromosome were observed as STI-571 treatment continued, as well as ring chromosomes harboring multiple copies of the BCR-ABL. Patient MB14 was reevaluated by FISH one month after receiving alternative treatment for her leukemia. Strikingly, BCR-ABL amplification was no longer detectable 4 weeks after discontinuation of STI-571, raising the possibility that persistent STI-571 administration might select for increased copies of the BCR-ABL gene in some patients.

Figure 3D:
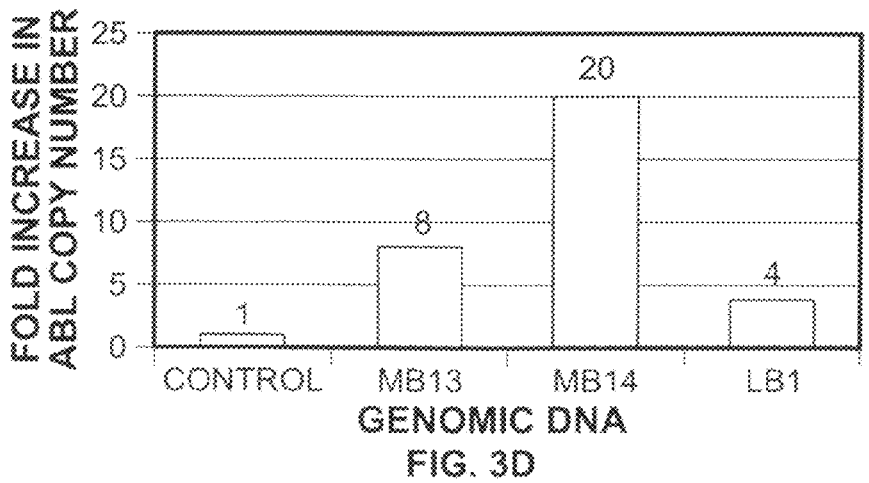

Quantitative PCR analysis of genomic DNA obtained from these three patients confirmed increased ABL gene copy number at relapse when compared to a patient without BCR-ABL gene amplification (FIG. 3D). Briefly, genomic DNA was extracted from purified bone marrow or peripheral blood cells with the QiaAMP Blood Mini Kit (Qiagen, Inc., Valencia, Calif.). 10 ng of total genomic DNA was subjected to real-time PCR analysis with the iCycler iQ system (Bio-Rad Laboratories, Hercules, Calif.). A 361-bp gDNA fragment including ABL exon 3 was amplified using two primers (5'-GCAGAGTCAGAATCCTTCAG-3' (SEQ ID NO: 2) and 5'-=TGTAAAAGGCTGCCCGGC-3' (SEQ ID NO: 3)) which are specific for intron sequences 5' and 3' of ABL exon 3, respectively. A 472-bp gDNA fragment of glyceraldehyde-3-phosphate dehydrogenase (GAPDH) was amplified using two primers (5'-TTCACCACCATGGAGAAGGC-3' (SEQ ID NO: 4) and 5'-CAGGAAATGAGCTTGACAAA-3' (SEQ ID NO: 5)) which are specific for sequences in exon 5 and exon 8 of GAPDH, respectively. Fold increase in ABL copy number was determined by calculating the difference between threshold cycle numbers of ABL and GAPDH for each sample (DCt). Using control LB3 as reference sample, DCt from each sample was subtracted from DCt of control to determine D(DCt). Fold increase was calculated as $2^{-D(DCt)}$.

Example 4

Art Accepted Methods for Measuring Enzymological and Biological Properties of BCR-ABL Mutants A variety of assays for measuring the enzymological properties of protein kinases such as Abl are known in the art, for example those described in Konopka et al., Mol Cell Biol. 1985 November; 5(11):3116-23; Davis et al., Mol Cell Biol. 1985 January; 5(1):204-13; and Konopka et al., Cell. 1984 July; 37(3):1035-42 the contents of which are incorporated herein by reference. Using such assays the skilled artisan can measure the enzymological properties of mutant BCR-Abl protein kinases.

A variety of bioassays for measuring the transforming activities of protein kinases such as Abl are known in the art, for example those described in Lugo et al., Science. 1990 Mar. 2; 247(4946):1079-82; Lugo et al., Mol Cell Biol. 1989 March; 9(3):1263-70; Klucher et al., Blood. 1998 May 15; 91(10):3927-34; Renshaw et al., Mol Cell Biol. 1995 March; 15(3):1286-93; Sirard et al., Blood. 1994 Mar. 15; 83(6): 1575-85; Laneuville et al., Cancer Res. 1994 Mar. 1; 54(5): 1360-6; Laneuville et al., Blood. 1992 Oct. 1; 80(7):1788-97; Mandanas et al., Leukemia. 1992 August; 6(8):796-800; and Laneuville et al., Oncogene. 1991 February; 6(2):275-82 the contents of which are incorporated herein by reference. Using such assays the skilled artisan can measure the phenotype of mutant BCR-Abl protein kinases.

Using protocols known in the art we have shown that T315I and E255K both retain potent kinase activity and can confer growth factor independence in BaF3 murine hematopoietic cells. This mutant is resistant to inhibition by STI-571 in kinase assays and in growth assays. Other mutants can be similarly studied using such analyses.

Example 5

Additional Illustrative Analytical Schemes for Characterizing the Functional Importance of BCR-ABL Mutations In addition to the methods described above, skilled artisans can undertake additional analyses of one or more BCR-ABL mutants such as those identified in Table I. For example, typical illustrative algorithms such as those whose parameters are outlined below can be used to characterize the clinical importance of the various mutations found in the kinase domain.

In a first illustrative method, one can examine samples from the same patient obtained at different times during their disease progression. Clones which become dominant over time may be presumed to have a growth advantage. This advantage could, for example be a consequence of increased potency of the BCR-ABL oncogene or resistance to a drug treatment such as STI-571 (as demonstrated by the T315I mutation). In addition, mutations which appear more commonly can be given priority.

In a second illustrative method, one can examine the location of the mutation in the context of the crystal structure of the ABL kinase domain (which has been solved bound to STI-571). This structure allows one to postulate whether the mutation might interfere with the anti-leukemia activity of STI-571. Based on this analysis, one can prioritize mutations for direct experimental analysis of ABL kinase activity, leukemogenicity and level of inhibition by STI-571.

In yet another illustrative method, one can engineer selected mutations into wild-type BCR-ABL cDNA to create a mutant allele whose enzymological and biological properties can be examined directly (see, e.g. Example 1 above). Enzymology can be performed by measuring tyrosine kinase activity in vitro or in cells using standard assays known in the art. Biological activity can be measured using standard oncogene transformation assays using growth factor dependent hematopoietic cell lines or primary mouse bone marrow cells. Resistance to STI-571 can be measured using kinase assays and transformation assays.

Example 6

Use of Information Regarding BCR-ABL Domains and Crystallographic Analysis to Characterize BCR-ABL Mutations As the certain domains within BCR-ABL have been characterized and the crystal structure of this protein has been elucidated, this information can be used in conjunction with the disclosure provided herein to characterize MARS such those shown in Table I and to illustrate their role in resistance to inhibition of tyrosine kinase activity by STI-571. For example, from the initial inspection of these mutations in the context of the ABL crystal structure, one can categorize the mutants, for example in the following groups:

1. Helix C mutations (e.g. amino acid residue positions 304, 278):
Helix C is a key regulatory helix in the kinase V304D, V304A. These are located at the interface with helix C;
M278K, M278L: Surface exposed methionine is disordered (borders helix C). The functional significance of mutations found within this region or proximal to this region (in a manner that can perturb the normal function of this region), are supported by references which characterize this aspect of BCR-ABL.

2. P loop mutations (e.g. amino acid residue positions 253, 252, 250): The P loop is the phosphate binding loop whose conformation is thought to be induced by STI-571. These mutations could prevent the required conformation of the loop to accommodate STI-571. Interestingly, we have found no mutations in the Gly motifs in the P loop (249, 251 and 254). These are highly conserved across other kinases (so called Gly-X-Gly-X-X-Gly motif) and presumably are essential for kinase function. We do have examples of mutations in each of the X positions in the P loop. The functional significance of mutations found within this region or proximal to this region (in a manner that can perturb the normal function of this region), are supported by references which characterize this aspect of BCR-ABL. Y253F: Directly stacks up against STI-571. —OH makes a tight H-bond with CL (or H2O). Others: Q252H, Q252L, Q252R, G250E, E255K.

3. Residues which directly interact with STI-571 (e.g. amino acid residue positions 315, 351, 355, 317, 290): The functional significance of these residues or proximal to these residues (in a manner that can perturb the normal function of this region), are supported by references which characterize this aspect of BCR-ABL.

M351T: van der Waal interactions with His 361 which in turn interacts directly with STI-571 piperazine group. Thr mutation could disrupt the packing here and weaken interaction with STI-571. Interestingly, this mutation may not affect compound 15 binding (the one originally crystallized with Abl) since it has no piperazine group.

E355G: at the end of the helix that precedes the catalytic loop, which interacts with the piperazine group of STI-571. Mutating to a Gly could make this region more flexible and weaken STI binding. Again Compound 15 should be less affected by this mutation.

F317L: directly stacks against STI-571. Leu mutation could weaken STI-571 binding.

M290T, M290V: makes direct van der Waal interactions with STI-571. Mutation to either T or V would weaken STI-571 binding.

4) Activation loop mutations (e.g. amino acid residue positions 396). The functional significance of mutations found within this region or proximal to this region (in a manner that can perturb the normal function of this region), are supported by references which characterize this aspect of BCR-ABL.

H396K, H396R: disordered part of the activation loop.

Example 7

BCR-ABL Point Mutants Isolated from Patients with STI571-Resistant Chronic Myeloid Leukemia Remain Sensitive to Inhibitors of the BCR-ABL Chaperone Heat Shock Protein 90

Clinical resistance to STI571 (Gleevec/imatinib mesylate) is commonly observed in patients with advanced Philadelphia chromosome-positive (Ph+) leukemias. Acquired resistance is typically associated with reactivation of BCR-ABL due to kinase domain mutations or gene amplification, indicating that BCR-ABL remains a viable target for inhibition in these patients. Strategies for overcoming resistance can be envisioned through exploitation of other molecular features of the BCR-ABL protein, such as its dependence on the molecular chaperone heat shock protein 90 (Hsp90). To determine whether inhibition of Hsp90 could induce degradation of STI571-resistant, mutant BCR-ABL proteins, hematopoietic cells expressing two mutant BCR-ABL proteins found in STI571-resistant patients (T315I and E255K) were examined for sensitivity to geldanamycin and 17-AAG. Both compounds induced the degradation of wild-type and mutant BCR-ABL and inhibited cell growth, with a trend indicating more potent activity against mutant BCR-ABL proteins. These data support clinical investigations of 17-AAG in STI571-resistant Ph-positive leukemias.

Strategies for overcoming resistance associated with kinase domain mutations will likely require targeting other molecular features of the BCR-ABL protein. Heat shock protein 90 (Hsp90) is a molecular chaperone which affects the stability and function of multiple oncogenic proteins including BCR-ABL (An W G et al., Cell Growth Differ. 2000; 11:355-360; Shiotsu et al., Blood. 2000; 96:2284-2291). Geldanamycin (GA) is a benzoquinone ansamycin which specifically inhibits Hsp90 by competitively binding to an ATP-binding pocket in the amino-terminus of Hsp90 (Prodromou et al., Cell. 1997; 90:65-75; Stebbins et al., Cell. 1997; 89:239-250; Grenert et al., 1997; 272:23843-23850). Disruption of Hsp90 function by geldanamycin or its less toxic analogue, 17-allylaminogeldanamycin (17-AAG), in BCR-ABL-expressing leukemia cells has been shown to induce BCR-ABL protein degradation and suppress cell proliferation (An W G et al., Cell Growth Differ. 2000; 11:355-360; Blagosklonny M V, et al., Leukemia. 2001; 15:1537-1543; Nimmanapalli R, et al., Cancer Res. 2001; 61:1799-1804). 17-AAG is currently in phase I clinical trials.

To determine whether inhibition of Hsp90 could induce degradation of STI571-resistant, mutant BCR-ABL proteins, hematopoietic cells expressing two mutant BCR-ABL proteins found in STI571-resistant patients (T315I and E255K) were derived and tested for sensitivity to geldanamycin and 17-AAG. We found that both compounds induced the degradation of wild-type and mutant BCR-ABL proteins as well as inhibited cell growth. The data also suggest a trend indicating a greater potency against mutant BCR-ABL proteins. These results provide a rationale for the use of 17-AAG in the clinical setting of STI1571-resistant Ph-positive leukemia.

Chemicals. Stock solutions of GA (Sigma), 17-AAG (NSC 330507, National Cancer Institute), and STI571 (Novartis) were prepared as 10 mM dimethylsulfoxide solutions and stored at −20° C.

Plasmids and cell lines. Full-length P210 T315I and P210 E255K BCR-ABL in pBluescript (Stratagene) were generated using site-directed mutagenesis and confirmed by sequencing as described previously (Gorre et al., Science. 2001; 293:876-880). Wild-type and mutant P210 BCR-ABL were subsequently subcloned into the EcoRI site of pMSCVpuro (Clontech) for retrovirus generation. Ecotropic retroviruses were generated by cotransfection of pMSCVpuro DNA and Ecopac retroviral packaging vector (kindly provided by R. Van Etten) into 293T cells using the $CaCl_2$ method (Muller A J, et al., Mol. Cell. Biol. 1991; 11:1785-1792). The murine hematopoietic cell line Ba/F3 was maintained in RPMI1640 supplemented with 10% fetal bovine serum, L-glutamine, and 1 ng/ml of recombinant murine IL-3 (R&D). Ba/F3 populations with stable BCR-ABL expression were derived by retroviral infection of Ba/F3 cells in the presence of IL-3, and subsequent selection by puromycin. IL-3-independent BCR-ABL-expressing cells were derived by culturing in IL-3-free media at low densities in 96-well tissue culture plates. Multiple IL-3-independent populations were assayed for comparable BCR-ABL protein expression by western blot.

In vitro drug exposure assays. Cells were cultured in 24-well plates at $2 \times 10^5$ cells/ml in growth media (plus IL-3 for parental cells) with GA, 17-AAG, or STI571 for 24 or 48 hours. Subsequent analyses of protein by western blot or cell viability by trypan blue dye exclusion were done as previously described (Gorre et al., Science. 2001; 293:876-880; Goga A, et al., Cell. 1995; 82:981-988).

Results

Figure 7A:
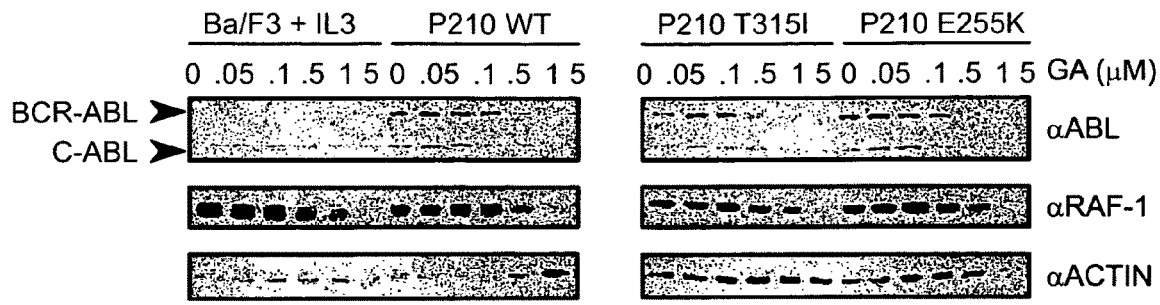
FIG. 7. Geldanamycin and 17-AAG induce degradation of wild-type and STI571-resistant, mutant BCR-ABL proteins and inhibit BCR-ABL signaling. (A) Ba/F3 cells expressing wild-type, T315I, or E255K BCR-ABL were incubated in the presence of increasing concentrations of geldanamycin (GA) for 24 hours. Immunoblotting of cell lysates was performed with anti-ABL (Ab3, Oncogene) (upper panels), anti-RAF-1 (Santa Cruz) (middle panels), and anti-actin (ac-15, Sigma) as a control for protein loading (lower panels). (B) Ba/F3 cells expressing wild-type, T315I, or E255K BCR-ABL were incubated in the presence of increasing concentrations of 17-AAG for 24 hours. Immunoblotting of these lysates was performed with anti-ABL (upper panels) and anti-actin as a control for protein loading (lower panels). (C) Immunoblotting of the same lysates from (B) was performed with anti-CRKL (Santa Cruz). CRKL, when tyrosine-phosphorylated, migrates more slowly on SDS-PAGE resulting in an upper band representing phosphorylated CRKL (P-CRKL) and a lower band representing non-phosphorylated CRKL. (D) Densitometric analysis of CRKL immunoblot shown in (C) using ImageQuant software (Molecular Dynamics). Quantified CRKL phosphorylation is expressed as percentage of phosphorylated CRKL over total CRKL protein (% P-CRKL). (E) Densitometric analysis of CRKL immunoblotting using lysates from the same Ba/F3 cell lines incubated in the presence of increasing concentrations of STI571 for 24 hours.

Previous studies have shown that the Hsp90 inhibitors GA and its derivative, 17-AAG, disrupt Hsp90 function and induce BCR-ABL protein degradation (An W G et al., Cell Growth Differ. 2000; 11:355-360; Blagosklonny M V, et al., Leukemia. 2001; 15:1537-1543; Nimmanapalli R, et al., Cancer Res. 2001; 61:1799-1804). To determine whether GA can similarly cause the degradation of BCR-ABL proteins carrying STI571-resistant point mutations, populations of interleukin-3 (IL-3) dependent Ba/F3 murine hematopoietic cells were engineered to express either wild-type, T315I, or E255K P210 BCR-ABL and exposed to varying concentrations of inhibitor. Consistent with previous reports, both mutant BCR-ABL alleles rendered the cells independent of IL-3, and cells expressing either mutant contained high levels of phosphotyrosine on BCR-ABL and other substrate proteins (Gorre et al., Science. 2001; 293:876-880; von Bubnoff et al., Lancet. 2002; 359:487-491). Western blot analyses using ABL-specific antibodies demonstrated that GA caused BCR-ABL protein levels to decrease significantly in cells expressing wild-type BCR-ABL after treatment for 24 hours at a dose of 1.0 µM, as expected (An W G et al., Cell Growth Differ. 2000; 11:355-360; Blagosklonny M V, et al., Leukemia. 2001; 15:1537-1543; Nimmanapalli R, et al., Cancer Res. 2001; 61:1799-1804). BCR-ABL protein was also degraded in cells expressing either T315I or E255K BCR-ABL, but this degradation occurred at a lower GA concentration (0.5 µM) (FIG. 7A). This apparently enhanced degradation of the two mutant BCR-ABL proteins was specific because degradation of another Hsp90 client protein, RAF-1, was comparable in all cells tested. These data suggest that GA may have greater potency against mutant BCR-ABL proteins compared to wild-type.

Figure 7B:
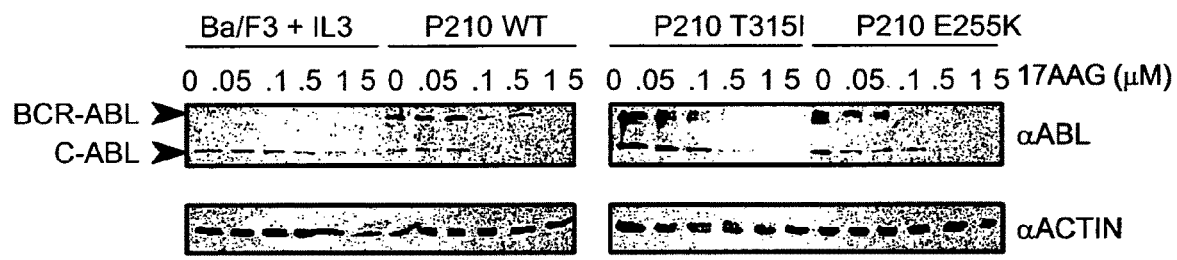
Figure 7C:
Figure 7D:
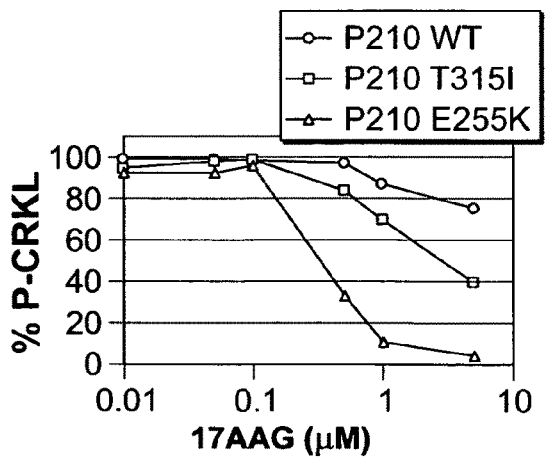
Figure 7E:
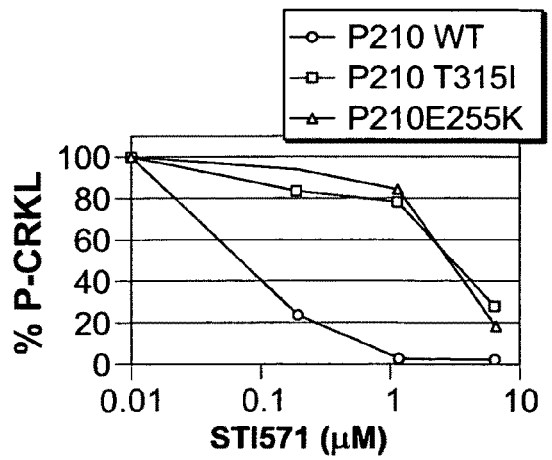

We next tested 17-AAG—a GA derivative currently in phase I clinical trials—for its ability to induce BCR-ABL protein degradation in the same Ba/F3 cell lines. Western blot analyses of lysates from cells cultured in 17-AAG showed a similar trend to that seen with GA. Wild-type BCR-ABL protein levels fell gradually after 24 hour exposure to 0.5-1.0 µM 17-AAG. Although BCR-ABL protein levels in both the T315I and E255K BCR-ABL-expressing cells began to decline at a similar concentration of 17-AAG as wild-type BCR-ABL (0.5 µM), the magnitude of decrease was more dramatic in cells expressing the BCR-ABL mutants. Virtually no BCR-ABL protein was detectable at 1.0 µM of 17-AAG for both mutants (FIG. 7B). This trend was confirmed when we assessed the effect of 17-AAG on downstream BCR-ABL signaling by measuring the phosphorylation status of CRKL, a direct BCR-ABL substrate with functional relevance in CML (Nichols et al., Blood. 1994; 84:2912-2918; Oda et al., J. Biol. Chem. 1994; 269:22925-22928; Senechal et al., J. Biol. Chem. 1996; 271:23255-23261; ten Hoeve J et al., Blood. 1994; 84:1731-1736). Western blot analysis using CRKL-specific antisera on lysates from cells incubated in the presence of increasing concentrations of STI571 confirmed that the BCR-ABL mutants conferred resistance to STI571 (FIG. 7E). CRKL western blot analysis on lysates from 17-AAG-treated cells revealed that lower doses of 17-AAG were needed to inhibit BCR-ABL activity in cells expressing the BCR-ABL mutants when compared to wild-type BCR-ABL (FIG. 7C,D). Significant changes in CRKL phosphorylation were not observed in wild-type BCR-ABL-expressing cells until a 17-AAG concentration of 5.0 µM was reached, whereas CRKL phosphorylation in T315I and E255K BCR-ABL-expressing cells was significantly inhibited at 0.5 µM of drug (FIG. 7C,D). While 17-AAG may affect another kinase which plays a role in CRKL phosphorylation in these cells, the fact that 17-AAG also reduced the level of BCR-ABL protein, together with previously published data showing that constitutively elevated CRKL phosphorylation is relatively specific for CML (Nichols et al., Blood. 1994; 84:2912-2918), provides strong evidence that BCR-ABL is the target.

Previous studies have also shown that GA and 17-AAG inhibit growth and induce apoptosis of BCR-ABL-positive leukemic cell lines (Blagosklonny M V, et al., Leukemia. 2001; 15:1537-1543; Nimmanapalli R, et al., Cancer Res. 2001; 61:1799-1804). To determine whether GA could inhibit growth in cells expressing STI571-resistant BCR-ABL mutants, Ba/F3 cells transformed by wild-type, T315I, and E255K BCR-ABL were cultured in a range of GA concentrations. Trypan blue dye exclusion assessments of viability and corresponding $IC_{50}$ calculations indicated that the growth of all three BCR-ABL-positive cell lines was inhibited by GA at lower doses when compared to BCR-ABL-negative parental cells (Table III). The enhanced sensitivity of the STI-571 resistant BCR-ABL mutants compared to wild-type BCR-ABL observed in the biochemical analyses was also recapitulated in the growth inhibition assays. Similar results were observed with 17-AAG-treated cells. All BCR-ABL-expressing cells were more sensitive to 17-AAG than Ba/F3 parental cells, and the STI571-resistant BCR-ABL-expressing cells again displaying a heightened sensitivity to inhibition compared to wild-type BCR-ABL-expressing cells (Table III).

In summary, targeted inhibition of Hsp90 with either GA or 17-AAG induced the degradation of wild-type BCR-ABL and two STI571-resistant BCR-ABL mutants T315I and E255K. Both compounds also inhibited the growth of hematopoietic cells transformed by wild-type and mutant BCR-ABL. The results also suggest that the STI571-resistant mutants are more sensitive to Hsp90 inhibition than wild-type BCR-ABL. One potential explanation could be that these two mutant proteins are less stable than wild-type BCR-ABL, and therefore more dependent on molecular chaperones. A better understanding of the variables that determine the relative dependence of client proteins on Hsp90 function is required to fully evaluate this question. Nevertheless, these data provide support for clinical investigations of 17-AAG in STI571-resistant Ph-positive leukemia.

Example 8

Identification of a Novel Pyridopyrimidine Inhibitor of ABL Kinase that is a Picomolar Inhibitor of BCR-ABL Driven K562 Cells and is Effective Against STI571-Resistant BCR-ABL Mutants Inhibition of the constitutively active Bcr-abl tyrosine kinase (TK) by STI571 has proven to be a highly effective treatment for chronic myelogenous leukemia (CML). However STI571 is only transiently effective in blast crisis and drug resistance emerges by amplification of or development of mutational changes in Bcr-abl. As described in this example, we have screened a family of TK inhibitors of the pyrido[2,3-d]pyrimidine class, unrelated to STI571, and describe here a compound with substantial activity against STI-resistant mutant Bcr-abl proteins. This compound, PD166326, is a dual specificity TK inhibitor and inhibits src and abl in vitro with $IC_{50}$s of 6 and 8 nM respectively. PD166326 inhibits the growth of K562 cells with $IC_{50}$ of 300 picomolar, leading to apoptotic G1 arrest, while non-Bcr-abl cell types require more than 1000 times higher concentrations. We tested the effects of PD166326 on two of the clinically observed Bcr-abl mutants. The T315I mutation within the ATP-binding pocket reduces the affinity of STI571 for this pocket while the structural basis for resistance of the E255K mutation is currently unknown. PD166326 potently inhibits the E255K mutant Bcr-abl protein and the growth of Bcr-ablE255K driven cells. The T315I mutant Bcr-abl protein is resistant to PD166326, however the growth of Bcr-ablT315I driven cells is partially sensitive to this compound, likely through the inhibition of Bcr-abl effector pathways. These findings show that tyrosine kinase drug resistance is a structure-specific phenomenon and can be overcome by TK inhibitors of other structural classes, suggesting new approaches for future anti-cancer drug development. PD166326 is a prototype of a new generation of anti-Bcr-abl compounds with picomolar potency and substantial activity against STI571-resistant mutants.

Cell Culture and Growth Assays

Cell were cultured in RPMI medium supplemented with 100 U/ml penicillin, 100 µg/ml streptomycin, 4 mM glutamine, 10% heat inactivated fetal bovine serum and incubated at 37 C in 5% $CO_2$. For growth assays, cells were seeded in 12-well clusters at 10-20,000 cells per well. Cells were placed in media containing various concentrations of the drugs with vehicle (DMSO) never contributing more than 0.1%. After 4-7 days, cells were counted using a coulter counter. All experiments were performed in duplicate and results averaged. PD166326 was stored in a 10 mg/ml DMSO solution and stored at −70C. The derivation and chemical structure of PD166326 has been previously published (see e.g. Kraker et al., Biochemical Pharmacology 60, 885-898. 2000).

Cell Cycle Assays

Cells were treated with indicated concentrations of PD166326 or vehicle (DMSO) for the indicated times. For synchronization, cells were incubated in media containing 5 ug/ml aphidicolin for 24 hours, washed twice in PBS, and replaced in growth media. At the time of harvest, cells were washed once in PBS and cell nuclei prepared by the method of Nusse (see e.g. Nusse et al., Cytometry. 1990; 11:813-821) and cell cycle distribution determined by flow cytometric analysis of DNA content using red fluorescence of 488 nm excited ethidium bromide stained nuclei.

Protein Extraction and Western Blotting

Cells were washed in PBS once and lysed in modified RIPA buffer (10 mM Na phosphate pH 7.2, 150 mM NaCl, 0.1% sodium dodecyl sulfate, 1% NP-40, 1% Na deoxycholate, 1 mM Na Vanadate, and protease inhibitors). 50 ug of total cellular protein was separated by SDS-PAGE, transferred to membrane, and immunoblotted using antibodies to phosphotyrosine (SantaCruz), c-abl (8E9), and phospho-Hck (SantaCruz), MAP kinase (SantaCruz) and phospho-MAP kinase (Promega).

In Vitro Kinase Assay

C-abl kinase assays were performed using purified recombinant c-abl and peptide substrate (New England Biolabs). Kinase assays were performed in 50 mM Tris-Cl pH 7.5, 10 mM $MgCl_2$, 1 mM ethylene glycol bis-aminoethyl ether tetraacetic acid (EGTA), 2 mM dithiothreitol (DTI), 0.2% triton-X, 100 uM ATP, 40 uM peptide substrate, in 100 ul reaction volumes containing 50 units c-abl enzyme and 10 uCi [$^{32}$P] γ-ATP. Reactions were allowed to proceed for 10 minutes at 30 C and stopped by addition of EDTA and boiling. Reaction products were spotted on phosphocellulose paper, washed several times with phosphoric acid, then acetone, and counted in scintillation fluid. Pilot experiments were initially performed to establish that these reaction conditions were in linear range.

Bcr-Abl was immune precipitated from cell lysates of K562 cells maintained in log-phase culture conditions. Complexes were collected on protein A-sepharose and washed three times in lysis buffer and twice in abl kinase buffer (50 mM tris pH 8.0, 10 mM $MgCl_2$, 1 mM DTT, and 2 mM p-nitrophenylphosphate, and 2 mM ATP; New England Biolabs Buffer and protocol). Kinase assays were performed with 10 mM [γ-32P] ATP/sample for 15-60 minutes at 30 C in the presence or absence of indicated concentrations of drug. The immune complexes were pre-incubated with the drug for 10 minutes at 4 C prior to addition of labelled ATP and initiation of the reaction at 30 C. The reaction was stopped by the addition of SDS-PAGE sample buffer and heated at 100 C for 10 minutes. Proteins were separated on 7.5% SDS-polyacrylamide gels and gels were dried under vacuum and phosphorylation was visualized by autoradiography on x-ray film.

Results

In screening a compound library for inhibitors of c-src tyrosine kinase activity, a number of pyrido[2,3-d]pyrimidines were previously described that are ATP-competitive inhibitors of c-src with $IC_{50}$ values <20 nM and varying degrees of selectivity for c-src (see e.g. Kraker et al., Biochemical Pharmacology 60, 885-898. 2000). We screened this group of compounds for activity against c-abl using purified recombinant c-abl and peptide substrate in in vitro kinase assays. The most potent compound was PD166326 with an $IC_{50}$ of 8 nM (against c-abl) and 6 nM (against src). The src family kinase Lck is inhibited with $IC_{50}$<5 nM. This compound also has activity against basic-FGF, PDGF, and EGF receptor tyrosine kinases in vitro with $IC_{50}$s of 62, 139, and 80 nM respectively. PD166326 shows no significant activity against JNK kinases, cyclic AMP-dependent protein kinase (PKA), PKB-β, PKC-α, rho-dependent protein kinase, casein kinase-2, and phosphorylase kinase. In comparison with PD166326, STI571 is a weaker inhibitor of Abl in vitro with an $IC_{50}$=50 nM. PD166326 also inhibits Bcr-abl kinase in vitro with $IC_{50}$=1 nM.

PD166326 also inhibits Bcr-abl activity in cells as determined by Western blot analysis of Bcr-abl autophosphorylation in K562 cells. In these cells Bcr-abl autophosphorylation is inhibited with $IC_{50}$ of 1 nM compared with 100 nM for STI571. Bcr-abl autophosphorylation correlates with Bcr-abl signaling activity as shown by the parallel decline of MAP kinase activity with inhibition of Bcr-abl in these assays.

The biologic activity and potency of PD166326 was initially evaluated in cell growth assays using K562 cells. This compound inhibits K562 cell growth with $IC_{50}$=0.3 nM. Other Bcr-abl driven cell lines are also extremely sensitive to PD166326 with $IC_{50}$s of 0.8 and 6 nM (see M07-p210$^{bcr-abl}$ and BaF3-p210$^{bcr-abl}$). The potent biologic activity of PD166326 is highly specific for Bcr-abl-driven cells as additional hematopoetic and epithelial cell lines are only inhibited at 2 to 3 logs higher concentrations and $IC_{50}$s in the 0.8-2 uM range.

Further analysis reveals that PD166326 inhibits cell proliferation specifically in the G1 phase of the cell cycle. At concentrations that fully inhibit the growth of Bcr-abl positive cells but not other cell types, PD166326 leads to accumulation of cells in the G1 phase accompanied by a significant increase in the number of apoptotic cells. Additional phases of the cell cycle are not affected by this compound as shown by experiments with synchronized cells. K562 cells were synchronized at the G1/S boundary with aphidicolin and released into PD166326 or vehicle and cell cycle progression studied over the following 24 hours. These data show that PD166326 treatment does not interfere with progression through the S, G2 or mitotic phases of the cell cycle, but PD166326 treated cells are unable to exit the G1 phase. Similar experiments with nocodazole-synchronized cells also confirm that PD166326 blocks G1 progression. The inhibition of G1 progression and induction of apoptosis in K562 cells are similar to the effects previously reported for STI571 (see e.g. Dan et al., Cell Death & Differentiation. 1998; 5:710-715). These data show that PD166326 is a potent inhibitor of Bcr-abl kinase activity and inhibits Bcr-abl driven cell growth through inhibition of G1 progression leading to apoptotic cell death.

Resistance to STI571 treatment is associated with mutations in the Bcr-abl oncoprotein that render it refractory to STI571 inhibition (see e.g. Gorre et al., Science. 2001; 293: 876-880). Because PD166326 inhibits both Src and Abl whereas STI571 only inhibits Abl, it may bind Bcr-abl differently than STI571. This difference raises the possibility that it may be effective against some mutant Bcr-abl proteins. We compared the activities of PD166326 and STI571 against two such mutant Bcr-abl proteins derived from patients who have relapsed on STI571 therapy. The T315I mutation is frequently seen in relapsed patients and eliminates a critical Threonine residue within the ATP binding pocket of Abl and greatly reduces the binding affinity of STI571. The E255K mutation also lies within a region of Bcr-abl commonly mutated in relapsed patients, however the structural basis for STI571 resistance conferred by mutations in this region is not currently understood. BaF3 mouse hematopoietic cell lines were stably transfected with either the wild-type $p210^{bcr-abl}$ cDNA or the T315I or E255K mutant versions as previously described (see e.g. Gorre et al., Science. 2001; 293:876-880). Expression of Bcr-abl renders BaF3 cells IL-3 independent while control cells transfected with vector alone require IL-3 for growth. Although STI571 inhibits the wild-type $p210^{bcr-abl}$ cells with $IC_{50}$=500 nM, the T315I and E255K mutant $p210^{bcr-abl}$ cells are highly resistant. However resistance to STI571 does not appear to confer cross-resistance to PD166326. PD166326 inhibits the autophosphorylation of $p210^{Bcr-ablE255K}$ in vivo as effectively as the autophosphorylation of the wild type $p210^{Bcr-abl}$, while this mutant is highly resistant to inhibition by STI571. However, the $p210^{Bcr-ablT315I}$ mutant is resistant to PD166326 as it is to STI571. This is not surprising, considering the critical role of $Thr^{315}$ within the ATP binding pocket.

To determine whether cell growth sensitivity to PD166326 correlates with inhibition of the mutant Bcr-abl oncoproteins, we also determined the sensitivity of the BaF3 cells driven by the wild type and mutant Bcr-abl proteins. $BaF3^{p210Bcr-abl}$ cells are very sensitive to PD166326 ($IC_{50}$=6 nM) and the E255K mutant $p210^{bcr-abl}$ cells remain relatively sensitive to this compound ($IC_{50}$=15 nM). The effective inhibition of $p210^{E255Kbcr-abl}$ activity at dose ranges that inhibit the growth of these cells is further evidence that STI571-resistant leukemic cells are driven by persistent activity of the mutated Bcr-abl oncoprotein. In comparison, the T315I mutant cells are partially resistant to PD166326, although not fully resistant. PD166326 inhibits $BaF3^{p210T315I}$ cells with $IC_{50}$ of 150 nM. Although this is 25 fold weaker than the inhibition of the wild-type $BaF3^{p210}$ cells, it may still be of therapeutic value since it is 8-fold more potent than the inhibition of the BaF3-vector controls and non-Bcr-abl driven cells. Although PD166326 inhibits the growth of $BaF3p210^{Bcr-ablT315I}$ cells with $IC_{50}$ of 150 nM, it fails to inhibit the autophosphorylation of the T351I Bcr-abl mutant at doses up to 1 uM, suggesting that its anti-proliferative effects are mediated in part through mechanisms other than the inhibition of Bcr-abl.

PD166326 is also active against src kinases and its anti-leukemic effects may be in part related to its inhibition of the src kinases Hck and Lyn which function downstream of Bcr-abl. The src kinases Hck and Lyn are activated by Bcr-abl and may mediate some of the transforming functions of Bcr-abl. Phosphorylation of $tyr^{416}$ in the catalytic domain is required for activation of src kinases, although the mechanism by which Bcr-abl activates Hck and Lyn is not understood. Inhibition of Bcr-abl by STI571 results in a parallel inhibition of Hck activation in K562 cells. In these cells PD166326 also inhibits Bcr-abl and Hck activation although at 100 fold lower doses than seen with STI571. Hck is also activated by mutant forms of Bcr-abl and in the mutant $BaF3p210^{Bcr-ablE255K}$ cells, PD166326 inhibits Hck activation and this correlates with the observed inhibition of Bcr-abl$^{E255K}$ autophosphorylation and inhibition of cell growth. In contrast, the activation of Hck by the Bcr-abl$^{T315I}$ mutant is not inhibited by PD166326 and this correlates with the observed resistance of Bcr-abl$^{T315I}$ activity to PD166326. However despite failure to inhibit Bcr-abl activity and the consequent activation of Hck, PD166326 inhibits the growth of $BaF3p210^{Bcr-ablT315I}$ cells with $IC_{50}$ of 150 nM, likely through additional mechanisms.

Although STI571 has revolutionized the treatment of CML, the problem of TK drug resistance is now emerging as a clinical reality. Resistance to STI571 appears to have a structural basis and newer TK inhibitors may also be susceptible to similar mechanisms of resistance. However TK inhibitors of a different structural class may have more favorable binding characteristics. Dorsey et al initially reported that a src-selective TK inhibitor of the pyrido[2,3-d]pyrimidine class has substantial activity against Bcr-abl kinase (see e.g. Dorsey et al., Cancer Research. 2000; 60:3127-3131). We have extended this finding by screening a family of src-selective pyrido[2,3-d]pyrimidines and identified a compound with the most potent activity against abl kinase. Here we report the characterization of this compound, PD166326, a novel dual specificity TK inhibitor that is more than 100 fold more potent than STI571 in vivo and inhibits K562 cells with $IC_{50}$ of 300 picomolar. It is unlikely that the potent growth inhibitory activities of PD166326 are related to non-specific activities since the potency of this compound appears to be specific for cell types driven by Bcr-abl kinase. While Bcr-abl-driven cells are inhibited with $IC_{50}$s in the 0.3-6 nM range, other cell types including the hematopoietic cells BaF3 and 32D as well as epithelial cancer cells including MCF-7 cells and MDA-MB-468 cells, which are driven by EGFR overactivity, are inhibited with $IC_{50}$s in the 0.8-2 uM range (table 2). The micromolar activity of PD166326 against the growth of non-Bcr-abl driven cells is most likely mediated through inhibition of additional cellular targets since unlike Bcr-abl positive cells, the growth of Bcr-abl negative cells is inhibited during the S phase of the cell cycle. The picomolar potency and cellular selectivity of PD166326 are significantly superior to STI571 in vitro.

Since Bcr-abl signaling is known to involve the src family kinases Hck and Lyn, and since PD166326 is also a potent inhibitor of src family kinases, it is plausible that the biologic potency of this compound is related to dual inhibition of these two functionally related tyrosine kinases. Hck associates with and phosphorylates Bcr-abl on Tyr 177 leading to recruitment of Grb2/Sos and activation of the Ras pathway (see e.g. Warmuth et al., Journal of Biological Chemistry. 1997; 272: 33260-33270). Kinase-defective Hck mutants suppress Bcr-abl induced transformation suggesting that Hck-mediated signaling is essential for the transforming activity of Bcr-abl (see e.g. Lionberger et al., Journal of Biological Chemistry. 2000; 275:18581-18585). The role of Lyn in Bcr-abl signaling is less well studied. However Lyn activity is also elevated in acute myeloid leukemia cell lines and in these cells inhibition of Lyn expression using anti-sense molecules leads to decreased proliferative activity and inhibition of Lyn kinase activity using src family selective pharmacologic inhibitors leads to potent inhibition of cell growth and colony formation (see e.g. Roginskaya et al., Leukemia. 1999; 13:855-861). It is also possible that the potency of PD166326 is mediated through the inhibition of other, yet undiscovered cellular proteins, and our data does not exclude this possibility. However the role of currently unknown cellular targets in mediating the growth inhibitory effects of this compound in Bcr-abl driven cells is difficult to know until such candidate targets are identified and studied.

Since relapse on STI571 is associated with mutations in Bcr-abl that alter the binding of STI571, understanding the nature of the STI571 interaction with Abl is of fundamental importance in order to overcome drug resistance. The crystal structure of a variant STI571 in complex with the catalytic domain of Abl was recently solved by Schindler et al (see e.g. Schindler et al., Science. 2000; 289:1938-1942). STI binds within the ATP binding pocket of Abl in its inactive conformation. This interaction is critically affected by the conformation of the Abl activation loop. When phosphorylated, this activation loop favors an open and activating conformation which, by virtue of its amino-terminal anchor, interferes with STI571 binding to the ATP-binding pocket. Consistent with this model, the binding of STI571 is selective for the inactive conformation of Abl, and this compound is unable to inhibit the catalytic activity of active phosphorylated Abl (see e.g. Schindler et al., Science. 2000; 289:1938-1942). The broader activity of PD166326, including activity against src kinases suggests that unlike STI571, it may not bind selectively to the inactive conformation of Abl, since in its active conformation, Abl bears considerable structural homology to the src kinases (see e.g. Schindler et al., Science. 2000; 289:1938-1942). While selectivity for the inactive conformation is postulated to confer a high degree of molecular specificity to STI571, this may be at the price of potency. PD166326 may be binding to both inactive and active conformations of Abl leading to the more effective inhibition of overall enzyme activity that we see in vitro. In addition, phosphorylation of the activation loop of Abl is catalyzed by the src family kinase Hck in Bcr-abl transformed cells. Since PD166326 also inhibits Hck, this may prevent phosphorylation of the activation loop, destabilizing the Abl active conformation. This allosteric mechanism in addition to the direct binding of PD166326 to the ATP-binding pocket could provide dual mechanisms for its inhibition of Abl activation and provide the basis for its increased potency. Validation of these hypotheses awaits crystallographic studies of PD166326 bound to Abl.

PD166326 is non-cross-resistant with STI571 and has substantial activity against the T315I and E255K STI571-resistant Bcr-abl mutants. This finding has important implications for the future design and use of TK inhibitors of all kinds, since it is the first report showing that TK-inhibitor resistance can be overcome by another TK-inhibitor of a different structural class. It is difficult to speculate on whether the development of resistance to PD166326 will be just as likely as with STI571, but since these compounds are structurally unrelated, resistance to PD166326 will likely involve a different structural basis than resistance to STI571. This distinction creates the opportunity for strategies to prevent or overcome resistance such as sequential or combination therapies. However understanding drug sensitivity and resistance is of fundamental importance in this regard.

While additional studies will elucidate the exact structural and cellular basis underlying STI571 resistance and PD166326 sensitivity, existing data explains our findings. A number of amino acid residues mediate the binding of STI571 within the ATP-binding pocket, and among these, $Thr^{315}$ is critical for hydrogen bond formation with the drug (see e.g. Schindler et al., Science. 2000; 289:1938-1942). The T315I mutation, seen in STI571-resistant CML, precludes hydrogen bonding with STI571 and results in a steric clash due to the extra hydrocarbon group in Ile (see e.g. Gorre et al., Science. 2001; 293:876-880). Likewise PD166326 does not inhibit the activity of Bcr-abl$^{T315I}$ in vivo suggesting that $Thr^{315}$ is also important for its binding within the ATP pocket of abl. However PD166326 has some activity against BaF3p210$^{T315I}$ cells and inhibits their growth with $IC_{50}$ of 150 nM. This activity is related to Bcr-abl driven growth since growth inhibition of non-Bcr-abl driven cell types requires 5-15 fold higher concentrations. Since PD166326 is a potent inhibitor of src kinases, and since the src kinases Hck and Lyn mediate some of the transforming activities of Bcr-abl, it is possible that PD166326 inhibits the growth of BaF3p210$^{T315I}$ cells through the inhibition of Hck and Lyn. However, seemingly inconsistent with this hypothesis, we fail to see inhibition of Hck $Y^{416}$ phosphorylation in these cells at growth inhibitory concentrations. However this does not disprove the hypothesis due to limitations in assaying Hck activity in vivo. If PD166326 binds with and inhibits the active $Y^{416}$ phosphorylated conformation of Hck, then this catalytically inactive drug-Hck complex may remain stably in this phosphorylated conformation and phospho-$Y^{416}$ Hck antibodies will be unable to demonstrate the in vivo inhibition of Hck catalytic function. In vitro kinase assays do not help in this regard either, since during the process of cell lysis and immunoprecipitation, the Hck-PD166326 interaction is lost. Therefore, in BaF3 p210$^{T315I}$ cells, where Bcr-abl activity is resistant to PD166326, inhibition of Hck activity may be responsible for the observed growth inhibitory effects at $IC_{50}$=150 nM despite persistent phosphorylation of Hck at these doses. In addition, although $Y^{416}$ is a site of auto-phosphorylation in src kinases, it may also be a substrate for phosphorylation by other kinases. In fact in our experiments Hck $Y^{416}$ phosphorylation status parallels Bcr-abl activity which suggests that Hck $Y^{416}$ may also be a substrate for Bcr-abl. Although the activity of PD166326 against src kinases would suggest that it inhibits BaF3 p210$^{T315I}$ cells through a src family member, these experiments do not rule out the possibility that this cellular sensitivity is mediated through the inhibition of other, yet unknown, kinases.

The structural basis for the STI571 resistance of the E255K mutated Bcr-abl is less clear since the functional significance of this residue is currently unknown. Interestingly this mutation confers little resistance to PD166326. PD166326 shows no loss of activity against Bcr-abl$^{E255K}$ autophosphorylation in vivo and only 2.5 fold less activity against the growth of BaF3Bcr-abl$^{E255K}$ cells compared with wild type Bcr-abl controls. The cellular $IC_{50}$ of PD166326 against BaF3Bcr-abl$^{E255K}$ cells (15 nM) is much lower than its activity in non-Bcr-abl driven cell types (0.8-2 uM), and much greater than the activity of STI571 against this mutant. If the basis for Bcr-abl E255K resistance to STI571 is destabilization of the inactive conformation, and if PD166326 in fact binds to the active conformation, then this would explain why PD166326 is effective in inhibiting Bcr-abl$^{E255K}$. However validation of these hypotheses requires crystal structure data to better define the function of the Glu$^{255}$ residue and the binding of PD166326 to Bcr-abl.

TABLES

Tables 1A-1E identify typical MARS. The data are from analysis of patients, with an average of 10 clones sequenced per patient. These tables identify subgroups of mutations that are more likely to be significant because they occur in more than one patient or they are dominant (defined as being detected in at least 2 of 10 clones in the same patient). The observation that these mutants are showing up so commonly provides further evidence that these mutations will turn out to be clinically significant.

TABLE IA

Residues Mutated in Individuals Treated with STI-571

D233, T243, M244, K245, G249, G250, G251, Q252, Y253, E255, V256L Y257, F259, K262, D263, K264, S265, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, M359, N358, F359, I360, L364, E373, N374, K378, V379, A380, D381, F382, T389, T392, T394, A395, H396, A399, P402, T406.

TABLE IB

Typical Mutations at a Glance

D233H, T243S, M244V, G249D, G250E, G251S, Q252H, Y253F, Y253H, E255K, E255V, V256L, Y257F, Y257R, F259S, K262E, D263G, K264R, S265R, V268A, V270A, T272A, Y274C, Y274R, D276N, T277P, M278K, E282G, F283S, A288T, A288V, M290T, K291R, E292G, I293T, P296S, L298M, L298P, V299L, Q300G, G303E, V304A, V304D, C305S, C305Y, T306A, F311L, I314V, T315A, T315I, E316G, F317L, M318T, Y320C, Y320H, G321E, D325H, Y326C, L327P, R328K, E329V, Q333L, A337V, V339G, L342E, M343V, M343T, A344T, A344V, I347V, A350T, M351T, E352A, E352K, E355G, K357E, N358D, N358S, F359V, I360K, I360T, L364H, E373K, N374D, K378R, V379I, A380T, A380V, D381G, F382L, T389S, T392A, T394A, A395G, H396K, A399P, P402T, T406A.

TABLE IC

Mutations Occurring in More Than One Patient

Q252H, E255K, K264R, F283S, M290T, P296S, V304D, T315I, R328K, M343T, M343V, A344T, M351T, K357E, M359V, I360T.

TABLE ID

Dominant Mutations or Mutations with Frequencies Greater Than One Clone/Patient

G250E, Q252H, Y253F, Y253H, E255K, V270A, V304D, T315I, F317L, M343T, M351T, E355G, M359V, I360K, V379I, F382L, H396K.

TABLE IE

Mutations Occurring in More Than One Patient With a Dominant Clone or at Least Greater Than One Clone Occurrence

Q252H, E255K, V304D, T315I, F317L, R328K, F359V, M351T.

TABLE IF

Attached Mutations

Y257F, Y274R, D276N, E282G, M290T, I293T, P296S, L298M, L298P, V304D, T315I, F317L, G321E, Q333L, A337V, V339G, M343T, M351T, E352A, I360T, E373K, V379I, D381G, F382L, T392A.

TABLE II

GenBank accession number M14752

(SEQ ID NO: 1)
MLEICLKLVGCKSKKGLSSSSSCYLEEALQRPVASDFEPQGLSEAARWNS

KENLLAGPSENDPNLFVALYDFVASGDNTLSITKGEKLRVLGYNHNGEWC

EAQTKNGQGWVPSNYITPVNSLEKHSWYHGPVSRNAAEYLLSSGINGSFL

VRESESSPGQRSISLRYEGRVYHYRINTASDGKLYVSSESRFNTLAELVH

HHSTVADGLITTLHYPAPKRNKPTVYGVSPNYDKWEMERTDITMKHKLGG

GQYGEVYEGVWKKYSLTVAVKTLKEDTMEVEEFLKEAAVMKEIKHPNLVQ

LLGVCTREPPFYIITEFMTYGNLLDYLRECNRQEVNAVVLLYMATQISSA

MEYLEKKNFIHRDLAARNCLVGENHLVKVADFGLSRLMTGDTYTAHAGAK

FPIKWTAPESLAYNKFSIKSDVWAFGVLLWEIATYGMSPYPGIDLSQVYE

LLEKDYRMERPEGCPEKVYELMRACWQWNPSDRPSFAEIHQAFETMFQES

TABLE II-continued

GenBank accession number M14752

SISDEVEKELGKQGVRGAVSTLLQAPELPTKTRTSRRAAEHRDTTDVPEM

PHSKGQGESDPLDHEPAVSPLLPRKERGPPEGGLNEDERLLPKDKKTNLF

SALIKKKKKTAPTPPKRSSSFREMDGQPERRGAGEEEGRDISNGALAFTP

LDTADPAKSPKPSNGAGVPNGALRESGGSGFRSPHLWKKSSTLTSSRLAT

GEEEGGGSSSKRFLRSCSASCVPHGAKDTEWRSVTLPRDLQSTGRQFDSS

TFGGHKSEKPALPRKRAGENRSDQVTRGTVTPPPRLVKKNEEAADEVFKD

IMESSPGSSPPNLTPKPLRRQVTVAPASGLPHKEEAEKGSALGTPAAAEP

VTPTSKAGSGAPGGTSKGPAEESRVRRHKHSSESPGRDKGKLSRLKPAPP

PPPAASAGKAGGKPSQSPSQEAAGEAVLGAKTKATSLVDAVNSDAAKPSQ

PGEGLKKPVLPATPKPQSAKPSGTPISPAPVPSTLPSASSALAGDQPSST

AFIPLISTRVSLRKTRQPPERIASGAITKGVVLDSTEALCLAISRNSEQM

ASHSAVLEAGKNLYTFCVSYVDSIQQMRNKFAFREAINKLENNLRELQIC

PATAGSGPAATQDFSKLLSSVKEISDIVQR

TABLE III

Sensitivity of STI571-resistant BCR-ABL-transformed cells to geldanamycin and 17-AAG.

| CELL LINE | MEAN IC$_{50}$ ± S.D. (µM) | |
|---|---|---|
| | GA | 17-AAG |
| Ba/F3 + IL-3 | 27.3 ± 14.1 | 12.4 ± 0.3 |
| Ba/F3 P210 WT | 4.9 ± 1.6 | 5.2 ± 2.4 |
| Ba/F3 P210 T315I | 1.8 ± 2.1 (P = 0.03)* | 2.3 ± 0.4 (P = 0.04) |
| Ba/F3 P210 E255K | 2.6 ± 2.4 (P = 0.05) | 1.0 ± 0.2 (P = 0.01) |

Representative data from at least two independent experiments performed in duplicate; IC$_{50}$, concentration of inhibitor required to reduce the number of viable cells by 50%;
*Differences in the mean IC$_{50}$ values between WT and mutant P210 Ba/F3 cells were analyzed with the unpaired Student's t-test; two-tailed P values are shown.

TABLE IV

Detailed summary of Bcr-Abl kinase domain mutations by disease category.

| Patient No. | Duration of Treatment with imatinib at time of analysis | Mutation(s) | # of independent clones containing mutation |
|---|---|---|---|
| 1 (MBC) | 4.5 months | G250E | (7/10) |
| | | H396R | (2/10) |
| 2 (MBC) | 13 months | T315I | (10/10) |
| 3 (MBC) | 8 months | none | N/A |
| 4 (MBC) | 3.5 months | M351T | (5/10) |
| 5 (MBC) | 1 month | Q252H | (5/10) |
| 6 (MBC) | 13 months | M351T | (8/10) |
| 7 (MBC) | 13 months | M351T | (6/10) |
| 8 (MBC) | 1 month | V304D | (2/10) |
| 9 (MBC) | 5 months | E255K | (4/10) |
| | | Y253H | (2/10) |
| 10 (MBC) | 7 months | E355G | (5/10) |
| | | F317L | (2/10) |
| 11 (MBC) | 6 months | G250E | (8/10) |
| 12 (MBC) | 3 months | Y253F | (3/10) |
| | | E255K | (2/10) |
| | | M351T | (2/10) |
| | | H396R | (2/10) |
| 13 (MBC) | 1.5 months | M351T | (3/10) |
| | | T315I | (2/10) |
| | | Y253H | (2/10) |
| | | E255K | (2/10) |
| 14 (MBC) | 3 months | Y253F | (2/10) |
| | | E255K | (2/10) |
| | | T315I | (2/10) |
| 15 (MBC) | 3 months | E255K | (2/10) |
| 16 (MBC) | 2 months | E255K | (2/10) |
| | | Q252H | (2/10) |
| 17 (MBC) | 4 months | F359V | (8/10) |
| 18 (LBC) | 1 month | M351T | (3/10) |
| | | E255K | (2/10) |
| | | T315I | (2/10) |
| | | Y253F | (2/10) |
| 19 (LBC) | | T315I | (5/10) |
| | | E255K | (2/10) |
| | | Q252R | (2/10) |
| 20 (LBC) | | T315I | (5/10) |
| 21 (LBC) | | T315I | (6/10) |
| 22 (LBC) | | none | |
| 23 (CPNCR) | | V379I | (7/10) |
| 24 (CPNCR) | | F317L | (6/10) |
| 25 (CPNCR) | | E255K | (7/10) |
| 26 (CPNCR) | | F359V | (10/10) |
| 27-35 | | none | |
| 36 (R-MBC) | | T315I | (2/10) |
| | | M343T | (2/10) |
| | | F382L | (2/10) |
| 37 (R-MBC) | | none | |
| 38 (R-MBC) | | none | |
| 39 (R-MBC) | | none | |

MBC denotes relapsed myeloid blast crisis despite STI-571. LBC denotes relapsed lymphoid blast crisis. CP denotes chronic phase with no cytogenetic response. R-MBC denotes pre-STI-571 sample from myeloid blast crisis patients whose disease was subsequently refractory.

Throughout this application, various publications are referenced. The disclosures of these publications are hereby incorporated by reference herein in their entireties. The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method of determining whether a test compound inhibits the tyrosine kinase activity of a mutant Bcr-Abl polypeptide, wherein the mutant Bcr-Abl polypeptide comprises a M244V, Y253H, E255K, T277A, T277P, M278K, V299L, M278L, V304D, V304A, T315I, F317L, E355G, F359I, F359C, F359V, L364I, L364H, V379I, H396R or H396K amino acid substitution in the Bcr-Abl polypeptide sequence shown in SEQ ID NO: 1, the method comprising the steps of: contacting a mammalian cell that expresses said mutant Bcr-Abl polypeptide with the test compound; and monitoring the mammalian cell for the tyrosine kinase activity of the mutant Bcr-Abl polypeptide, wherein an inhibition in tyrosine kinase activity in the presence of the test compound as compared to the absence of the test compound identifies the test compound as an inhibitor of the mutant Bcr-Abl polypeptide.

2. The method of claim 1, wherein the tyrosine kinase activity of the mutant Bcr-Abl polypeptide is measured by examining the phosphotyrosine content of Crkl.

3. The method of claim 1, wherein the amino acid substitution is H396K.

4. The method of claim 1, wherein the amino acid substitution is M244V.

5. The method of claim 1, wherein the amino acid substitution is T277A or T277P.

6. The method of claim 1, wherein the amino acid substitution is M278K or M278L.

7. The method of claim 1, wherein the amino acid substitution is V304D or V304A.

8. The method of claim 1, wherein the amino acid substitution is F317L.

9. The method of claim 1, wherein the amino acid substitution is E355G.

10. The method of claim 1, wherein the amino acid substitution is F359C, F359I, or F359V.

11. The method of claim 1, wherein the amino acid substitution is L364I or L364H.

12. The method of claim 1, wherein the amino acid substitution is V379I.

13. The method of claim 1, wherein the amino acid substitution is H396R.

14. The method of claim 1, wherein the amino acid substitution is T315I.

15. The method of claim 1, wherein the amino acid substitution is Y253H.

16. The method of claim 1, wherein the amino acid substitution is E255K.

17. The method of claim 1, wherein the amino acid substitution is V299L.

18. A method for identifying a compound that inhibits the tyrosine kinase activity of a mutant Bcr-Abl, for use in treating STI-571 resistant cancer in a patient, and wherein said mutation is known to be associated with resistance to STI-571, comprising determining whether a test compound inhibits the tyrosine kinase activity of a mutant Bcr-Abl polypeptide, wherein the Bcr-Abl polypeptide comprises a M244V, Y253H, E255K, T277A, T277P, M278K, M278L, V299L, V304D, T315I, V304A, F317L, E355G, F359C, F359I, F359V, L364I, L364H, V379I, H396R or H396K amino acid substitution in the Bcr-Abl polypeptide sequence shown in SEQ ID NO: 1, the method comprising the steps of: contacting a mammalian cell expressing a mutant Bcr-Abl polypeptide with a test compound; and monitoring the mammalian cells for the tyrosine kinase activity of the mutant Bcr-Abl polypeptide, wherein an inhibition in tyrosine kinase activity in the presence of the test compound as compared to the absence of the test compound identifies the test compound as an inhibitor of the mutant Bcr-Abl polypeptide associated with resistance to STI-571.

* * * * *

SEQUENCE LISTING

<160> NUMBER OF SEQ ID NOS: 21

<210> SEQ ID NO 1
<211> LENGTH: 1130

<212> TYPE: PRT
<213> ORGANISM: Homo sapiens

<400> SEQUENCE: 1

```
Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
            260                 265                 270

Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
    370                 375                 380

Ser Arg Leu Met Thr Gly Asp Thr Tyr Thr Ala His Ala Gly Ala Lys
385                 390                 395                 400
```

-continued

```
Phe Pro Ile Lys Trp Thr Ala Pro Glu Ser Leu Ala Tyr Asn Lys Phe
                405                 410                 415
Ser Ile Lys Ser Asp Val Trp Ala Phe Gly Val Leu Leu Trp Glu Ile
            420                 425                 430
Ala Thr Tyr Gly Met Ser Pro Tyr Pro Gly Ile Asp Leu Ser Gln Val
        435                 440                 445
Tyr Glu Leu Leu Glu Lys Asp Tyr Arg Met Glu Arg Pro Glu Gly Cys
    450                 455                 460
Pro Glu Lys Val Tyr Glu Leu Met Arg Ala Cys Trp Gln Trp Asn Pro
465                 470                 475                 480
Ser Asp Arg Pro Ser Phe Ala Glu Ile His Gln Ala Phe Glu Thr Met
                485                 490                 495
Phe Gln Glu Ser Ser Ile Ser Asp Glu Val Glu Lys Glu Leu Gly Lys
            500                 505                 510
Gln Gly Val Arg Gly Ala Val Ser Thr Leu Leu Gln Ala Pro Glu Leu
        515                 520                 525
Pro Thr Lys Thr Arg Thr Ser Arg Arg Ala Ala Glu His Arg Asp Thr
    530                 535                 540
Thr Asp Val Pro Glu Met Pro His Ser Lys Gly Gln Gly Glu Ser Asp
545                 550                 555                 560
Pro Leu Asp His Glu Pro Ala Val Ser Pro Leu Leu Pro Arg Lys Glu
                565                 570                 575
Arg Gly Pro Pro Glu Gly Gly Leu Asn Glu Asp Glu Arg Leu Leu Pro
            580                 585                 590
Lys Asp Lys Lys Thr Asn Leu Phe Ser Ala Leu Ile Lys Lys Lys Lys
        595                 600                 605
Lys Thr Ala Pro Thr Pro Pro Lys Arg Ser Ser Ser Phe Arg Glu Met
    610                 615                 620
Asp Gly Gln Pro Glu Arg Arg Gly Ala Gly Glu Glu Gly Arg Asp
625                 630                 635                 640
Ile Ser Asn Gly Ala Leu Ala Phe Thr Pro Leu Asp Thr Ala Asp Pro
                645                 650                 655
Ala Lys Ser Pro Lys Pro Ser Asn Gly Ala Gly Val Pro Asn Gly Ala
            660                 665                 670
Leu Arg Glu Ser Gly Gly Ser Gly Phe Arg Ser Pro His Leu Trp Lys
        675                 680                 685
Lys Ser Ser Thr Leu Thr Ser Ser Arg Leu Ala Thr Gly Glu Glu Glu
    690                 695                 700
Gly Gly Gly Ser Ser Ser Lys Arg Phe Leu Arg Ser Cys Ser Ala Ser
705                 710                 715                 720
Cys Val Pro His Gly Ala Lys Asp Thr Glu Trp Arg Ser Val Thr Leu
                725                 730                 735
Pro Arg Asp Leu Gln Ser Thr Gly Arg Gln Phe Asp Ser Ser Thr Phe
            740                 745                 750
Gly Gly His Lys Ser Glu Lys Pro Ala Leu Pro Arg Lys Arg Ala Gly
        755                 760                 765
Glu Asn Arg Ser Asp Gln Val Thr Arg Gly Thr Val Thr Pro Pro Pro
    770                 775                 780
Arg Leu Val Lys Lys Asn Glu Glu Ala Ala Asp Glu Val Phe Lys Asp
785                 790                 795                 800
Ile Met Glu Ser Ser Pro Gly Ser Ser Pro Pro Asn Leu Thr Pro Lys
                805                 810                 815
Pro Leu Arg Arg Gln Val Thr Val Ala Pro Ala Ser Gly Leu Pro His
            820                 825                 830
```

-continued

```
Lys Glu Glu Ala Glu Lys Gly Ser Ala Leu Gly Thr Pro Ala Ala Ala
            835                 840                 845

Glu Pro Val Thr Pro Thr Ser Lys Ala Gly Ser Gly Ala Pro Gly Gly
    850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
                885                 890                 895

Pro Ala Pro Pro Pro Pro Ala Ala Ser Ala Gly Lys Ala Gly Lys Gly
            900                 905                 910

Lys Pro Ser Gln Ser Pro Ser Gln Glu Ala Ala Gly Glu Ala Val Leu
        915                 920                 925

Gly Ala Lys Thr Lys Ala Thr Ser Leu Val Asp Ala Val Asn Ser Asp
    930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ala Leu
            980                 985                 990

Ala Gly Asp Gln Pro Ser Ser Thr Ala Phe Ile Pro Leu Ile Ser Thr
        995                1000                1005

Arg Val Ser Leu Arg Lys Thr Arg Gln Pro Pro Glu Arg Ile Ala
    1010                1015                1020

Ser Gly Ala Ile Thr Lys Gly Val Val Leu Asp Ser Thr Glu Ala
    1025                1030                1035

Leu Cys Leu Ala Ile Ser Arg Asn Ser Glu Gln Met Ala Ser His
    1040                1045                1050

Ser Ala Val Leu Glu Ala Gly Lys Asn Leu Tyr Thr Phe Cys Val
    1055                1060                1065

Ser Tyr Val Asp Ser Ile Gln Gln Met Arg Asn Lys Phe Ala Phe
    1070                1075                1080

Arg Glu Ala Ile Asn Lys Leu Glu Asn Asn Leu Arg Glu Leu Gln
    1085                1090                1095

Ile Cys Pro Ala Thr Ala Gly Ser Gly Pro Ala Ala Thr Gln Asp
    1100                1105                1110

Phe Ser Lys Leu Leu Ser Ser Val Lys Glu Ile Ser Asp Ile Val
    1115                1120                1125

Gln Arg
    1130

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcagagtcag aatccttcag                                              20

<210> SEQ ID NO 3
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 3
tttgtaaaag gctgcccggc                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcaccacca tggagaaggc                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caggaaatga gcttgacaaa                                                   20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaagcttctc cctggcatcc gt                                                22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccaggctct cgggtgcagt cc                                                22

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcgcaacaag cccactgtct atgg                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 9
ccatagacag tgggcttgtt gcgc					24

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgaggagata aatggaaaca a					21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aactcgtcat cctccatgat					20

<210> SEQ ID NO 12
<211> LENGTH: 127
<212> TYPE: PRT
<213> ORGANISM: Homo sapiens

<400> SEQUENCE: 12

```
Trp Lys Lys Tyr Ser Leu Thr Val Ala Val Lys Thr Leu Lys Glu Asp
1               5                   10                  15

Thr Met Glu Val Glu Glu Phe Leu Lys Glu Ala Ala Val Met Lys Glu
            20                  25                  30

Ile Lys His Pro Asn Leu Val Gln Leu Leu Gly Val Cys Thr Arg Glu
        35                  40                  45

Pro Pro Phe Tyr Ile Ile Thr Glu Phe Met Thr Tyr Gly Asn Leu Leu
    50                  55                  60

Asp Tyr Leu Arg Glu Cys Asn Arg Gln Glu Val Asn Ala Val Val Leu
65                  70                  75                  80

Leu Tyr Met Ala Thr Gln Ile Ser Ser Ala Met Glu Tyr Leu Glu Lys
                85                  90                  95

Lys Asn Phe Ile His Arg Asp Leu Ala Ala Arg Asn Cys Leu Val Gly
            100                 105                 110

Glu Asn His Leu Val Lys Val Ala Asp Phe Gly Leu Ser Arg Leu
        115                 120                 125
```

<210> SEQ ID NO 13
<211> LENGTH: 9
<212> TYPE: DNA
<213> ORGANISM: Homo sapiens

<400> SEQUENCE: 13 gtgaagacc					9

<210> SEQ ID NO 14
<211> LENGTH: 21
<212> TYPE: DNA
<213> ORGANISM: Homo sapiens

<400> SEQUENCE: 14

```
aaagaagctg cagtcatgaa a                                              21
```

<210> SEQ ID NO 15
<211> LENGTH: 21
<212> TYPE: DNA
<213> ORGANISM: Homo sapiens

<400> SEQUENCE: 15

```
atcatcactg agttcatgac c                                              21
```

<210> SEQ ID NO 16
<211> LENGTH: 9
<212> TYPE: DNA
<213> ORGANISM: Homo sapiens

<400> SEQUENCE: 16

```
gctgatttt                                                             9
```

<210> SEQ ID NO 17
<211> LENGTH: 21
<212> TYPE: DNA
<213> ORGANISM: Homo sapiens

<400> SEQUENCE: 17

```
atcatcattg agttcatgac c                                              21
```

<210> SEQ ID NO 18
<211> LENGTH: 68
<212> TYPE: DNA
<213> ORGANISM: Homo sapiens

<400> SEQUENCE: 18

```
gggtctgcac ccgggagccc ccgttctata tcatcactga gttcatgacc tacgggaacc    60
tcctgagg                                                             68
```

<210> SEQ ID NO 19
<211> LENGTH: 68
<212> TYPE: DNA
<213> ORGANISM: Homo sapiens

<400> SEQUENCE: 19

```
gggtctgcac ccgggagccc ccgttctata tcatcattga gttcatgacc tacgggaacc    60
tcctgagg                                                             68
```

<210> SEQ ID NO 20
<211> LENGTH: 180
<212> TYPE: PRT
<213> ORGANISM: Homo sapiens

<400> SEQUENCE: 20

```
Asp Lys Trp Glu Met Glu Arg Thr Asp Ile Thr Met Lys His Lys Leu
 1               5                  10                  15

Gly Gly Gly Gln Tyr Gly Glu Val Tyr Glu Gly Val Trp Lys Lys Tyr
                20                  25                  30

Ser Leu Thr Val Ala Val Lys Thr Leu Lys Glu Asp Thr Met Glu Val
            35                  40                  45

Glu Glu Phe Leu Lys Glu Ala Ala Val Met Lys Glu Ile Lys His Pro
        50                  55                  60

Asn Leu Val Gln Leu Leu Gly Val Cys Thr Arg Glu Pro Pro Phe Tyr
65                  70                  75                  80
```

```
Ile Ile Thr Glu Phe Met Thr Tyr Gly Asn Leu Leu Asp Tyr Leu Arg
                85                  90                  95

Glu Cys Asn Arg Gln Glu Val Asn Ala Val Val Leu Leu Tyr Met Ala
            100                 105                 110

Thr Gln Ile Ser Ser Ala Met Glu Tyr Leu Glu Lys Lys Asn Phe Ile
        115                 120                 125

His Arg Asp Leu Ala Ala Arg Asn Cys Leu Val Gly Glu Asn His Leu
    130                 135                 140

Val Lys Val Ala Asp Phe Gly Leu Ser Arg Leu Met Thr Gly Asp Thr
145                 150                 155                 160

Tyr Thr Ala His Ala Gly Ala Lys Phe Pro Ile Lys Trp Thr Ala Pro
                165                 170                 175

Glu Ser Leu Ala
            180

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 21

Gly Xaa Gly Xaa Xaa Gly Xaa Val
1               5
```